US008476051B2

(12) United States Patent
Ma et al.

(10) Patent No.: US 8,476,051 B2
(45) Date of Patent: Jul. 2, 2013

(54) **THERMOSTABLE ALCOHOL DEHYDROGENASE DERIVED FROM *THERMOCOCCUS GUAYMASENSIS***

(76) Inventors: Kesen Ma, Ontario (CA); Xiangxian Ying, Hangzhou (CN)

( * ) Notice: Subject to any disclaimer, the term of this patent is extended or adjusted under 35 U.S.C. 154(b) by 0 days.

(21) Appl. No.: 13/072,193

(22) Filed: Mar. 25, 2011

(65) Prior Publication Data
US 2011/0177579 A1 Jul. 21, 2011

Related U.S. Application Data

(63) Continuation of application No. PCT/CA2009/001349, filed on Sep. 25, 2009.

(60) Provisional application No. 61/136,714, filed on Sep. 26, 2008.

(51) Int. Cl.
*C12N 9/04* (2006.01)
*C07K 14/00* (2006.01)
*C12P 21/00* (2006.01)
*C12Q 1/32* (2006.01)

(52) U.S. Cl.
USPC ............. 435/190; 435/69.1; 435/26; 530/350

(58) Field of Classification Search
USPC ...... 435/190, 69.1, 26, 320.1, 252.3; 530/350
See application file for complete search history.

(56) References Cited

U.S. PATENT DOCUMENTS
5,908,924 A 6/1999 Burdette et al.
2008/0220487 A1 9/2008 Zeikus et al.

FOREIGN PATENT DOCUMENTS
WO WO 2009/042984 4/2009
WO WO 99/21971 1/2010

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Bao, Q. et al., Genbank Acc. No. AAM23957 Jun. 4, 2004.
Written Opinion for corresponding application PCT/CA2009/001349 dated Jan. 4, 2010.
International Search Report for corresponding PCT/CA2009/001349 dated Jan. 4, 2010.
Burstein, Y. Genbank Acc. No. CAA46053 Jan. 8, 1997.
Olofsson, L., N. A. Nicholls, and S. Wikman. 2005. TBADH activity in water-miscible organic solvents: correlations between enzyme performance, enantioselectivity and protein structure through spectroscopic studies. Org. Biomol. Chem. 3:750-755.
Bogin, O., I. Levin, Y. Hacham, S. Tel-Or, M. Peretz, F. Frolow, and Y. Burstein. 2002. Structural basis for the enhanced thermal stability of alcohol dehydrogenase mutants from the mesophilic bacterium Clostridium beijerinckii: contribution of salt bridging. Protein Sci. 11:2561-2574.
Bogin, O., M. Peretz, and Y. Burstein. 1997. Thermoanaerobacter brockii alcohol dehydrogenase: characterization of the active site metal and its ligand amino acids. Protein Sci. 6:450-458.
Canganella, F., W. J. Jones, A. Gambacorta, and G. Antranikian. 1998. *Thermococcus guaymasensis* sp. nov. and Thermococcus aggregans sp. nov., two novel thermophilic archaea isolated from the Guaymas Basin hydrothermal vent site. Int. J. Syst. Bacteriol. 48:1181-1185.
Gonzalez, E., M. R. Fernández, C. Larroy, L. Solà, M. A. Pericàs, X. Parés, and J. A. Biosca. 2000. Characterization of a (2R, 3R)-2, 3-butanediol dehydrogenase as the Saccharomyces cerevisiae YAL060W gene product. J. Biol. Chem. 275: 35876-35885.
Heiss, C., M. Laivenieks, J. G. Zeikus, and R. S. Phillips. 2001. The stereospecificity of secondary alcohol dehydrogenase from Thermoanaerobacter ethanolicus is partially determined by active site water. J. Am. Chem. Soc. 123:345-346.
Keinan, E., K. K. Seth, and R. Lamed. 1986. Organic synthesis with enzymes. 3. TBADH-catalyzed reduction of chloro ketones. Total synthesis of (+)-(S, S)-(cis-6-methyltetrahydropyran-2-yl)-acetic acid: a civet constituent. J. Am. Chem. Soc. 108:3473-3480.
Korkhin, Y., A. J. Kalb (Gilboa), M. Peretz, O. Bogin, Y. Burstein, and F. Frolow. 1998. NADP-dependent bacterial alcohol dehydrogenases: crystal structure, cofactor-binding and cofactor specificity of the ADHs of Clostridium beijerinckii and Thermoanaerobacter brockii. J. Mol. Biol. 278:967-981.
Musa, M. M., K. I. Ziegelmann-Fjeld, C. Vieille, J. G. Zeikus, and R. S. Phillips. 2007. Asymmetric reduction and oxidation of aromatic ketones and alcohols using W110A secondary alcohol dehydrogenase from Thermoanaerobacter ethanolicus. J. Org. Chem. 72:30-34.
Gonzalez, J. et al., Genbank Acc. No. ZP_05092697.1 Jul. 20, 2009.
Ying et al., "Characterization of a Zinc-Containing Alcohol Dehydrogenase with Stereoselectivity from the Hyperthermophilic Archaeon *Thermococcus guaymasensis*", Journal of Bacteriology, Jun. 2011, vol. 193, No. 12, pp. 3009-3019.
European Search Report from European Patent Application No. 09815527.8 (Sep. 5, 2012).
Sequence 4 from WO0146446, Aug. 6, 2001.

* cited by examiner

*Primary Examiner* — Delia Ramirez
(74) *Attorney, Agent, or Firm* — Lathrop & Gage LLP; Brian C. Trinque; Andrew T. Wilkins

(57) ABSTRACT

An alcohol dehydrogenase (ADH) from hyperthermophilic archaeon *Thermococcus guaymasensis* was purified to homogeneity and was found to be a homotetramer with a subunit size of 40±1 kDa. The gene encoding the enzyme was cloned and sequenced, and found to have significant sequence homology to known zinc-containing ADHs and L-threonine dehydrogenases with both binding motifs of catalytic zinc and NADP+. The wild-type enzyme is a primary-secondary ADH that exhibits a substrate preference for secondary alcohols and corresponding ketones, and exhibits unusual stereoselectivity. The wild-type enzyme was found to have outstanding thermostability, demonstrating 60% activity after incubation at 80° C. for 40 hours. Site-directed mutagenesis was used to substitute the cyteine residue at position 56 with a serine, to provide the TgADH(C56S) mutant. In the assays that we carried out, we found virtually no difference in enzyme activity and oxygen-sensitivity between the mutant TgADH (C56S) and wild type TgADH.

8 Claims, 15 Drawing Sheets

*ATG*A*G*C*AAGATGCGCGGTTTTGCAATGGTGGACTTCGGCAAGGCCGAGTGGATT
GAGAAGGAGAGGCCGAAGCCCGGGCCGTACGATGCAATCGTCAAGCCCATTGCA
GTCGCCCCATGCACCTCGGACATCCACACGGTCTTTGAGGCAGCGTTTCCCAGG
GAGATGTGTGAGTTCCCGCGCATACTGGGTCACGAAGCAGTCGGAGAGGTAGTC
GAGGTCGGAAGCCACGTCAAGGACTTCAAGCCCGGGGACAGGGTTGTTGTCCCG
GCAATAACTCCCGACTGGAGGACCCTTGACGTTCAGAGGGGCTACCACCAGCAC
TCCGGTGGAATGCTCGCCGGATGGAAGTTCAGCAACCCCCTCAAGGAGGGCGGT
AAGGACGGTGTGTTTGCAGAATACTTCCACGTCAACGACGCTGACATGAACCTG
GCACACCTTCCGGACGAAATCAAGCCGGAAGTCGCTGTCATGGCCACCGACATG
ATGACCACGGGATTCCACGGCGCCGAGCTCGCCGACATTCCGCTCGGAGGAACA
GTCGCCGTCATTGGAATTGGACCGGTCGGCCTGATGGCGGTTGCCGGGGCAAGA
CTGCTCGGTGCCGGAAGGATCATCGCGGTCGGCAGCAGGCCGGTGTGCGTTGAG
GCCGCTAAGTACTACGGAGCCACCGACATAGTCAACCGCAGGGAGCACCCGGAC
ATCGCCGGAAGGATCCTGGAGCTGACCGGTGGAGAGGGTGTTGATTCGGTGATA
ATCGCCGGCGGAAACGTTGACGTAATGAAGACCGCGGTGAAGATAGTCAAGCCC
GGAGGAACGGTGGCCAACATCAACTACTTCGGCAGCGGTGACTACCTCCCGATC
CCGAGGATTGAGTGGGGCCAGGGAATGGCCCACAAGACCATCAAGGGAGGGCTC
TGCCCAGGCGGACGCCTGAGGATGGAGCGCCTGCTTGACCTCATCAAGTACGGC
AGGGTTGACCCGTCAAGGCTCATAACCCACAAGTTCAAGGGATTCGATAAGATA
CCAGAAGCCCTCTACCTGATGAAGGACAAGCCCAAAGACCTGATAAAGCCCGTG
GTCATCATAGAGGAG*TGA*   (SEQ ID NO:1)

Fig. 1

MS₁KMRGFAMVDFGKAEWIEKERPKPGPYDAIVKPIAVAPCTSDIHTVFEAAFP
REMCEFPRILGHEAVGEVVEVGSHVKDFKPGDRVVVPAITPDWRTLDVQRGYHQ
HSGGMLAGWKFSNPLKEGGKDGVFAEYFHVNDADMNLAHLPDEIKPEVAVMATD
MMTTGFHGAELADIPLGGTVAVIGIGPVGLMAVAGARLLGAGRIIAVGSRPVCV
EAAKYYGATDIVNRREHPDIAGRILELTGGEGVDSVIIAGGNVDVMKTAVKIVK
PGGTVANINYFGSGDYLPIPRIEWGQGMAHKTIKGGLCPGGRLRMERLLDLIKY
GRVDPSRLITHKFKGFDKIPEALYLMKDKPKDLIKPVVIEE (SEQ ID NO: 2)

Fig. 2

A₁GCAAGATGCGCGGTTTTGCAATGGTGGACTTCGGCAAGGCCGAGTGGATTGAGAAG
GAGAGGCCGAAGCCCGGGCCGTACGATGCAATCGTCAAGCCCATTGCAGTCGCCCCAT
GCACCTCGGACATCCACACGGTCTTTGAGGCAGCGTTTCCCAGGGAGATGTGTGAGTT
CCCGCGCATACTGGGTCACGAAGCAGTCGGAGAGGTAGTCGAGGTCGGAAGCCACGT
CAAGGACTTCAAGCCCGGGGACAGGGTTGTTGTCCCGGCAATAACTCCCGACTGGAGG
ACCCTTGACGTTCAGAGGGGCTACCACCAGCACTCCGGTGGAATGCTCGCCGGATGGA
AGTTCAGCAACCCCCTCAAGGAGGGCGGTAAGGACGGTGTGTTTGCAGAATACTTCCA
CGTCAACGACGCTGACATGAACCTGGCACACCTTCCGGACGAAATCAAGCCGGAAGTC
GCTGTCATGGCCACCGACATGATGACCACGGGATTCCACGGCGCCGAGCTCGCCGAC
ATTCCGCTCGGAGGAACAGTCGCCGTCATTGGAATTGGACCGGTCGGCCTGATGGCGG
TTGCCGGGGCAAGACTGCTCGGTGCCGGAAGGATCATCGCGGTCGGCAGCAGGCCGG
TGTGCGTTGAGGCCGCTAAGTACTACGGAGCCACCGACATAGTCAACCGCAGGGAGCA
CCCGGACATCGCCGGAAGGATCCTGGAGCTGACCGGTGGAGAGGGTGTTGATTCGGT
GATAATCGCCGGCGGAAACGTTGACGTAATGAAGACCGCGGTGAAGATAGTCAAGCCC
GGAGGAACGGTGGCCAACATCAACTACTTCGGCAGCGGTGACTACCTCCCGATCCCGA
GGATTGAGTGGGGCCAGGGAATGGCCCACAAGACCATCAAGGGAGGGCTCTGCCCAG
GCGGACGCCTGAGGATGGAGCGCCTGCTTGACCTCATCAAGTACGGCAGGGTTGACC
CGTCAAGGCTCATAACCCACAAGTTCAAGGGATTCGATAAGATACCAGAAGCCCTCTAC
CTGATGAAGGACAAGCCCAAAGACCTGATAAAGCCCGTGGTCATCATAGAGGAG*TGA*
(SEQ ID NO: 3)

Fig. 3

S₁KMRGFAMVDFGKAEWIEKERPKPGPYDAIVKPIAVAPCTSDIHTVFEAAFPR
EMCEFPRILGHEAVGEVVEVGSHVKDFKPGDRVVVPAITPDWRTLDVQRGYHQH
SGGMLAGWKFSNPLKEGGKDGVFAEYFHVNDADMNLAHLPDEIKPEVAVMATDM
MTTGFHGAELADIPLGGTVAVIGIGPVGLMAVAGARLLGAGRIIAVGSRPVCVE
AAKYYGATDIVNRREHPDIAGRILELTGGEGVDSVIIAGGNVDVMKTAVKIVKP
GGTVANINYFGSDYLPIPRIEWGQGMAHKTIKGGLCPGGRLRMERLLDLIKYG
RVDPSRLITHKFKGFDKIPEALYLMKDKPKDLIKPVVIEE (SEQ ID NO: 4)

Fig. 4

*ATG*__A__₁__GC__AAGATGCGCGGTTTTGCAATGGTGGACTTCGGCAAGGCCGAGTGGAT
TGAGAAGGAGAGGCCGAAGCCCGGGCCGTACGATGCAATCGTCAAGCCCATTGC
AGTCGCCCCATGCACCTCGGACATCCACACGGTCTTTGAGGCAGCGTTTCCCAG
GGAGATG__AGC__GAGTTCCCGCGCATACTGGGTCACGAAGCAGTCGGAGAGGTAGT
CGAGGTCGGAAGCCACGTCAAGGACTTCAAGCCCGGGGACAGGGTTGTTGTCCC
GGCAATAACTCCCGACTGGAGGACCCTTGACGTTCAGAGGGGCTACCACCAGCA
CTCCGGTGGAATGCTCGCCGGATGGAAGTTCAGCAACCCCCTCAAGGAGGGCGG
TAAGGACGGTGTGTTTGCAGAATACTTCCACGTCAACGACGCTGACATGAACCT
GGCACACCTTCCGGACGAAATCAAGCCGGAAGTCGCTGTCATGGCCACCGACAT
GATGACCACGGGATTCCACGGCGCCGAGCTCGCCGACATTCCGCTCGGAGGAAC
AGTCGCCGTCATTGGAATTGGACCGGTCGGCCTGATGGCGGTTGCCGGGGCAAG
ACTGCTCGGTGCCGGAAGGATCATCGCGGTCGGCAGCAGGCCGGTGTGCGTTGA
GGCCGCTAAGTACTACGGAGCCACCGACATAGTCAACCGCAGGGAGCACCCGGA
CATCGCCGGAAGGATCCTGGAGCTGACCGGTGGAGAGGGTGTTGATTCGGTGAT
AATCGCCGGCGGAAACGTTGACGTAATGAAGACCGCGGTGAAGATAGTCAAGCC
CGGAGGAACGGTGGCCAACATCAACTACTTCGGCAGCGGTGACTACCTCCCGAT
CCCGAGGATTGAGTGGGGCCAGGGAATGGCCCACAAGACCATCAAGGGAGGGCT
CTGCCCAGGCGGACGCCTGAGGATGGAGCGCCTGCTTGACCTCATCAAGTACGG
CAGGGTTGACCCGTCAAGGCTCATAACCCACAAGTTCAAGGGATTCGATAAGAT
ACCAGAAGCCCTCTACCTGATGAAGGACAAGCCCAAAGACCTGATAAAGCCCGT
GGTCATCATAGAGGAG*TGA*   (SEQ ID NO: 5)

Fig. 5

MS₁KMRGFAMVDFGKAEWIEKERPKPGPYDAIVKPIAVAPCTSDIHTVFEAAFP
REMSEFPRILGHEAVGEVVEVGSHVKDFKPGDRVVVPAITPDWRTLDVQRGYHQ
HSGGMLAGWKFSNPLKEGGKDGVFAEYFHVNDADMNLAHLPDEIKPEVAVMATD
MMTTGFHGAELADIPLGGTVAVIGIGPVGLMAVAGARLLGAGRIIAVGSRPVCV
EAAKYYGATDIVNRREHPDIAGRILELTGGEGVDSVIIAGGNVDVMKTAVKIVK
PGGTVANINYFGSGDYLPIPRIEWGQGMAHKTIKGGLCPGGRLRMERLLDLIKY
GRVDPSRLITHKFKGFDKIPEALYLMKDKPKDLIKPVVIEE (SEQ ID NO: 6)

Fig. 6

*ATG*CACCATCATCATCATCATTCTTCTGGTCTGGTGCCACGCGGTTCTGGTATGAAAGAAACCGCTG
CTGCTAAATTCGAACGCCAGCACATGGACAGCCCAGATCTGGGTACCGACGACGACGACAAGGCCA
TGGCTGATATCGGATCCGAATTCATGA₁GCAAGATGCGCGGTTTTGCAATGGTGGACTTCGGCAAGGCCG
AGTGGATTGAGAAGGAGAGGCCGAAGCCCGGGCCGTACGATGCAATCGTCAAGCCCATTGCAGTCGCCCC
ATGCACCTCGGACATCCACACGGTCTTTGAGGCAGCGTTTCCCAGGGAGATGTGTGAGTTCCCGCGCATAC
TGGGTCACGAAGCAGTCGGAGAGGTAGTCGAGGTCGGAAGCCACGTCAAGGACTTCAAGCCCGGGGACAG
GGTTGTTGTCCCGGCAATAACTCCCGACTGGAGGACCCTTGACGTTCAGAGGGGCTACCACCAGCACTCCG
GTGGAATGCTCGCCGGATGGAAGTTCAGCAACCCCCTCAAGGAGGGCGGTAAGGACGGTGTGTTTGCAGAA
TACTTCCACGTCAACGACGCTGACATGAACCTGGCACACCTTCCGGACGAAATCAAGCCGGAAGTCGCTGTC
ATGGCCACCGACATGATGACCACGGGATTCCACGGCGCCGAGCTCGCCGACATTCCGCTCGGAGGAACAG
TCGCCGTCATTGGAATTGGACCGGTCGGCCTGATGGCGGTTGCCGGGGCAAGACTGCTCGGTGCCGGAAG
GATCATCGCGGTCGGCAGCAGGCCGGTGTGCGTTGAGGCCGCTAAGTACTACGGAGCCACCGACATAGTC
AACCGCAGGGAGCACCCGGACATCGCCGGAAGGATCCTGGAGCTGACCGGTGGAGAGGGTGTTGATTCGG
TGATAATCGCCGGCGGAAACGTTGACGTAATGAAGACCGCGGTGAAGATAGTCAAGCCCGGAGGAACGGTG
GCCAACATCAACTACTTCGGCAGCGGTGACTACCTCCCGATCCCGAGGATTGAGTGGGGCCAGGGAATGGC
CCACAAGACCATCAAGGGAGGGCTCTGCCCAGGCGGACGCCTGAGGATGGAGCGCCTGCTTGACCTCATC
AAGTACGGCAGGGTTGACCCGTCAAGGCTCATAACCCACAAGTTCAAGGGATTCGATAAGATACCAGAAGCC
CTCTACCTGATGAAGGACAAGCCCAAAGACCTGATAAAGCCCGTGGTCATCATAGAGGAG*TGA* (SEQ ID NO: 7)

Fig. 7

**M*HHHHHH*S SGLVPRGSGMKETAAAKFERQHMDSPDLGTDDDDKAMADIGSEF**MS
₁KMRGFAMVDFGKAEWIEKERPKPGPYDAIVKPIAVAPCTSDIHTVFEAAFPRE
MCEFPRILGHEAVGEVVEVGSHVKDFKPGDRVVVPAITPDWRTLDVQRGYHQHS
GGMLAGWKFSNPLKEGGKDGVFAEYFHVNDADMNLAHLPDEIKPEVAVMATDMM
TTGFHGAELADIPLGGTVAVIGIGPVGLMAVAGARLLGAGRIIAVGSRPVCVEA
AKYYGATDIVNRREHPDIAGRILELTGGEGVDSVIIAGGNVDVMKTAVKIVKPG
GTVANINYFGSGDYLPIPRIEWGQGMAHKTIKGGLCPGGRLRMERLLDLIKYGR
VDPSRLITHKFKGFDKIPEALYLMKDKPKDLIKPVVIEE (SEQ ID NO: 8)

Fig. 8

***ATG*CACCATCATCATCATCATTCTTCTGGTCTGGTGCCACGCGGTTCTGGTATGAAAGAAACCGCTG CTGCTAAATTCGAACGCCAGCACATGGACAGCCCAGATCTGGGTACCGACGACGACGACAAGGCCA TGGCTGATATCGGATCCGAATTCATGA₁GCAAGATGCGCGGTTTTGCAATGGTGGACTTCGGCAAGGCCG AGTGGATTGAGAAGGAGAGGCCGAAGCCCGGGCCGTACGATGCAATCGTCAAGCCCATTGCAGTCGCCCC ATGCACCTCGGACATCCACACGGTCTTTGAGGCAGCGTTTCCCAGGGAGATGAGCGAGTTCCCGCGCATAC TGGGTCACGAAGCAGTCGGAGAGGTAGTCGAGGTCGGAAGCCACGTCAAGGACTTCAAGCCCGGGGACAG GGTTGTTGTCCCGGCAATAACTCCCGACTGGAGGACCCTTGACGTTCAGAGGGGCTACCACCAGCACTCCG GTGGAATGCTCGCCGGATGGAAGTTCAGCAACCCCCTCAAGGAGGGCGGTAAGGACGGTGTGTTTGCAGAA TACTTCCACGTCAACGACGCTGACATGAACCTGGCACACCTTCCGGACGAAATCAAGCCGGAAGTCGCTGTC ATGGCCACCGACATGATGACCACGGGATTCCACGGCGCCGAGCTCGCCGACATTCCGCTCGGAGGAACAG TCGCCGTCATTGGAATTGGACCGGTCGGCCTGATGGCGGTTGCCGGGGCAAGACTGCTCGGTGCCGGAAG GATCATCGCGGTCGGCAGCAGGCCGGTGTGCGTTGAGGCCGCTAAGTACTACGGAGCCACCGACATAGTC AACCGCAGGGAGCACCCGGACATCGCCGGAAGGATCCTGGAGCTGACCGGTGGAGAGGGTGTTGATTCGG TGATAATCGCCGGCGGAAACGTTGACGTAATGAAGACCGCGGTGAAGATAGTCAAGCCCGGAGGAACGGTG GCCAACATCAACTACTTCGGCAGCGGTGACTACCTCCCGATCCCGAGGATTGAGTGGGGCCAGGGAATGGC CCACAAGACCATCAAGGGAGGGCTCTGCCCAGGCGGACGCCTGAGGATGGAGCGCCTGCTTGACCTCATC AAGTACGGCAGGGTTGACCCGTCAAGGCTCATAACCCACAAGTTCAAGGGATTCGATAAGATACCAGAAGCC CTCTACCTGATGAAGGACAAGCCCAAAGACCTGATAAAGCCCGTGGTCATCATAGAGGAG*TGA* (SEQ ID NO: 9)

Fig. 9

M*HHHHHH**SSGLVPRGSGMKETAAAKFERQHMDSPDLGTDDDDKAMADIGSEFMS
₁KMRGFAMVDFGKAEWIEKERPKPGPYDAIVKPIAVAPCTSDIHTVFEAAFPRE
MSEFPRILGHEAVGEVVEVGSHVKDFKPGDRVVVPAITPDWRTLDVQRGYHQHS
GGMLAGWKFSNPLKEGGKDGVFAEYFHVNDADMNLAHLPDEIKPEVAVMATDMM
TTGFHGAELADIPLGGTVAVIGIGPVGLMAVAGARLLGAGRIIAVGSRPVCVEA
AKYYGATDIVNRREHPDIAGRILELTGGEGVDSVIIAGGNVDVMKTAVKIVKPG
GTVANINYFGSGDYLPIPRIEWGQGMAHKTIKGGLCPGGRLRMERLLDLIKYGR
VDPSRLITHKFKGFDKIPEALYLMKDKPKDLIKPVVIEE (SEQ ID NO:10)

```
TgADH    SKMRGFAMVDFGKAEWIEKERPKPGPYDAIVKPIAVAPCTSDIHTVFEAAFPREMCEFPR      (SEQ ID NO:4)
TbADH    --MKGFAMLSIGKVGWIEKEKPAPGPFDAIVRPLAVAPCTSDIHTVFEGAIG---ERHNM      (SEQ ID NO:31)
CbADH    --MKGFAMLGINKLGWIEKERPVAGSYDAIVRPLAVSPCTSDIHTVFEGALG---DRKNM      (SEQ ID NO:32)
         *:****:.:.*   *****:*  .*.:****:*:**:***********.*:        .

TgADH    ILGHEAVGEVVEVGSEVKDFKPGDRVVVPAITPDWRTLDVQRGYFQHSGGMLAGWKFSNP
TbADH    ILGHEAVGEVVEVGSEVKDFKPGDRVVVPAITPDWRTSEVQRGYFQHSGGMLAGWKFSN-
CbADH    ILGHEAVGEVVEVGSEVKDFKPGDRVIVPCTTPDWRSLEVQAGFQQHSNGMLAGWKFSN-
         **************.***********:**. *****: :** *::***.**********

TgADH    LKECCKDCVFAEYFHVNDADMNLAHLPDEIKPEVAVMATDMMTTGFHCAELADIPLCCTV
TbADH    ----VKDCVFGEFFHVNDADMNLAHLPKEIPLEAAVMIPDMMTTGFHCAELADIELCATV
CbADH        FKDGVFGEYFHVNDADMNLAILPKDMPLENAVMITDMMTGFHGAELADIQMGSSV
             *****.*:***********  **.::   * *** .***************  :*.:*

TgADH    AVIGIGPVGLMAVAGARLLGAGRIIAVGSRPVCVEAAKYYGATDIVNRREHPDIAGRILE
TbADH    AVLGIGPVGLMAVAGAKLRGAGRIIAVGSRPVCVDAAKYYGATDIVNYKDGPIES-QIMN
CbADH    VVIGIGAVGLMGIAGAKLRGAGRIIGVGSRPICVEAAKFYGATDILNYKNG-HIVDQVMK
         .*:***.****.:***:* ******.*****:**:***:*****:*   ::  ::::

TgADH    LTGGEGVDSVIIAGGNVDVMKTAVKIVKPGGTVANINYFGSGDYLPIPRIEWGCGMAHKT
TbADH    LTEGKGVDAAIIAGGNADIMATAVKIVKPGGTIANVNYFGEGEVLPVPRLEWGCGMAHKT
CbADH    LTNGKGVDRVIMAGGGSETLSQAVSMVKPGGIISNINYHGSGDALLIPRVEWGCGMAHKT
         ** *:***  .*:***.  : :  **.:.***** ::*:**.*.*:  * :**:*** ******

TgADH    IKGGLCPGGRLRMERLLDLIKYGRVDPSRLITHKFKGFDKIPEALYLMKDKPKDLIKPVV
TbADH    IKGGLCPGGRLRMERLIDLVFYKRVDPSKLVTHVFRGFDNIEKAFMLMKDKPKDLIKPVV
CbADH    IKGGLCPGGRLRAEMLRDMVVYNRVDLSKLVTHVYHGFDHIEEALLLMKDKPKDLIKAVV
         ************ * *.::  * ***.*:*.** :.*** :.*: ***********.**

TgADH    IIEE
TbADH    ILA-
CbADH    IL--
         *:
```

FIGURE 15

```
TgADH     SKMRGFAMVDFGKAEWIEKERPKPGPYDAIVKPIAVAPCTSDIHTVFEAAFPREMCEFPR        (SEQ ID NO:4)
TbADH     ------LSI--VG-----K-A---F----R-L--A---S-------G-IG---ERENM        (SEQ ID NO:31)
CbADH     -K----LGIN-LG-------VA-S-----R-L--S----------C-LG---DRKNM        (SEQ ID NO:32)
          *:****:.:.*  *****:* .*.:****:*:**:***********.*:      .

TgADH     ILGHEAVGEVVEVGSHVKDFKPGDRVVVPAITPDWRTLDVQRGYHQHSGGMLAGWKFSNP
TbADH     ---------------E---------------------SE---------------W----
CbADH     ---------------E----------I--CT-----S-E--A-FQ---N----------
          ***************.**********:**. *****: :** *::***.**********

TgADH     LKEGGKDGVFAEYFHVNDADMNLAHLPDEIKPEVAVMATDMMTTGFHGAELADIPLGGTV
TbADH         V-----C-F--------------K--PL-A---IP---------------E--A--
CbADH         F-----G-Y-----------I--KDMPL-N---I------S----------QM-SS-
              *****.*:*********** **.::   *  ***  .****:**********  :*.:*

TgADH     AVIGIGPVGLMAVAGARLLGAGRIIAVGSRPVCVEAAKYYGATDIVNRREHPDIAGRILE
TbADH     --L---P---------K-R--------------D-------------YKDG-IES-Q-MN
CbADH     V-----A----GI---K-R------G-----I-------I-------L-YKNG II-VDQVMK
          .*:***.****.:***:*  ******.*****:**:***:******:*  ::     ::::

TgADH     LIGGEGVDSVIIAGGNVDVMKTAVKIVKPGGTVANINYFGSGDYLPIPRIEWGQGMAEKT
TbADH     --E-K---AA------A-I-A----------TI--V--F-E-EV--V--L---C------
CbADH     --N-E---R--M---GSETLSQ--SM-----IIS----H----A-LI--V---C------
          ** *:*** .*:***. : :  **.:****** ::*:**.*.*: * :**:*** ******

TgADH     IKGGLCPGGRLRMERILDLIKYGRVDPSRLITHKFKGFDKIPEALYLMKDKPKDLIKPVV
TbADH              C         I  VF K     K V  V R   N EK FM
CbADH     ------------A-M-R-MVV-N---L-K-V--VYH---H-E---L------------A--
          *********** * * *:: * *** *:*:** ::***:* :*: ***********.**

TgADH     IIEK
TbADH     -IA
CbADH     -I
          *:
```

THERMOSTABLE ALCOHOL DEHYDROGENASE DERIVED FROM *THERMOCOCCUS GUAYMASENSIS*

CROSS REFERENCE TO RELATED APPLICATIONS

The present application claims the benefit of priority of International Application No. PCT/CA2009/001349, filed Sep. 25, 2009, which claims priority to U.S. Provisional Patent Application No. 61/136,714, filed Sep. 26, 2008. The entire contents of each of the above documents are incorporated herein by reference.

FIELD OF THE INVENTION

Generally, the present invention relates to thermostable enzymes, more particularly enzymes derived from the hyperthermophilic archaeon *Thermococcus guaymasensis* (Tg). In particular, the invention relates to novel polynucleotides and polypeptides derived from *Thermococcus guaymasensis* (Tg) and which provide a novel thermostable alcohol dehydrogenase, TgADH, and variants thereof. These enzymes find utility for example as biocatalysts.

BACKGROUND OF THE INVENTION

There is a rising demand for chiral compounds in various industries, including the pharmaceutical, agrochemical, food and beverage, cosmetic, diagnostic and research industries, among others. Although considerable progress in chiral chemistry has been achieved in recent years, chemists still face many challenges in the area of stereoselective synthesis. Selectivity in a chiral synthesis reaction is important in order to achieve a high yield of a chiral compound having the desired stereochemistry. Stereochemistry is important because different stereoisomers of chiral compound (e.g. enantiomers and diasteriomers) can have very different functions. For instance, one enantiomer in a racemic drug mixture may be entirely responsible for the therapeutic effects of a drug in the body. It is therefore often desirable to produce the single stereoisomer of interest for a given application. Despite the high demand for stereoselective chiral molecules, their productivity has been low. Process and cost limitations often preclude stereoselective synthesis. Therefor, in many cases, racemic mixtures are used. Manufacturers are therefore looking for more rapid, efficient, and less expensive ways to produce stereospecific chiral molecules. Biocatalysis reactions are currently being explored over conventional chemical catalysis for selective production of chiral molecules. Biocatalysis reactions exploit enzymes, which are protein-based molecules that catalyze biological reactions. Enzymes typically display three types of selectivity that make them desirable. They are chemoselective, meaning that they act on a specific type or range of functionality, such that other sensitive functionalities in the reaction mixture (that may be targeted under chemical catalysis) are spared, resulting in a cleaner reaction. They are regioselective, meaning that, due to their complex three-dimensional structure, they may distinguish between functional goups which are located in different regions of a substrate molecule. They are enantioselective, meaning that they can recognize chirality in a substrate and tend to preferentially transform prochiral molecules into molecules having a specific chirality. Biocatalysts can often enable chiral compound synthesis in fewer steps and with lower solvent usage than conventional chemical methods. Added advantages of biocatalysts are that they are environmentally acceptable, being completely degraded in the environment, and tend to act under mild conditions, which minimizes problems of undesired side-reactions that often plague traditional chemical methodology.

One enzyme of interest as a biocatalyst is alcohol dehydrogenase (ADH). ADH enzymes are a family of enzymes that catalyse reactions to produce aldehydes, ketones, and alcohols and therefore have commercial and industrial importance. Chiral alcohols can be important building blocks in a variety of high-value chemicals including, but not limited to, pharmaceuticals, agrochemicals, and various other chiral compounds. Some ADHs preferentially catalyze the oxidation of alcohols to aldehydes and ketones, while others catalyze the reverse of such reaction, for example, to produce alcohols for biofuels.

Commercially available enzymatic catalysts typically have several shortcomings that prevent their use in industrial applications. Narrow substrate specificities, poor solvent tolerance and instability at high temperature prevent many ADHs from being used in industrial-scale applications. For instance, certain classic ADH molecules, such as yeast ADH and horse liver ADH, although inexpensive and readily available, react on very few types of alcohols and are very unstable at higher temperatures (>50° C.). ADHs from other microorganisms (e.g. *E. coli* and *Z. mobils*) and hyperthermophiles (e.g. *S. solfataricus*, *A. pernix*, *T. brockii* and *T. ethanolicus*) have been considered for large-scale chiral compound biosynthesis. However, low enzymatic activities and dependence on expensive cofactors (e.g. NADP and NADPH) and have been barriers for broad adoption in commercial-scale production processes.

Alcohol dehydrogenases are ubiquitous in three life domains and represent a family of oxidoreductases that catalyze the NAD(P)H-dependent interconversion between alcohols and the corresponding aldehydes or ketones. Interconversions of alcohols, aldehydes, and ketones are essential processes in both prokaryotes and eukaryotes. Among ADHs, the medium chain ADHs have been studied extensively, which usually contain zinc. Zinc-containing ADHs constitute a large protein family with various enzyme activities, including alcohol dehydrogenase, polyol dehydrogenase and cinnamyl alcohol dehydrognease activities. A large number of zinc-containing ADHs including those from the hyperthermophiles *Pyrococcus horikoshii*, *Aeropyrum pernix* and *Sulfolobus solfataricus*, contain one catalytic zinc and one structural zinc (Esposito et al. 2002; Guy et al. 2003; Ishikawa et al. 2007). The zinc-containing ADHs from mesophile *Clostridium beijerinckii*, and thermophiles *Thermoanaerobacter brockii* and *Thermoanaerobacter ethanolicus* contain only catalytic zinc.

Hyperthermophiles are a group of microorganisms growing optimally at ≧80° C., of which anaerobic heterotrophs have attracted increasing attention for use in fermentation reactions at elevated temperatures. All members of genus *Thermococcus* are chemoorganotrophs which can grow on peptide-containing substrates, and some of them are able to grow on carbohydrates including starch and chitinas as carbon source. It is demonstrated that glycolysis from glucose to pyruvate in *Thermococcus celer* and *Thermococcus litoralis*, which appears to occur via a modified EM pathway containing ADP-dependent hexose kinase and phosphofructokinase, and a tungsten-containing glyceraldehyde-3-phosphate: ferredoxin oxidoreductase. Among *Thermococcus* species, *Thermococcus* strain ES1 was firstly reported to produce ethanol under $S^0$-limiting conditions (Ma et al. 1995). Moreover, other ADHs have been purified and characterized, all of which are iron-containing (Antoine et al. 1999; Li and Stevenson 1997; Ma et al. 1994; Ma et al. 1995).

In addition to interests in their physiological roles in production of alcohols, zinc-containing ADHs from hyperthermophiles are highly desired as promising catalysts in industrial applicaitons because of the features such as solvent tolerance, stereoselectivity as well as thermostability. In hyperthermophilic archaea, the zinc-containing ADHs from aerobic archaea *S. solfataricus* and *A. pernix* have been extensively studied in terms of structure, catalysis, function or regulation. It is known that a zinc-containing ADH from anaerobic archaeon *Pyrococcus furiosus* underwent asymmetric ketone reduction to the corresponding chiral alcohols. The crystal structure of a zinc-containing ADH from *P. horikoshii* has been resolved recently. However, no zinc-containing ADHs from *Thermococcus* species have been previously reported.

BRIEF DESCRIPTION OF THE PRIOR ART

The following is a brief description of prior art disclosing thermophilic microorganisms or alcohol dehydrogenase enzymes, in order to provide some background information to supplement the present disclosure. The following is not an admission that any of the prior art disclosed is pertinent to the patentability of the present invention.

WO/2008/053353, entitled "Energy production with hyperthermophilic organisms", discloses the use of hyperthermophilic organisms to produce heat from a biomass. *Thermococcus guaymasensis* is mentioned in the description but there is no mention of alcojol dehydrogenase enzymes.

U.S. Pat. No. 6,737,257, entitled "Hyperthermophilic enzymes for industrial chemical redox reations: a method for biofuel ethanol production", discloses the use of glucose dehydrogenase and alcohol dehydrogenase of *S Solfataricus* in producing and recovering ethanol.

WO 1999/021971, entitled "Thermostable alcohol dehydrogenases", discloses an alcohol dehydrogenase enzyme extracted from *T. brockii*. This enzyme is known to have problems relating to oxygen sensitivity and high production of lactate by *T. brockii*.

U.S. Pat. No. 5,908,924, entitled "Cloning and expression of the gene encoding *thermoanaerobacter ethanolicus* 39E secondary-alcohol dehydrogenase and enzyme biochemical characterization", discloses a secondary alcohol dehydrogenase enzyme extracted from *T. ethanolicus* (ATCC 33223).

US 2008/0220487, entitled "Molecular design of thermostable alcohol dehydrogenase for synthesis for chiral aromatic alcohols", discloses the use of a specific region of an alcohol dehydrogenase in biosynthesizing chiral specific (S-configured) molecules (sequence based on *T. ethanolicus* ADH).

WO 2008/095896, entitled, "Process for the recovery of butanol", WO 2008/080124, entitled "Butanol Production by metabolically engineered yeast" and WO 2008/074794, entitled "Butanol production in a prokaryotic cell", disclose the use of C beijerinckii and its ADH in butanol production.

US 2008/0216181, entitled "Novel Alcohol dehydrogenases" claims certain specific alcohol dehydrogenase sequences, does not specify species.

Canganella et al., "Microbial characterization of thermophilic archaea isolated from the Guaymas basin hydrothermal vent" (Curr Microbiol, 28:299-306, 1994) describes the initial discovery of *Thermococcus guaymasensis*.

Canganella et al., "Biochemical and phylogenetic characterization of two novel deep-sea *Thermococcus* isolates with potentially biotechnological applications" (Arch Microbiol, 167: 233-238, 1997) describes some initial characterization of *Thermococcus guaymasensis* (refered to as "TYS").

Canganella et al, "*Thermococcus guaymasensis* and *Thermococcus aggregans*, two novel thermophilic archaea isolated from the Guaymas Basin hydrothermal vent site" (Int. J. Syst. Bacteriol. 1998. 48:1181-1185) describe further characterization of *Thermococcus guaymasensis* A native strain of this microorganism was deposited at DSMZ (DSM 11113™) and Japan Collection of Microorganisms (JCM 10136™) and represents prior art.

There is a need for improved means of making chiral molecules in general and, in particular, stereospecific chiral molecules. Although biocatalysts are an attractive target, their practical utility has been limited by such factors as instability at elevated temperatures, low yield, low enzymatic activity, and the need for continual supplementation with expensive cofactors in order to maintain enzyme activity. It is, therefore, desirable to provide new biocatalysts useful in the manufacture of chiral molecules as well as other applications.

SUMMARY OF THE INVENTION

We purified an alcohol dehydrogenase (TgADH) from hyperthermophilic archaeon *Thermococcus guaymasensis* to homogeneity and found it to be a homotetramer with a subunit size of 40±1 kDa. The gene encoding the enzyme was cloned and sequenced (SEQ ID NO:1), and the deduced amino acid sequence (SEQ ID NO:2) was found to have significant sequence homology to zinc-containing ADHs and L-threonine dehydrogenases with both binding motifs of catalytic zinc and NADP$^+$. The enzyme was assayed and confirmed to have activity as a primary-secondary ADH and exhibited a substrate preference for secondary alcohols and corresponding ketones.

The TgADH gene encodes a precursor polypeptide, which is processed by cleavage of the N-terminal methionine (M) residue to provide the mature native TgADH polypeptide sequence (SEQ ID NO: 4) of 364 amino acids. The native TgADH protein is encoded by the polynucleotide described in SEQ ID NO:3. Sequence analysis indicates that the mature native TgADH has the following features: a conserved catalytic zinc domain at residues 63-77, $G_{63}H_{64}E_{65}AVG_{68}EVVEVG_{74}SHV_{77}$ (SEQ ID NO: 23); a cysteine $C_{39}$ that is involved in the catalytic site; a putative conserved NADP-binding domain at residues 184-189: $G_{184}IG_{186}PVG_{189}$ (SEQ ID NO: 24), and a sequence which appears to be unique to TgADH at residues 119 to 124: $P_{119}L_{120}K_{121}E_{122}G_{123}G_{124}$ (SEQ ID NO: 25). We also made a recombinant TgADH construct for expressing TgADH in heterologous systems; the sequence of the coding region for this construct is shown in SEQ ID NO:7, and the deduced amino acid sequence is shown in SEQ ID NO:8. The recombinant enzyme was soluble and demonstrated activity similar to the native enzyme.

Site-directed mutagenesis was used to substitute the cysteine residue corresponding to position 56 of the mature TgADH with a serine, to provide the TgADH(C56S) mutant (having amino acid sequence SEQ ID NO:6, encoded by polynucleotide sequence SEQ ID NO:5), and made recombinant constructs for expressing the mutant (the coding region of the recombinant construct is shown in SEQ ID NO:9, and the deduced amino acid sequence is shown in SEQ ID NO:10).

Thus, in a first aspect, the present invention provides an isolated polypeptide selected from the group consisting of:
(a) a polypeptide comprising an amino acid sequence as set forth in SEQ ID NO: 2, 4, 6, 8, or 10;

(b) fragments or derivatives of the polypeptide of (a) having catalytic activity;
(c) fragments of the polypeptide of (a) comprising at least 18, at least 20, at least 25, or at least 30 contiguous amino acids from SEQ ID NO: 2, 4, or 6 or the alcohol dehydrogenase enzyme portion of SEQ ID NO:8 or 10;
(d) fragments of the polypeptide of (a) comprising a catalytic zinc binding motif sequence and/or a cofactor binding motif sequence and/or a cysteine residue at a position corresponding to position 39 in SEQ ID NO:4;
(e) fragments of the polypeptide of (a) comprising
   (i) residue(s) 63 to 77 and/or 184 to 189 and/or 39 of SEQ ID NO:4;
   (ii) residue(s) 64 to 78 and/or 185 to 189 and/or 40 of SEQ ID NO:2 or 6; or
   (iii) residue(s) 116 to 130 and/or 237 to 241 and/or 92 of SEQ ID NO: 8 or 10; and having catalytic activity;
(f) fragments of the polypeptide of (a) comprising SEQ ID NOS: 23 and 24 and having catalytic activity;
(g) fragments of the polypeptide of (a) comprising SEQ ID NO: 25;
(h) a polypeptide comprising:
   (i) from about residues 63 to 77 and from about residues 184 to 189 and residue 39 of SEQ ID NO:4;
   (ii) from about residues 64 to 78 and from about residues 185 to 189 and residue 40 of SEQ ID NO:2 or 6; or
   (iii) from about residues 116 to 130 and from about residues 237 to 241 and residue 92 of SEQ ID NO: 8 or 10;
(i) fragments of the polypeptide of (a) comprising cysteine residues at positions corresponding to Cys39, Cys56, Cys213 and Cys306 in SEQ ID NO:4;
(j) amino acid sequences comprising at least 10 contiguous amino acids and sharing amino acid identity with the amino acid sequences of (a)-(i), wherein the percent amino acid identity is selected from the group consisting of at least 80%, at least 85%, at least 90%, at least 95%, at least 97.5%, at least 99%, and at least 99.5%.

In another aspect, the present invention provides an isolated polynucleotide encoding a polypeptide of as described above.

In another aspect, the present invention provides an isolated nucleic acid molecule, or a fragment, variant or derivative thereof, selected from the group consisting of:
(a) a nucleic acid comprising a nucleotide sequence selected from the group consisting of SEQ ID NOS: 1, 3, 5, 7, and 9 and sequences complementary thereto;
(b) a nucleic acid comprising a nucleotide sequence at least 70% identical to a nucleotide sequence selected from the group consisting of SEQ ID NOS: 1, 3, 5, 7, and 9 and sequences complementary thereto;
(c) a nucleic acid comprising a nucleotide sequence at least 90% identical to a nucleotide sequence selected from the group consisting of SEQ ID NOS: 1, 3, 5, 7, and 9 and sequences complementary thereto;
(d) a nucleic acid comprising a nucleotide sequence at least 99% identical to a nucleotide sequence selected from the group consisting of SEQ ID NOS: 1, 3, 5, 7, and 9 and sequences complementary thereto; and (e) a nucleic acid comprising at least 30 contiguous nucleotides of a nucleotide sequence selected from the group consisting of SEQ ID NOS: 1, 3, 5, 7, and 9 and sequences complementary thereto; and
(f) a nucleic acid capable of hybridizing to the nucleic acid of any one of (a) to (e) under conditions that are moderately or highly stringent.

In another aspect, the present invention provides a vector (e.g. an expression vector) comprising an isolated nucleic acid molecule as described above.

In another aspect, the present invention provides a host cell comprising the isolated nucleic acid molecule or vector described above.

In another aspect, the present invention provides a method of preparing the polypeptide of the invention, as described above, said method comprising:
(a) culturing the host cell described above under conditions suitable for expression of the polypeptide; and
(b) recovering the polypeptide so expressed.

In another aspect, the present invention provides a transgenic organism comprising the nucleic acid described above.

In another aspect, the present invention provides a stereoselective method of synthesizing a product, said method comprising:
(a) contacting a substrate with an isolated polypeptide of claim 1 having catalytic activity;
(b) incubating under suitable reaction conditions; and
(c) recovering the synthesized product.

In embodiments of this method, the substrate is a primary or secondary alcohol and the reaction is an oxidation reaction, or the substrate is a corresponding ketone or alhehyde and the reaction is a reduction reaction.

The pET30a-TgADH-w expression construct (for expressing the wild-type TgADH) was transformed into expression host *E. coli* strain BL21 codon plus RIL. A sample of the transformed cells thereby obtained was deposited on Sep. 22, 2009 with the International Depositary Authority of Canada (International Depositary Authority of Canada, National Microbiology Laboratory, Public Health Agency of Canada, 1015 Arlington St., Winnipeg, Manitoba, Canada R3E 3R2) and assigned accession number 220909-01. Thus, the present invention provides a cell or cells deposited under accession number 220909-01 or cultured directly or indirectly therefrom, as well as any TgADH polypeptides produced by culturing such cells, any pET30a-TgADH-w expression construct obtained by culturing such cells and any portion thereof, including any cDNA encoding TgADH or any portion thereof obtained by culturing such cells.

The pET30a-TgADH-m1 expression construct (for expressing the TgADH(C56S) mutant) was transformed into host *E. coli* strain rosetta-2. A sample of the transformed cells thereby obtained was deposited on Sep. 22, 2009 with the International Depositary Authority of Canada (International Depositary Authority of Canada, National Microbiology Laboratory, Public Health Agency of Canada, 1015 Arlington St., Winnipeg, Manitoba, Canada R3E 3R2) and assigned the accession number 220909-02. Thus, the present invention provides a cell or cells deposited under accession number 220909-01 or cultured directly or indirectly therefrom, as well as any TgADH(C56S) polypeptides produced by culturing such cells, any pET30a-TgADH-m-1 expression construct obtained by culturing such cells and any portion thereof, including any cDNA encoding TgADH(C56S) or any portion thereof obtained by culturing such cells.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 1 shows the full-length nucleotide sequence of the wild-type TgADH gene (SEQ ID NO: 1) including the codon for the N-terminal residue M (which is cleaved in the native polypeptide), which has a total of 1098 bp including start codon ATG (italics) and stop codon TGA (italics). The sequence is 1095 without the stop codon, however, the stop codon is typically included in the full-length nucleotide sequence. The codon "TGT" coding for $C_{56}$ in the wild-type polypeptide is shown in bold. This is the site of mutation in the TgADH(C56S) mutant of FIG. 10. The codon $A_1GC$ encodes the serine residue corresponding to the the first amino acid in the native TgADH sequence.

FIG. 2 shows the 365 amino acid precursor polypeptide (SEQ ID NO: 2) encoded by the nucleotide of FIG. 1 (SEQ ID NO:1). Note that this sequence differs from that of the native enzyme, in that the first amino acid M in the sequence SEQ ID NO:2 is absent in the native polypeptide of 364 amino acid residues shown in FIG. 4 (SEQ ID NO:4). The amino acid $S_1$ corresponds to the first amino acid in the native TgADH sequence.

FIG. 3 shows the nucleotide sequence (SEQ ID NO:3) encoding the wild-type TgADH protein (i.e. the mature form of the enzyme, which lacks the N-terminal residue M of the precursor polypeptide), which has a total of 1095 bp including the stop codon TGA (italics). The codon $A_1GC$ encodes the serine residue corresponding to the the first amino acid in the native sequence.

FIG. 4 shows the mature native TgADH polypeptide sequence (SEQ ID NO: 4) of 364 amino acids, (i.e. the mature form of the enzyme, in which the first amino acid residue, M, of the full-length precursor polypeptide has been removed). The amino acid $S_1$ is the first amino acid in the native TgADH sequence. A conserved catalytic zinc domain is shown as residues 63-77: $G_{63}H_{64}E_{65}AVG_{68}EVVEVG_{74}SHV_{77}$ (SEQ ID NO: 23). Cysteine $C_{39}$ is involved in the catalytic site. A putative conserved NADP-binding domain is shown at residues 184-189: $G_{184}IG_{186}PVG_{189}$ (SEQ ID NO: 24). A sequence which appears to be unique to TgADH is shown at residues 119 to 124: $P_{119}L_{120}K_{121}E_{122}G_{123}G_{124}$ (SEQ ID NO: 25).

FIG. 5 shows the full-length nucleotide sequence of the TgADH(C56S) mutant (SEQ ID NO: 5) including the coding sequence for the N-terminal residue, M, of the precursor polypeptide encoded by the full-length TgADH gene and has a total of 1098 p (including start codon ATG and stop codon TGA, which are italicized); The mutated codon, AGC, is shown in bold and underline. The codon $A_1GC$ encodes the serine residue corresponding to the first amino acid in the native sequence, and indicates the beginning of the ADH enzyme encoding region.

FIG. 6 shows the amino acid sequence of the TgADH (C56S) mutant polypeptide (SEQ ID NO: 6) including N-terminal residue M and has a total 356 amino acid residues. The mutated C56S amino acid residue is shown in bold and underline. The amino acid $S_1$ corresponds to the first amino acid in the native TgADH sequence, and indicates the beginning of the ADH enzyme region.

FIG. 7 shows nucleotide sequence of the recombinant wild-type TgADH gene (SEQ ID NO:7), which includes the N-terminal residue M of the polypeptide encoded by the full-length TgADH gene and part of the vector sequence and has a total of 1254 bp (including start codon ATG and stop codon TGA shown in Italics, with the 156 bp sequence added from the vector shown in Bold and underlined at the beginning of the sequence). The recombinant wild type TgADH was expressed in E. coli strain BL21-codon plus RIL with vector pET30a. The vector sequence encodes a His tag ($H_6$), such that the recombinant enzyme can be easily purified after expression using an affinity Nickel column (one-step purification). The codon $A_1GC$ encodes the serine residue corresponding to the the first amino acid in the native TgADH sequence, and indicates the beginning of the ADH enzyme coding region.

FIG. 8. shows the amino acid sequence of the recombinant wild-type TgADH polypeptide (SEQ ID NO: 8) encoded by the recombinant wild-type TgADH nucleotide of SEQ ID NO: 7 including the vector coding region, which results in a sequence of 417 amino acids. The first 52 amino acids are from the vector and are shown in bold and underlined at the beginning of the sequence. The amino acid $S_1$ corresponds to the first amino acid in the native TgADH sequence, and indicates the beginning of the ADH enzyme region.

FIG. 9 shows the nucleotide sequence of a TgADH(C56S) mutant gene (SEQ ID NO: 9) which includes the N-terminal residue M of the polypeptide encoded by the full-length TgADH gene and part of the vector sequence and has a total of 1254 bp (including start codon ATG and stop codon TGA shown in Italics, with the 156 bp sequence added from the vector shown in bold and underlined at the beginning of the sequence). The recombinant mutant TgADH(C56S) was expressed in E. coli strain Rosetta-2 with vector pET30a. The vector sequence encodes a His tag ($H_6$), such that the recombinant enzyme can be easily purified after expression using an affinity Nickel column (one-step purification). The codon $A_1GC$ encodes the serine residue corresponding to the the first amino acid in the native sequence and indicates the beginning of the ADH enzyme coding region.

FIG. 10 shows the 417 amino acid sequence of the TgADH (C56S) mutant polypeptide (SEQ ID NO:10) encoded by the nucleotide of SEQ ID NO: 9 (the 52 amino acids added from the vector are shown in bold and underlined at the beginning of the sequence). Note that there was the only amino acid substitution made in the mutant was a substitution of serine for the cysteine at postion 56 in the native TgADH. The amino acid $S_1$ corresponds to the first amino acid in the native TgADH sequence, and indicates the beginning of the ADH enzyme region.

FIG. 14 Alignment of sequence of T. guaymasensis ADH and other related zinc-containing ADHs. The sequences were aligned using Clustal W (Thompson et al. 1994). The amino acids highlighted with light shadow are putative binding sites of catalytic zinc. Amino acids highlighted in dark shadow are a putative motif of cofactor binding. TgADH, T. guaymasensis ADH; TbADH, T. brockii ADH; CbADH, C. beijerinckii ADH. "*": residues or nucleotides that are identical in all sequences in the alignment; ":", conserved substitutions; ".", semi-conserved substitutions; "-", no corresponding amino acid.

FIG. 15. Amino acid sequence alignment of alcohol dehydrogenases from *T. guaymasensis* (TgADH), *T. brockii* (TbADH), and *C. beijerinckii* (CbADH). The sequences were aligned using Clustal W (Thompson et al. 1994) with subsequent manual adjustments. Amino acid residues of TgADH are in the one-letter code. The underlined letters represent amino acid residues on which site-directed mutagenesis experiments have been performed (Bogin et al. 1998; Bogin et al. 2002; Goihberg et al. 2007; Musa et al. 2007; Phillips 2002). Symbols used: "*", residues or nucleotides that are identical in all sequences in the alignment; ":", conserved substitutions; ".", semi-conserved substitutions; "-", identical amino acid; blank, no corresponding amino acid.

DEFINITIONS

Figure 11:
FIG. 11. shows the predicted tertiary structure of TgADH monomer. Each monomer has one putative NADP-binding site and one putative zinc-binding site (not indicated). Although each monomer is expected to have catalytic activity, in the native state, four monomers associate to form a homotetramer.

To facilitate an understanding of the present invention, a number of terms and phrases as used herein are defined below:

As used herein, terms defined in the singular are intended to include those terms defined in the plural and vice versa.

The use of the article "a" or "an" is intended to include one or more.

As used herein, a "catalyst" refers to a substance that, when added to a reaction mixture, changes (e.g. speeds up) the rate of attainment of equilibrium in the system without itself undergoing a permanent chemical change.

As used herein, a "biocatalyst" refers to a catalyst, such as an enzyme, that may be used to perform transformations on organic compounds. The term biocatalyst may encompass isolated or purified enzymes or enzymes still residing in living cells, such as microorganisms.

As used herein, a "stereoisomer", refers to the isomers of molecules that have the same molecular formula and sequence of bonded atoms (constitution) but differ in the three-dimentional orientations of their atoms in space (e.g. L-alanine and D-alanine).

As used herein, a "chiral molecule" or "chiral compound" refers generally to a molecule that is non-superimposable on its mirror image. A chiral molecule has at least one chiral centre (a stereocenter), commonly a carbon atom with four different substituents, which results in stereoisomers that are configurational isomers, meaning isomers that cannot be converted from one into another by rotations about single bonds in the molecules.

A "chiral catalyst" is one that can direct the stereochemistry of the substrates in the reactions it catalyzes. Many biocatalysts are chiral catalysts, demonstrating chiral substrate specificity and/or directing asymmetric catalysis.

As used herein, an "enantiomer" refers to the two configurational isomers (R and S) of a chiral molecule having one chiral center. Enantiomers are non-superimposable mirror images of each other. Enantiomers have identical physical properties, such as melting points and boiling points, and also have identical spectroscopic properties. Each enantiomer will rotate light in a different sense, clockwise or counterclockwise, and thus enantiomers are aslo refered to as optical isomers. Enantiomers of biological molecules typically differ with respect to biological activity.

As used herein, a "diastereomer" refers to a pair of isomers of a chiral molecule that are not mirror images of one another. Diastereomers result, for example, when a chiral molecule has more than one one stereocenter. Diasteriomers can have different physical properties and reactivities.

The term "stereoisomer", when used in connection with chiral molecules, may include "enantiomers" or "diastereomers" depending on the molecule. The terms "chiral molecule", "chiral compound", "stereoisomer", "enantiomer" and "diastereomer" may be used interchangeably herein.

As used herein, the term "racemic mixture" refers to a mixture of two enantiomers of a chiral compound. An racemic mixture typically comprises substantially 50:50 of both enantiomers of a compound such that the optical rotation of the (+) enantiomer cancels out the optical rotation of the (−) enantiomer.

As used herein, the term "substantially pure enantiomer" or "substantially purified enantiomer" refers to a compound, substance or preparation (e.g. which may be derived from non-optically active starting material, substrate, or intermediate) wherein one enantiomer is significantly enriched over the other enantioner, for example, wherein the other enantiomer represents less than 20%, less than 10%, less than 5%, less than 2%, less than 1%, or theoretically even 0% of the enantiomers present in the compound, substance or preparation.

As used herein, "enantiopure" refers to a compound, substance or preparation that comprises a substantially pure enantioner.

As used herein, "enantioenriched" refers to a compound, substance or preparation that comprises an enantiomeric excess of one enantiomer over the other enantioner, or exrpressed another way, wherein one enantioner represents a major enantioner (greater than 50%) in the compound, substance or preparation, for example, the major enantiomer may 60%, 70%, 80%, 90%, 92%, 95%, 98%, 99%, or theoretically even 100% of an enantioner pair.

As used herein, the phrase "enantiomeric excess" or "e.e." refers to a reaction product wherein one enantiomer is produced in excess of the other and the percentage of the excess enantiomer is calculated using either (or both) of the following algorithms:

Algorithm No. 1: enantiomeric excess=(specific rotation of the reaction product/specific rotation of the pure enantiomer in excess)*100.

Algorithm No. 2: enantiomeric excess=(moles of major enantiomer-moles of other enantiomer/total moles of both enantiomers)*100.

When referring to an enantiomer compound, substance or preparation, either or both of the percent of the major enantiomer (e.g. by weight) and/or the percent enantiomeric excess of the major enantiomer may be used to determine whether the preparation represents a substantially purified enantiomer preparation.

As used herein, the term "optical purity" refers to the ratio of the observed optical rotation of a sample consisting of a mixture of enantiomers to the optical rotation of one pure enantiomer.

The term "stereomeric excess" refers to chiral chemical reactions wherein chiral product(s), such as enantiomers or diastereomers, are obtained in excess of the other stereoisomers.

A stereoselective reaction may also be referred to as "asymmetric catalysis".

As used herein, "substrate", as in a biocatalytic reaction, refers to a chemical entity whose conversion to a "product" or "products" is catalyzed by one or several enzymes.

As used herein, "nicotinamide adenine dinucleotide phosphate" ($C_{21}H_{29/30}N_7O_{17}P_3$) or "NADP", NADP+" or "NADPH" refers in general to a ubiquitous redox cofactor that functions as a carrier of electron pairs for redox reactions. The oxidized form of the cofactor is carries a positive charge, and is denoted NADPH+ while the reduced form is NADPH. A related cofactor is "nicotinamide adenine dinucleotide" or "NAD", "NAD+" or "NADH".

As used herein, a "reducing agent" refers to any of a variety of reagents that are utilized as a hydrogen donating source in the reduction of ketones to alcohols. In preferred embodiments, proteins disclosed herein catalyze the reduction of ketones to alcohols using NADPH as a hydrogen donating source; thus, NADPH is a reducing agent. It is understood that the reducing agent may added to a reaction or may be generated in situ under the conditions of a particular chemical reaction. For example, in one embodiment of the invention, the reaction mixture contains isopropanol that is used both as a solvent and as a substrate to recycle the cofactor. Other examples of reducing agents include, but are not limited to NADH, FADH, FADH2, sodium borohydride, lithium aluminum hydride and the like.

As used herein, an oxidizing agent refers to any of a variety of reagents that are utilized as a hydrogen abstraction source in the oxidation of alcohols to ketones. In preferred embodiments, proteins disclosed herein catalyze the oxidation of alcohols to ketones using NADP+ as a hydrogen abstraction source from the alcohol in oxidation to the ketone; thus, NADP+ is an oxidizing agent. It is understood that the reducing agent may be generated in situ under the conditions of a particular chemical reaction. Other examples of reducing agents include, but are not limited to NAD+, FADH, FAD+, potassium chromate, potassium permanganate, and the like.

As used herein, the term "microorganism" refers to any species or type of microorganism, including but not limited to, bacteria, archaea, fungi, protozoans, mycoplasma, and parasitic organisms.

The terms "bacteria" and "bacterium" refer to all prokaryotic organisms belong to the domain of Bacteria, including those within all of the phyla in the Kingdom Procaryotae. It is intended that the terms encompass all microorganisms considered to be bacteria, for example, Pseudomonas sp., Mycoplasma, Chlamydia, Actinomyces, Streptomyces, and Rickettsia. All forms of bacteria are included within this definition including cocci, bacilli, spirochetes, spheroplasts, protoplasts, etc. Also included within this term are prokaryotic organisms which are gram negative or gram positive. Archaea are also prokaryotes belong to the Domain of Archaea, such as methanogens, *Thermococcus, Pyrococcus*.

The term "mesophile" refers to an organism that grows best in moderate temperature environments, typically between about 25° C. and 40° C. *Escherichia coli* is an example of a mesophile.

The terms "thermophile" and "hyperthermophile" refer to organisms that can grow in high or extreme temperature environments (e.g. higher than 50° C., and more typically higher than 70 C., higher than 80 C., higher than 90° C., and sometimes higher than 100° C.). Thermophiles generally thrive at lower temperatures than hyperthermophiles and the terms may be used interchangeably herein to distinguish from mesophiles. The genome and proteome composition of thermophiles are characterized by overrepresentation of purine bases in protein coding sequences, higher GC-content of structural RNAs, distinct synonymous codon usage, enhanced usage of positively charged residues and aromatic residues, and a decrease in polar uncharged residues in the encoded protein. *Thermococcus guaymasensis* (Tg) is an example of a hypothermophile.

As used herein, the terms "contacting" and "contacted," refer to bringing one or more of the compositions of the present invention into contact with a substrate or a sample comprising potential substrates for reacting with the catalytic sites of enzymes or active polypeptides thereof of the present invention. Compositions of the present invention may react with the contacted substrates for providing reacted products. The present invention contemplates that the disclosed compositions are contacted with the substrates or samples comprising potential substrates in sufficient volumes and/or concentrations to react with the catalytic site.

As used herein, the term "incubating" in reference to a contacted enzyme and substrate, refers to maintaining a chemical or biochemical system under specific conditions, such a temperature and/or pressure and/or substrate or product concentration, in order to promote a particular reaction product.

The term "gene" encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region termed "exon" or "expressed regions" or "expressed sequences" interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "nucleic acid sequence," "nucleotide sequence of interest" or "nucleic acid sequence of interest" refers to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, disease resistance genes, growth factors, etc.), and non-coding regulatory sequences which do not encode an mRNA (e.g., promoter sequence, polyadenylation sequence, termination sequence, enhancer sequence, etc.).

The term "oligonucleotide" refers to a molecule comprised of two or more deoxyribonucleotides or ribonucleotides, preferably more than three, and usually more than ten. The exact size will depend on many factors, which in turn depend on the ultimate function or use of the oligonucleotide. The oligonucleotide may be generated in any manner, including chemical synthesis, DNA replication, reverse transcription, or a combination thereof.

The term "polynucleotide" refers to a molecule comprised of several deoxyribonucleotides or ribonucleotides, and is used interchangeably with oligonucleotide. Typically, oligonucleotide refers to shorter lengths, and polynucleotide refers to longer lengths, of nucleic acid sequences.

The term "an oligonucleotide (or polypeptide) having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in a cDNA, genomic DNA, or RNA form. When present in a DNA form, the oligonucleotide may be single-stranded (i.e., the sense strand) or double-stranded. Suitable control elements such as enhancers/promoters, splice junctions, polyadenylation signals, etc., may be placed in close proximity to the coding region of the gene if needed to permit proper initiation of transcription and/or correct processing of the primary RNA transcript. Alternatively, the coding region utilized in the expression vectors of the present invention may contain endogenous enhancers, exogenous promoters, splice junctions, intervening sequences, polyadenylation signals, etc., or a combination of both endogenous and exogenous control elements.

The term "substantially identical" or homologous or similar varies with the context as understood by those skilled in the relevant art and generally means at least at least 70%, preferably at least 80%, 85%, 90, 92% 95%, 98% or 99% sequence identity. The terms "homology" and "identity" are often used interchangeably. In general, sequences are aligned so that the highest order match is obtained. Examples of algorithm that is suitable for determining percent sequence identity and sequence similarity is algorithms such as the BLAST algorithm, as is well known to those skilled in the art. Software for performing BLAST analyses is publicly available through the National Center for Biotechnology Information. Other commercially or publicly available programs include, DNAStar "MegAlign" program (Madison, Wis.) and the University of Wisconsin Genetics Computer Group (UWG) "Gap" program (Madison Wis.)).

By sequence identity, the number of conserved amino acids are determined by standard alignment algorithms programs, and are used with default gap penalties established by each supplier. Substantially identical nucleic acid molecules would hybridize typically at moderate stringency or at high stringency all along the length of the nucleic acid or along at least about 70%, 80% or 90% of the full length nucleic acid molecule of interest. Also contemplated are nucleic acid molecules that contain degenerate codons in place of codons in the hybridizing nucleic acid molecule.

Therefore, as used herein, the term "identity" represents a comparison between a test and a reference polypeptide or polynucleotide.

As used herein, the term at least "90% identical to" would refer to percent identities from 90 to 99.99 relative to the reference polypeptides. Identity at a level of 90% or more is indicative of the fact that, assuming for exemplification purposes a test and reference polynucleotide length of 100 amino acids are compared. No more than 10% (i.e., 10 out of 100) amino acids in the test polypeptide differs from that of the reference polypeptides. Similar comparisons can be made between a test and reference polynucleotides. Such differences can be represented as point mutations randomly distributed over the entire length of an amino acid sequence or they can be clustered in one or more locations of varying length up to the maximum allowable, e.g. 10/100 amino acid difference (approximately 90% identity). Differences are defined as nucleic acid or amino acid substitutions, or deletions. At the level of homologies or identities above about 85-90%, the result should be independent of the program and gap parameters set; such high levels of identity can be assessed readily, often without relying on software.

As used herein, primer refers to an oligonucleotide containing two or more deoxyribonucleotides or ribonucleotides, typically more than three, from which synthesis of a primer extension product can be initiated. Experimental conditions conducive to synthesis include the presence of nucleoside triphosphates and an agent for polymerization and extension, such as DNA polymerase, and a suitable buffer, temperature and pH.

As used herein, "domain" refers to a portion of a molecule, e.g., proteins or the encoding nucleic acids, that is structurally and/or functionally distinct from other portions of the molecule.

As used herein, functional "activity" refers to a polypeptide or portion thereof that displays one or more activities associated with a full-length or mature protein. Functional activities include, but are not limited to, biological activity, catalytic or enzymatic activity, antigenicity (ability to bind to or compete with a polypeptide for binding to an anti-polypeptide antibody), immunogenicity, ability to form multimers, the ability to specifically bind to a receptor or ligand for the polypeptide. In particular herein, functional activity refers to catalytic or enzymatic activity.

As used herein, derivative or analog of a molecule refers to a portion derived from or a modified version of the molecule.

As used herein: stringency of hybridization in determining percentage mismatch is as follows:

1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

Those of skill in this art know that the washing step selects for stable hybrids and also know the ingredients of SSPE. SSPE is pH 7.4 phosphate-buffered 0.18 NaCl. Further, those of skill in the art recognize that the stability of hybrids is determined by $T_m$, which is a function of the sodium ion concentration and temperature ($T_m = 81.5°$ C.$-16.6$ ($\log_{10}[Na^+]$)+ 0.41 (% G+C)−600/l)), so that the only parameters in the wash conditions critical to hybrid stability are sodium ion concentration in the SSPE (or SSC) and temperature.

It is understood that equivalent stringencies can be achieved using alternative buffers, salts and temperatures. By way of example and not limitation, procedures using conditions of low stringency are as follows (see also Shilo and Weinberg, *Proc. Natl. Acad. Sci. USA* 78:6789-6792 (1981)): Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA (10×SSC is 1.5 M sodium chloride, and 0.15 M sodium citrate, adjusted to a pH of 7).

Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ cpm $^{32}$P-labeled probe is used. Filters are incubated in hybridization mixture for 18-20 hours at 40° C., and then washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Filters are blotted dry and exposed for autoradiography. If necessary, filters are washed for a third time at 65-68° C. and reexposed to film. Other conditions of low stringency which can be used are well known in the art (e.g., as employed for cross-species hybridizations).

By way of example and not way of limitation, procedures using conditions of moderate stringency include, for example, but are not limited to, procedures using such conditions of moderate stringency are as follows: Filters containing DNA are pretreated for 6 hours at 55° C. in a solution containing 6×SSC, 5× Denhart's solution, 0.5% SDS and 100 µg/ml denatured salmon sperm DNA. Hybridizations are carried out in the same solution and 5-20×10$^6$ cpm $^{32}$P-labeled probe is used. Filters are incubated in hybridization mixture for 18-20 hours at 55° C., and then washed twice for 30 minutes at 60° C. in a solution containing 1×SSC and 0.1% SDS. Filters are blotted dry and exposed for autoradiography. Other conditions of moderate stringency which can be used are well-known in the art. Washing of filters is done at 37° C. for 1 hour in a solution containing 2×SSC, 0.1% SDS.

By way of example and not way of limitation, procedures using conditions of high stringency are as follows: Prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 hours at 65° C. in prehybridization mixture containing 100 µg/ml denatured salmon sperm DNA and 5-20×10$^6$ cpm of $^{32}$P-labeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 minutes before autoradiography. Other conditions of high stringency which can be used are well known in the art.

The terms "complementary" and "complementarity" refer to polynucleotides (i.e., a sequence of nucleotides) related by the base-pairing rules. For example, the sequence "A-G-T-" is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "recombinant" when made in reference to a nucleic acid molecule refers to a nucleic acid molecule that is comprised of segments of nucleic acid joined together by means of molecular biological techniques. The term "recombinant" when made in reference to a protein or a polypeptide refers to a protein molecule that is expressed using a recombinant nucleic acid molecule.

The terms "protein," "polypeptide," "peptide," "encoded product," and "amino acid sequence" are used interchangeably to refer to compounds comprising amino acids joined via peptide bonds and a "protein" encoded by a gene is not limited to the amino acid sequence encoded by the gene, but includes post-translational modifications of the protein. Where the term "amino acid sequence" is recited herein to refer to an amino acid sequence of a protein molecule, the term "amino acid sequence" and like terms such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein. The deduced amino acid sequence from a coding nucleic acid sequence includes sequences that are derived from the deduced amino acid sequence and modified by post-translational processing, where modifications include, but not limited to, the addition of metal ions, glycosylation, hydroxylations, phosphorylations, and amino acid deletions, substitutions, and additions. Thus, an amino acid sequence comprising a deduced amino acid sequence is understood to include post-translational modifications of the encoded and deduced amino acid sequence.

Some embodiments of the present invention provide mutant or variant forms of enzymes described herein. For example, a modified peptide can be produced in which the amino acid sequence has been altered, such as by amino acid substitution, deletion, or addition. For example, it is contemplated that an isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of enzymes described herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (See e.g., Stryer (ed.), Biochemistry, 2nd ed, WH Freeman and Co. [1981]). Whether a change in the amino acid sequence of a peptide results in a functional homolog can be readily determined by assessing the ability of the variant peptide to produce a response in a fashion similar to the wild-type protein using the assays described herein. Peptides in which more than one replacement has taken place can readily be tested in the same manner.

It is possible to modify the structure of a polypeptide having an activity of the enzymes described herein for such purposes as enhancing enzyme activity, decreasing oxygen sensitivity, and the like. Prefered modifications result in variants and mutants have characterizing features that are similar to and/or superior to the native peptides.

As used herein, the term "fusion protein" refers to a chimeric protein containing the protein of interest (i.e., a mutant enzyme or fragments thereof) joined to an exogenous protein fragment, such as a non-enzyme sequence, an enzyme sequence, etc. The fusion partner may provide a detectable moiety, may provide an affinity tag to allow purification of the recombinant fusion protein from the host cell, may provide an additionally enzymatic activity, and the like. If desired, the fusion partner may be removed from the protein of interest by a variety of enzymatic or chemical means known to the art.

The term "isolated" when used in relation to a nucleic acid or polypeptide, as in "an isolated oligonucleotide," refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may be single-stranded), but may contain both the sense and anti-sense strands (i.e., the oligonucleotide may be double-stranded).

The term "purified" refers to molecules, including nucleic or amino acid sequences that are removed from their natural environment isolated or separated. An "isolated nucleic acid sequence" is therefore a purified nucleic acid sequence. "Substantially purified" molecules are at least 60% free, at least 75% free, or at least 90% free from other components with which they are naturally associated. As used herein, the terms "purified" and "to purify" also refer to the removal of contaminants from a sample. The removal of contaminating molecules, including proteins, results in an increase in the percent of polypeptide of interest in the sample. In another example, recombinant polypeptides are expressed in bacteria, yeast, or mammalian host cells and the polypeptides are purified by the removal of host cell proteins; the percent of recombinant polypeptides is thereby increased in the sample.

The terms "in operable combination", "in operable order," and "operably linked" as used herein refer to the linkage of nucleic acid sequences in such a manner that a nucleic acid molecule capable of directing the transcription of a given gene and/or the synthesis of a desired protein molecule is produced.

The term "native" or "wild-type" (which may be abbreviated to "w" or "wt") when made in reference to a gene refers to a gene which has the characteristics of a gene isolated from a naturally occurring source. The term "native" or "wild-type" when made in reference to a gene product refers to a gene product which has the characteristics of a gene product isolated from a naturally occurring source. Herein, the term "native TgADH" or "wild-type TgADH" is used to refer to a polypeptide having the amino acid sequence set forth in SEQ ID NO:4. A wild-type gene is that which is most frequently observed in a population and is thus arbitrarily designated the "normal" or "wild-type" form of the gene. In contrast, the term "modified" or "mutant" or "variant" when made in reference to a gene, respectively, to a gene or to a gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, "engineer," "site-directed mutagenesis," and "directed evolution" refer to a variety of methods for mutating, adding, deleting, or chemically modifying at least one nucleic acid of a sequence that results in substituting at least one amino acid in the expressed protein, methods for which are well known to those of skill in the art.

As used herein, "mutant," "mutation," "mutating," and "mutagenesis" refer to any alteration in a gene from its "natural," "nonmutated," "native" or "wild-type" state.

The term "wild-type" when made in reference to a peptide sequence and nucleotide sequence refers to a peptide sequence and nucleotide sequence, respectively, which has the characteristics of that peptide sequence and nucleotide sequence when isolated from a naturally occurring source. A wild-type peptide sequence and nucleotide sequence is that which is most frequently observed in a population and is thus arbitrarily designated the "normal" or "wild-type" form of the peptide sequence and nucleotide sequence, respectively. In contrast, the term "modified" or "mutant" refers to a peptide sequence and nucleotide sequence which displays modifications in sequence and/or functional properties (i.e., altered characteristics, such as functionally altered and/or functionally inactive) when compared to the wild-type peptide sequence and nucleotide sequence, respectively. It is noted that naturally-occurring mutants can be isolated; these are identified by the fact that they have altered characteristics when compared to the wild-type peptide sequence and nucleotide sequence. Nucleic acid sequences and/or proteins may be modified by chemical, biochemical, and/or molecular biological techniques. Modifications to nucleic acid sequences include introduction of one or more deletion, insertion, and substitution. A "deletion" is defined as a change in a nucleic acid sequence in which one or more nucleotides is absent. An "insertion" or "addition" is that change in a nucleic acid sequence, which has resulted in the addition of one or more nucleotides. A "substitution" results from the replacement of one or more nucleotides by a molecule which is a different molecule from the replaced one or more nucleotides.

For simplicity, we will use the numbering of amino acids in the wild-type TgADH polypeptide, as set forth in SEQ ID NO:4, to describe and identify important residues and mutations in the TgADH enzyme. Thus, for example, the terms "position 56" or "residue 56", refer to the amino acid position 56 in SEQ ID NO: 4, and to corresponding positions in homologous genes or variants when aligned with SEQ ID NO:4. It is understood that homologues or variants may have alignment shifts such that the amino acid of interest does not have the same number as the corresponding amino acid in SEQ ID NO:4. For example, the TgADH(C56S) mutant polypeptide described in SEQ ID NO:10 has a substitution of serine for a cysteine at amino acid position corresponding to position 56 in SEQ ID NO:4, but this residue occurs at position 109 in SEQ ID NO:10.

The chemical terms provided in this application have a variety of synonyms and thus the chemical terms listed in this application are not meant to be limiting descriptions.

The term "alkyl" refers to a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. The term "higher alkyl" has the same meaning as alkyl but contains from 2 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as a "homocycles" or "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

The term "aryl" refers to an aromatic carbocyclic moiety such as phenyl or naphthyl.

The term "heteroaryl" refers to an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

The term "heteroarylalkyl" refers to an alkyl having at least one alkyl hydrogen atom replaced with a heteroaryl moiety, such as —CH2pyridinyl, —CH2pyrimidinyl, and the like.

The term "heterocycle" (also referred to herein as a "heterocyclic ring") refers to a 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "heterocyclealkyl" refers to an alkyl having at least one alkyl hydrogen replaced with a heterocycle, such as —CH2-morpholinyl, and the like.

The term ""methyl secondary alcohol" refers to a hydroxyl-substituted alkyl having a methyl group bound to a carbon with a hydroxyl group, such as —CHOHCH3.

The term "substituted", as used herein, refers to at least one hydrogen atom of a molecular arrangement is replaced with a substituent. With regard to amino acid sequences, a substituted amino acid is intended to include sequences in which an amino acid residue is replaced, deleted, added, or where any of the preceding optionally contains one or more additional substituent(s). In the case of an oxo substituent ("=O"), two hydrogen atoms are replaced. When substituted, one or more of the groups below are "substituents." Substituents within the context of this invention include, but are not limited to, halogen, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocycle, and heterocyclealkyl, as well as, —NRaRb, —NRaC(=O)Rb, —NRaC(=O)NRaNRb, —NRaC(=O)ORb—NRaSO2Rb, —C(=O)Ra, C(=O)ORa, —C(=O)NRaRb, —OC(=O)NRaRb, —ORa, —SRa, —SORa, —S(=O)2Ra, —OS(=O)2Ra and —S(=O)2ORa. In addition, the above substituents may be further substituted with one or more of the above substituents, such that the substituent comprises a substituted alkyl, substituted aryl, substituted arylalkyl, substituted heterocycle, or substituted heterocyclealkyl. Ra and Rb in this context may be the same or different and, independently, hydrogen, alkyl, haloalkyl, substituted alkyl, aryl, substituted aryl, arylalkyl, substituted arylalkyl, heterocycle, substituted heterocycle, heterocyclealkyl or substituted heterocyclealkyl.

The term "unsubstituted", as used herein, refers to any compound that does not contain extra substituents attached to the compound. An unsubstituted compound refers to the chemical makeup of the compound without extra substituents, e.g., the compound does not contain protecting group(s). For example, unsubstituted proline is a proline amino acid even though the amino group of proline may be considered disubstituted with alkyl groups.

The term "about" when used in conjunction with a numeric value is understood to encompass a variance of up to 10% (e.g. +/−10%). Unless where expressed otherwise, or where common knowledge dictates otherwise, the term "about" is understood to precede the numeric values or ranges recited herein.

DETAILED DESCRIPTION

We purified an alcohol dehydrogenase (ADH) from hyperthermophilic archaeon *Thermococcus guaymasensis* to homogeneity and found it to be a homotetramer with a subunit size of 40±1 kDa. The gene encoding the enzyme was cloned and sequenced (SEQ ID NO:1), and the deduced amino acid sequence (SEQ ID NO:2) was found to have significant sequence homology to zinc-containing ADHs and L-threonine dehydrogenases with both binding motifs of catalytic zinc and NADP$^+$. The enzyme was assayed and confirmed to have activity a primary-secondary ADH and exhibited a substrate preference for secondary alcohols and corresponding ketones.

The TgADH gene encodes a precursor polypeptide, which os processed by cleaving the N-terminal methionine (M) residue to provide the mature native TgADH polypeptide sequence (SEQ ID NO: 4) of 364 amino acids. The native TgADH protein is encoded by the polynucleotide described in SEQ ID NO:3. Sequence analysis indicates that the mature native TgADH has the following features: a conserved catalytic zinc domain at residues 63-77, $G_{63}H_{64}E_{65}AVG_{68}EVVEVG_{74}SHV_{77}$ (SEQ ID NO: 23); a cysteine $C_{39}$ that is involved in the catalytic site; a putative conserved NADP-binding domain at residues 184-189: $G_{184}1G_{186}PVG_{189}$ (SEQ ID NO: 24), and a sequence which appears to be unique to TgADH at residues 119 to 124: $P_{119}L_{120}K_{121}E_{122}G_{123}G_{124}$ (SEQ ID NO: 25). We also made a recombinant TgADH constructs for expressing TgADH in heterologous systems; the sequence of the coding region for this construct is shown in SEQ ID NO:7, and the deduced amino acid sequence is shown in SEQ ID NO:8. The recombinant enzyme was soluble and demonstrated activity similar to the native enzyme.

Site-directed mutagenesis was used to substitute the cysteine residue corresponding to position 56 of the mature TgADH with a serine, to provide the TgADH(C56S) mutant (having amino acid sequence SEQ ID NO:6, encoded polynucleotide sequence SEQ ID NO:5), and made recombinant constructs for expressing the mutant (the coding region of the recombinant construct is shown in SEQ ID NO:9, and the deduced amino acid sequence is shown in SEQ ID NO:10).

Thus, the present invention provides a novel polypeptide derived from the hyperthermophilic archaeon *Thermococcus guaymasensis* (Tg), and variants thereof. The polypeptide was found to exhibit catalytic activity (e.g. alcohol dehydrogenase activity) and to have utility for example as a biocatalyst, in particular for chiral catalysis. Polynucleotides, e.g. isolated polynucleotides, encoding polypeptides of the invention are also encompassed.

Thus, in embodiments, the present invention provides an isolated polypeptide selected from the group consisting of:
- (a) a polypeptide comprising an amino acid sequence as set forth in SEQ ID NO: 2, 4, 6, 8, or 10;
- (b) fragments or derivatives of the polypeptide of (a) having catalytic activity;
- (c) fragments of the polypeptide of (a) comprising at least 18, at least 20, at least 25, or at least 30 contiguous amino acids from SEQ ID NO: 2, 4, or 6 or the alcohol dehydrogenase enzyme portion of SEQ ID NO:8 or 10;
- (d) fragments of the polypeptide of (a) comprising a catalytic zinc binding motif sequence and/or a cofactor binding motif sequence and/or a cysteine residue at a position corresponding to position 39 in SEQ ID NO:4;
- (e) fragments of the polypeptide of (a) comprising
  - (i) residue(s) 63 to 77 and/or 184 to 189 and/or 39 of SEQ ID NO:4;
  - (ii) residue(s) 64 to 78 and/or 185 to 189 and/or 40 of SEQ ID NO:2 or 6; or
  - (iii) residue(s) 116 to 130 and/or 237 to 241 and/or 92 of SEQ ID NO: 8 or 10; and having catalytic activity;
- (f) fragments of the polypeptide of (a) comprising SEQ ID NOS: 23 and 24 and having catalytic activity;
- (g) fragments of the polypeptide of (a) comprising SEQ ID NO: 25;
- (h) a polypeptide comprising:
  - (i) from about residues 63 to 77 and from about residues 184 to 189 and residue 39 of SEQ ID NO:4;
  - (ii) from about residues 64 to 78 and from about residues 185 to 189 and residue 40 of SEQ ID NO:2 or 6; or
  - (iii) from about residues 116 to 130 and from about residues 237 to 241 and residue 92 of SEQ ID NO: 8 or 10;
- (i) fragments of the polypeptide of (a) comprising cysteine residues at positions corresponding to Cys39, Cys56, Cys213 and Cys306 in SEQ ID NO:4;
- (j) amino acid sequences comprising at least 10 contiguous amino acids and sharing amino acid identity with the amino acid sequences of (a)-(i), wherein the percent amino acid identity is selected from the group consisting of at least 80%, at least 85%, at least 90%, at least 95%, at least 97.5%, at least 99%, and at least 99.5%.

In some embodiments, the isolated polypeptide of the invention comprises polypeptides having the full length amino acid sequence of SEQ ID NOs: 2, 4, 6, 8 or 10. The invention also encompasses fragments having at least 7 contiguous amino acids from any one of SEQ ID NOs: 2, 4, and 6, and the enzyme portion of SEQ ID NOS: 8 and 10. For example, the fragments may comprise at least 10, 15, 18, 20, 25, 30, 40, 50, 60, 75, 80, 90, 100, 125, 1150, 175, 200, 225, 250, 275, 300, 325, or 350, or any number therebetween, of contiguous amino acids from any one of SEQ ID NOs: 2, 4, and 6, and the enzyme portion of SEQ ID NOS: 8 and 10 (which spans residues Ser54 to Glu417 of these sequences). For example, these fragments may comprise between about 7 to 30, 18 to 30, or 20 to 30 amino acids.

The invention also encompasses a polypeptide having an amino acid sequence that has a sufficient or a substantial degree of identity or similarity to a sequence set forth in FIG. 4. Substantially identical sequences can be identified by those of skill in the art as having structural domains and/or having functional activity in common with TgADH. Methods of determining similarity or identity may employ computer algorithms such as, e.g., BLAST, FASTA, and the like. For sequence comparison, typically one sequence acts as a reference sequence, to which test sequences are compared. Alternatively, the percent identity of two amino acid or two nucleic acid sequences can be determined by comparing sequence information using the GAP computer program, version 6.0.

Polypeptides and fragments may also contain a segment that shares at least 70% (at least 75%, 80%-85%, 90%-95%, at least 97.5%, or at least 99%, and most preferably at least 99.5%) with any such segment of TgADH, when aligned so as to maximize overlap and identity while minimizing sequence gaps. Visual inspection, mathematical calculation, or computer algorithms can determine the percent identity.

Thus, the invention includes polypeptides that comprise an amino acid sequence that is at least 60%, 65%, 70%, 75%, 80%, 85%, 90%, 93%, 95%, 99% or more identical to all or a portion of the sequences set forth in SEQ ID NOS: 2, 4, 6, 8 and 10. Where the sequences share identity along a portion of SEQ ID NOS: 2, 4, 6, 8 and 10, the portion may be, for example, about residues 1 to 300, about residues 1 to 250, about residues 1 to 200, about residues 1 to 150, or other portions along which the sequences are compared. The portion being compared with depend, for instance, on the length and sequence of the test sequence.

One of skill will recognize that individual substitutions, deletions or additions to a nucleic acid sequence, peptide, or polypeptide sequence that alters, adds or deletes a single amino acid or a small percentage of amino acids in the encoded sequence is a conservatively modified variant, where the alteration results in a molecule having substantially the same functional activity (e.g., catalytic activity), and such variants (e.g. mutants, derivatives, and fragments) are encompassed in the invention, as well as variants resulting in improved characteristics. For example, variant polypeptides can have between 1 and 10 (i.e. 1, 2, 3, 4, 5, 6, 7, 8, 9, or 10) or more substitutions and/or deletions and/or additions.

The invention provides both full-length and mature forms of TgADH polypeptides. Full-length polypeptides are those having the complete primary amino acid sequence of the polypeptide as initially translated. The amino acid sequences of full-length polypeptides can be obtained, for example, by translation of the complete open reading frame ("ORF") of a cDNA molecule. Several full-length polypeptides may be encoded by a single genetic locus if multiple mRNA forms are produced from that locus by alternative splicing or by the use of multiple translation initiation sites. The "mature form" of a polypeptide refers to a polypeptide that has undergone post-translational processing steps, if any, such as, for example, cleavage of the signal sequence or proteolytic cleavage to remove a prodomain. The mature form(s) of such polypeptide may be obtained by expression, in a suitable mammalian cell or other host cell, of a polynucleotide that encodes the full-length polypeptide. The sequence of the mature form of the polypeptide may also be determinable from the amino acid sequence of the full-length form, through identification of signal sequences or protease cleavage sites. For example, the full length polypeptide sequence of TgADH is shown in SEQ ID NO: 2, while the mature polypeptide sequence (where the initial M residues is absent) is SEQ ID NO: 4.

In another aspect of the invention, a polypeptide may comprise particular motifs or domains from the TgADH polypeptide, or combinations thereof. For example, native TgADH has the following features:

(a) a catalytic zinc binding motif sequence located between about residues 63 to 77 of SEQ ID NO: 4 (which corresponds to residues 64 to 77 of SEQ ID NO:2 and 6, residues 116 to 130 of SEQ ID NOS: 8 and 10, and has the sequence set forth in SEQ ID NO:23), (b) a cofactor (e.g. NADP) binding motif sequence located between about residues 184 to 189 of SEQ ID NO: 4 (which corresponds to residues 185 to 189 of SEQ ID NO:2 or 6, and residues 116 to 130 of SEQ ID NO: 8 and 10, and has the sequence set forth in SEQ ID NO:23), (c) a cysteine at located at residue 39 of SEQ ID NO:4 (which corresponds to residues 40 of SEQ ID NOS: 2 and 6 and residue 92 of SEQ ID NOS: 8 and 10) that is thought to be located in the active site of the enzyme, and (d) a unique sequence located at residues 119 to 124 in SEQ ID NO:4 (which corresponds to residues 120 to 125 of SEQ ID NOS: 2 and 6, and residues 172 to 177 of SEQ ID NOS: 8 and 10, and has the sequence set forth in SEQ ID NO:25).

It may be desirable for a polypeptide of the invention to comprise one, two, three or all of these above-described features (a) to (d). Further, in some embodiments, it may be preferable for polypeptides to include such features as part of a broader region (such as a 20, 30 or 40 amino acid region) from the exemplified sequence that comprises the motif or region of interest. For example, the polypeptide of the invention may comprise the catalytic zinc binding motif sequence as part of a broader region spanning between about residues 50 to 80 or 45 to 90 of SEQ ID NO: 4 (or corresponding residues 51 to 81 or 46 to 91 of SEQ ID NO:2 and 6, or residues 103 to 133 or 98 to 143 of SEQ ID NOs: 8 and 10), or may comprise the cofactor binding motif sequence as part of a broader region spanning between about residues 175 and 190, 170 and 200, or 165 and 230 of SEQ ID NO: 4 (which corresponds to residues 176 to 191, 171 to 201, or 166 to 230 of SEQ ID NOS: 2 and 6, or residues 228 to 243, or 223 to 253, or 218 to 282 of SEQ ID NOS: 8 and 10).

In some embodiments, it will be preferred that the polypeptide of the invention comprises a fragment of one of SEQ ID NOS: 2, 4, 6, 8, 10 that has both of a catalytic zinc binding motif sequence and a cofactor binding motif sequence. In these cases, suitable fragments include those comprising residues 1 to 363, 1 to 250, 1 to 200, or 1 to 190, of SEQ ID NO:4 and the like (or corresponding fragments from SEQ ID NOS: 2, 6, 8 and 10). Other fragments could include residues 10 to 300, 20 to 250, 30 to 220, 40 to 220, 50 to 200, 60 to 190, of SEQ ID NO:4 (or corresponding fragments from SEQ ID NOS: 2, 6, 8 and 10) and the like. Other fragments comprising both domains are possible, including fragments that comprise segments of SEQ ID NOS: 2, 4, 6, 8 or 10 that are discontinuous and joined together.

The cysteine residue located at position 39 in SEQ ID NO:4 is believed to play a role in the catalytic activity of the enzyme. Consequently, in many cases, polypeptides of the invention will have a cysteine residue at the position corresponding to position 39 in SEQ ID NO:4.

Polypeptides of the invention may exhibit one or more of the following desirable characteristics: (a) thermostability; (b) catalytic activity; (c) stereospecificity; (d) solvent tolerance; (e) a preference for primary or secondary alcohols and/or corresponding ketones or aldehydes; and/or (f) a preference for R-stereochemistry. For many purposes, polypeptides of the invention that have catalytic activity, for example, alcohol dehydrogenase activity (which may include both oxidation and reduction reactions as used herein) will be preferred. For some purposes, polypeptides that also have thermostability and/or stereospecificity and/or solvent tolerance may be especially preferred. One of skill in the art can readily assay polypeptides of the invention (e.g. fragments or mutants or derivatives of the polypeptides disclosed herein) for ADH activity, thermostability, stereospecificity, and/or solvent tolerance using the methods described herein or any suitable methods known in the art.

Where the polypeptide is an active polypeptide, such as an enzyme or active portion or variant thereof, the polypeptide may exhibit stability and activity over a wide temperature range (e.g. 20 to 150° C., 30 to 100° C., 30 to 100° C., 50 to 100° C., or 50 to 95° C., or 60 to 95° C., or 70 to 100° C., or 80 to 95° C.). In some embodiments, the polypeptides exhibit catalytic activity at temperatures of higher than 50° C., higher than 60° C., higher than 70° C., higher than 80 C., higher than 90° C., and higher than 100° C. It has been found that the activity of the TgADH enzyme increases with increasing temperature, at least up to 95° C. Although the $t_{1/2}$ of the enzyme is generally decreased at very high temperatures. Any suitable temperature can be seleted for a chemical reaction, however, the skilled person will consider the stability and reactivity of other reagents and cofactors present in the reaction mixture. A skilled person can optimize the reaction conditions, such as temperature, pH, pressure, incubaton time, etc. to achieve desired properties of the enzyme or the reaction.

As discussed above, polypeptides of the invention may have catalytic activity. In particular, polypeptides of the invention may have ADH activity (which herein is understood toinclude both oxidation and reduction activity), that may be stereoselective. Thus, the present invention provides methods of reducing primary or secondary alcohol susbtrates, or of oxiding their corresponding aldehydes or ketones, using the polypeptides of the invention. Such reactions may be stereoselective. Suitable substrates are discussed below.

Polypeptides of the invention may be prepared using heterologous expression techniques, e.g. by culturing a host cell that has been transformed with expression constructs comprising cDNA encoding a polypeptide of interest linked to expression control sequences, under culture conditions suitable to express the polypeptide of the invention. The resulting expressed polypeptide may then be purified from such culture using conventional purification processes, such as gel filtration and ion exchange chromatography. The purification of the polypeptide may also include an affinity column containing agents which will bind to the polypeptide; one or more column steps over such affinity resins as DEAE-sepharose, concanavalin A-agarose, Heparin-Toyopearl® or Cibacrom blue 3GA Sepharose®; one or more steps involving hydrophobic interaction chromatography using such resins as phenyl ether, phenyl sepharose, butyl ether, or propyl ether; or immunoaffinity chromatography. Alternatively, the polypeptide of the invention may also be expressed in a form that will facilitate purification. For example, it may be expressed as a fusion polypeptide, such as those of maltose binding polypeptide (MBP), glutathione-S-transferase (GST) or thioredoxin (TRX), or with a HIS tag. For example, SEQ ID NOS: 8 and 10 contain a HIS tag, which can be used to do a one-step purification on a Nickel column. Kits for expression and purification of such fusion polypeptides are commercially available from New England BioLab (Beverly, Mass.), Pharmacia (Piscataway, N.J.), and InVitrogen, respectively. The polypeptide can also be tagged with an epitope and subsequently purified by using a specific antibody directed to such epitope. One such epitope ("Flag") is commercially available from Kodak (New Haven, Conn.). Finally, one or more reverse-phase high performance liquid chromatography (RP-HPLC) steps employing hydrophobic RP-HPLC media, e.g., silica gel having pendant methyl or other aliphatic groups, can be employed to further purify the polypeptide. Some or all of the foregoing purification steps, in various combinations, can also be employed to provide a substantially homogeneous recombinant polypeptide.

A polypeptide of the invention may also be produced by conventional chemical synthesis. Methods for constructing the polypeptides of the invention by synthetic means are known to those skilled in the art. The synthetically-constructed polypeptide sequences, by virtue of sharing primary, secondary or tertiary structural and/or conformational characteristics with a native polypeptides may possess biological properties in common therewith, including functional activity.

The invention also provides polynucleotides encoding the polypeptides described above. Thus, in embodiments, the present invention provides an isolated nucleic acid molecule, or a fragment, variant or derivative thereof, selected from the group consisting of:
(a) a nucleic acid comprising a nucleotide sequence selected from the group consisting of SEQ ID NOS: 1, 3, 5, 7, and 9 and sequences complementary thereto;
(b) a nucleic acid comprising a nucleotide sequence at least 70% identical to a nucleotide sequence selected from the group consisting of SEQ ID NOS: 1, 3, 5, 7, and 9 and sequences complementary thereto;
(c) a nucleic acid comprising a nucleotide sequence at least 90% identical to a nucleotide sequence selected from the group consisting of SEQ ID NOS: 1, 3, 5, 7, and 9 and sequences complementary thereto;
(d) a nucleic acid comprising a nucleotide sequence at least 99% identical to a nucleotide sequence selected from the group consisting of SEQ ID NOS: 1, 3, 5, 7, and 9 and sequences complementary thereto; and
(e) a nucleic acid comprising at least 30 contiguous nucleotides of a nucleotide sequence selected from the group consisting of SEQ ID NOS: 1, 3, 5, 7, and 9 and sequences complementary thereto; and
(f) a nucleic acid capable of hybridizing to the nucleic acid of (a) under conditions of moderate or high stringency.

The polynucleotides of the invention may be used for example to express polypeptides of the invention.

Polynucleotides of the invention may also be used for example as probes or primers (e.g. for sequencing and/or site-directed mutagenesis). Such polynucleotides generally comprise at least about 18 contiguous nucleotides of a DNA sequence, but may include up to 30 or 60 or more nucleotides. For example, a polynucleotide consisting of a fragment comprising at least 18 contiguous nucleotides of the nucleotide sequence of any one of SEQ ID NOS:1, 3, 5, 7, and 9, may be useful as a primer or a probe.

The basic parameters affecting the choice of hybridization conditions and guidance for devising suitable conditions are set forth elsewhere above. Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified. In certain embodiments, degenerate primers can be used as probes for non-human genetic libraries. Such libraries would include but are not limited to cDNA libraries, genomic libraries, and even electronic EST (express sequence tag) or DNA libraries. Homologous sequences identified by this method would then be used as probes to identify non-human homologues of the ADAM-H9 sequence identified herein.

Polynucleotides of the invention may be inserted into expression vectors, and operably linked to an expression control sequence, to generate constructs that are useful for producing polypeptides of the invention via heterologous expression. Suitable expression vectors for this purpose include: pET (e.g. pET30A), pMT2, Impact System or pMAL™ Protein Fusion and Purification System (available from New England Biolabs), pPICZα A, B, and C Pichia expression vectors for selection on Zeocin™ (available from Invitrogen), or the S30 T7 High-Yield Protein Expression System or TNT® SP6 High Yield Wheat Germ System (available from Promega).

Suitable host cells for expression of the polypeptide include both eukaryotic and prokaryotic cells. In some embodiments, the polypeptide is produced in lower eukaryotes such as yeast or in prokaryotes such as bacteria. Seletion of a suitable expression system is convenient because the enzyme has only one subunit to be expressed (4 identical monomers associate to form homotetramer). Suitable bacterial strains include, for example, *Escherichia coli, Bacillus subtilis, Salmonella typhimurium*, or any bacterial strain capable of expressing heterologous polypeptides. Mention is made of the codon-plus *E. coli* BL 21-RIL expression strain, as an example of a suitable host cell for expressing TgADH and variants thereof. Potentially suitable yeast strains include *Saccharomyces cerevisiae, Schizosaccharomyces pombe, Kluyveromyces strains, Candida*, or any yeast strain capable of expressing heterologous polypeptides. Mammalian host cells may also be employed, as may be insect cells.

Polynucleotides of the invention may also be used to generate a transgenic organism, using conventional techniques.

Overview of the Experimental Findings

The following overview is provided to assist in the understanding of the invention further described below. This overview should not be construed as limiting the scope of the invention.

The present inventors noted the production of ethanol and acetoin by *T. guaymasensis* during glucose fermentation and were able to isolate and purify an ADH from this hyperthermophile. The purified ADH from *T. guaymasensis* (TgADH) is the first zinc-containing ADH characterized from the *Thermococcus* species.

The novel ADH (termed TgADH herein) was found to exhibit high enzymatic activity, thermostability, an ability to act on a variety of alcohols, good solvent tolerance, an ability to regenerate an expensive cofactor NADPH by coupling with inexpensive isopropanonl and a preference in producing R-configured molecules compared to other known ADHs. These characteristics make TgADH a superior candidate for chiral compound biosynthesis and other applications, such as biofuel production.

*Thermococcus guaymasensis* is a hyperthermophilic starch-degrading archaeon producing acetate, $CO_2$, $H_2$, ethanol and acetoin as end products. An alcohol dehydrogenase (TgADH) from *Thermococcus guaymasensis* was purified to homogeneity and was found to be a homotetramer with a subunit size of 40±1 kDa. The gene encoding the enzyme was cloned and sequenced, which had 1098 bp (SEQ ID NO: 1) corresponding to 365 amino acids (SEQ ID NO:2) and showed sequence homology to zinc-containing ADHs and L-threonine dehydrogenases with both binding motifs of catalytic zinc and $NADP^+$. The native form of the protein was found to have 364 amino acids (SEQ ID NO: 4) being encoded by a polynucleotide having 1095 base pairs (SEQ ID NO: 3). Metal analyses confirmed that this NADP⁺-dependent enzyme contained 0.9±0.03 g atom zinc per subunit. It was a predominantly primary-secondary ADH and exhibited a substrate preference for secondary alcohols and corresponding ketones. Particularly, the enzyme with unusual stereoselectivity catalyzed an anti-Prelog reduction of racemic (R/S)-acetoin to (2R,3R)-2,3-butanediol and meso-2,3-butanediol. The optimal pH-values for the oxidation and formation of alcohols were 10.5 and pH 7.5, respectively. Besides being hyperthermostable, the enzyme activity increased as the temperature was elevated up to 95° C. The enzyme was active in the presence of methanol up to 40% (v/v) in the assay mixture. The reduction of ketones underwent high efficiency by coupling with excess isopropanol to regenerate NADPH. So, the enzyme can be used as a potent biocatalyst for asymmetric synthesis. The kinetic parameters of the enzyme showed that apparent $K_m$-values and catalytic efficiency for NADPH was 40 times lower and 5 times higher respectively than those for NADP⁺. The physiological roles of the enzyme were thus proposed to be in the formation of alcohols such as ethanol or acetoin co-occuring with the NADPH oxidation.

The TgADH enzyme belongs to the family of zinc-containing ADHs with catalytic zinc only. It was verified that the enzyme had binding motifs of catalytic zinc only ($GHEX_2GX_5GX_2V$, residues 63-77) and cofactor NADP ($GXGX_2G$, residues 184-189). The tertiary structural modeling showed two typical domains, one catalytic domain close to N-terminal and one coenzyme-binding domain close to C-terminal end. Since its codon usage pattern seemed to be different from that of E. coli, the enzyme was over-expressed in the E. coli codon plus strain using pET-30a vector. The recombinant enzyme was soluble and active (1073 U/mg), which was similar to the native enzyme (1049 U/mg). The recombinant possessed very similar properties with the native enzyme. The optimal pH values for ethanol oxidation and acetaldehyde reduction were 10.5 and 7.5 respectively, while activity for alcohol oxidation was higher than that of aldehyde reduction. The enzyme activity was inhibited in the presence of 100 µM $Zn^{2+}$ in the assay mixture and it has a half-life of 6 hours after exposed to air. The enzyme had outstanding thermostability with 60% activity after incubation at 80° C. for 40 hours.

The following table (TABLE 1) compares TGADH with other ADHs that are commonly used for chiral compound biosynthesis:

ured) compared to competitive alternatives, and good solvent tolerance, TgADH is an excellent candidate for chiral compound biosynthesis.

T. guaymasensis ADH (TGADH) is a thermostable and highly active zinc-containing ADH with stereo-specificity. It has great potential applications in production of stereo-specific compounds. To be able to produce large quantity of this enzyme quickly and economically, an over-expression system was developed.

To obtain large quantity of the recombinant enzyme, large-scale growth of E. coli could carried out (e.g. up to 15 liters or more). Cell-free extract of the E. coli cells can be heat-treated (e.g. 60° C. for one hour), and then centrifuged to remove denatured E. coli proteins before applying on to a purification column such as a DEAE-ion exchange column. It is possible to use additional purificiation columns (such as a gel-filtration cloumn) to further purify the enzyme. Catalytic properties of the purified recombinant ADH can be analyzed and compared with those of the native ADH to ensure that they indeed have the same activity.

In the present invention, the structural gene encoding TgADH was cloned, sequenced and over-expressed in mesophilic host E. coli, and the resulting enzyme was purified and its catalytic properties were characterized. The over-expression of TgADH was a successful fundament for further engineering of the enzyme.

The enzyme had outstanding thermostability with 60% activity after incubation at 80° C. for 40 hours.

The recombinant enzyme was soluble and active (1073 U/mg), which was similar to the native enzyme (1049 U/mg).

Advantageously, the enzyme was found to be suitable for catalyzing both oxidation and reduction reactions. A skilled person can adjust the conditions to drive the reaction in the preferred direction. In general, oxidation reactions were favoured at more alkanine pH than reduction reactions.

In general, the pH selected for oxidation can be greater than about 8 (e.g. about 8.0, about 8.5, about 9.0, about 9.5, about 10.0, about 10.5, about 11.0, or about 11.5). For example, the pH selected for oxidation can be about 10.5.

In general, the pH selected for reduction can be less than about 10 (e.g. about 6.0, about 6.5, about 7.0, about 7.5, about 8.0, about 8.5, about 9.0 or about 9.5). For example, the pH selected for oxidation can be about 7.5.

In an exemplified embodiment, the optimal pH for ethanol oxidation and acetaldehyde reduction were 10.5 and 7.5

TABLE 1

| ADH source | T. guaymasensis (TgADH) | S. solfataricus | A. pernix | P. fuirosus | T. brockii[1] |
|---|---|---|---|---|---|
| Enzyme activity (U mg⁻¹) | 1149 | 5.3 | 1.1 | 10.3 | 30-90 |
| Thermostability | 24 hr at 95° C. | 3 hr at 85° C. | 30 min at 98° C. | 130 min at 100° C. | 60 min at 93.8° C. |
| Chiral compound synthesis preference | R-configured | S-configured | S-configured | S-configured | S-configured |
| Solvent tolerance | 24% methanol | 10% isopropanol 30% ethanol | NA | 30% isopropanol | 64% isopropanol |

[1]T brockii ADH that is currently available at Sigma Aldrich is essentially T ehtanolicus ADH Therefore, with the ability to act on many different types of alcohols, high enzymatic activity, excellent thermostability, distinct chiral compound synthesis preference (R-configrespectively, although a range of other pHs could be used (see above). Activity for alcohol oxidation was higher than that of aldehyde reduction.

In an exemplified embodiment, the optimal pH of the enzyme was found to be 10.5 for the 2-butanol oxidation and 7.5 for the 2-butanone reduction, respectively, although a range of other pHs could be used (see above) for these reactions.

The substrate specificity of the purified enzyme was determined using a set of alcohols, aldehydes and ketones (see Table 2). In the oxidation reactions, *T. guaymasensis* ADH was able to transform a broad range of primary alcohols. Moreover, the purified enzyme showed higher activities using secondary alcohols such as 2-butanol and 2-pentanol as substrates, suggesting that the enzyme is preferentially a primary-secondary ADH, although substrate speficity is not limited to primary and secondary alhohols. In reduction reactions, the enzyme exhibited the ability of reducing various aldehydes and ketones.

The enzyme exhibited a preference for R-stereochemistry. For instance, the enzyme predominantly oxidized R-hydroxyl group of 2,3-butanediol and minorly functioned on S-hydroxyl group.

Thus, it is expected that a broad range of alcohols (preferably primary and secondary alcohols, more preferably secondary alcohols, and even more preferably secondary alcohols having R-stereochemistry) may be used as substrates for oxidation reactions and that a correspondingly broad range of aldehydes and ketones may be used as substrates for reduction reactions. There are ADH that can catalyze long chain substrates, so it is reasonable to predict that TgADH may be able to catalyze long chain substrates (i.e. substrates comprising carbon chains of 10 or more carbon atoms) as well. Examples of suitable substrates for TgADH include those listed in Table 2 below:

The compounds listed in Table 2 may have chiral properties that may affect bioactivity and therefore may have medicinal importance Suitable substrates may also include naturally occurring or synthetic amino acids comprising either alcohol moieties (such as serine) or aldehyde or ketone moieties, and peptides comprising them.

The apparent $K_m$ value for the coenzyme NADPH was much lower than that for the coenzyme $NADP^+$. These catalytic properties suggest that the enzyme could play an important role in the oxidation of NADPH rather than the reduction of $NADP^+$ in vivo. However, in a laboratory or industrial environment, the conditions and reagents may be selected to drive the reaction in the opposite direction.

The TgADH enzyme proved to be solvent tolerant. Enzymes resistant to solvent inactivation are of great interest from scientific and practical points of view.

Advantageously, the feature of solvent tolerance made it feasible to regenerate the coenzyme NADPH using an inexpensive co-substrate, such as isopropanol, in excess amounts. The ability to regenerate the co-enzyme provides a significant advantage since the amount of co-factor required can be reduced. Cofactors are typically very costly and must be continually replenished in the reaction system as they are depleted. Also, current systems that do permit regeneration of the cofactor typically employ a two-enzyme system. The present invention provides a one-enzyme system where the same enzyme catalyzes the regeneration of the cofactor as well as the reaction of interest.

Thus, in some embodiments, there is provided an enzyme which catalyzes the regeneration of a cofactor, such as NADPH, in a reaction system. The cofactor is important for

TABLE 2

Examples of ketone and corresponding alcohol substrates for TgADH

| Ketone | Molecular structure | Alcohol | Molecular structure |
|---|---|---|---|
| 1-phenyl-2-propanone | 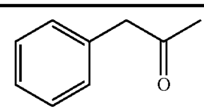 | 1-phenyl-2-propanol | 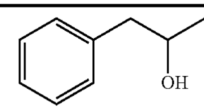 |
| Ethyl-4-chloro-3-oxobutanoate | 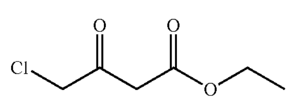 | Ethyl-4-4-chloro-3-hydroxy-butanoate | 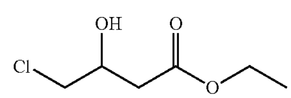 |
| 2-octanone | 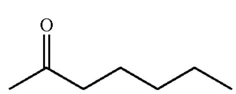 | 2-octanol | 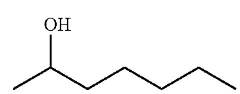 |
| Cyclooctanone | 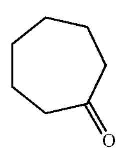 | cyclooctanol | 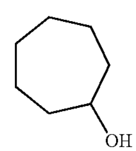 |
| 2,5-hexanedione | 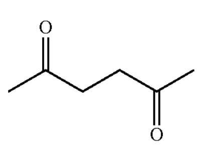 | hexanediol | 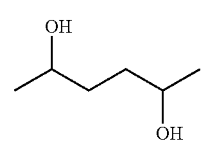 |
| 6-benzyloxy-3,5-dioxo-hexanoic-acid ethyl ester | | 6-benzyloxy-3,5-dihydroxy-hexanoic acid ethyl ester | | enzymatic activity. This feature provides a significant advantage since the amount of the co-factor required for the reaction can be reduced.

Any suitable solvent may be used, in accordance with embodiments of the invention, and in any suitable amount in the reaction mixture, for example, 5%, 10%, 15%, 20%, 25%, 30%, 35%, 40%, or 50% (v/v) in the reaction mixture. Exemplary co-substrates that can be used for the re-generation of co-enzyme for the enzymatic reaction(s) include 2-propanol, ethanol, 3-pentanol. Generally, any alcohol that the enzyme can oxidize could be used as co-substrate for coenzyme regeneration. However, as the skilled person will recognize, the practical choice will depend on such factors as the desired substates and products, reaction rate, yield, and cost.

Unless otherwise defined, all technical and scientific terms used herein have the same meaning as commonly understood by one of ordinary skill in the art to which this invention belongs. All headings and subheading provided herein are solely for ease of reading and should not be construed to limit the invention. Although methods and materials similar or equivalent to those described herein can be used in the practice or testing of the invention, suitable methods and materials are described below.

All publications, patent applications, patents, and other references mentioned herein are incorporated by reference in their entirety.

In addition, the materials, methods, and examples are illustrative only and not intended to be limiting. The following examples are intended to illustrate particular embodiments and not to limit the scope of the invention.

EXAMPLES

Example 1

Isolation, Purification and Characterization of TgADH

Materials and Methods
Chemicals and Organisms.

All chemicals were commercially available. (R)-(−)-2-butanol, (S)-(+)-2-butanol, (2R,3R)-(−)-2,3-butanediol, (2S,3S)-(+)-2,3-butanediol and meso-2,3-butanediol were purchased from Sigma-Aldrich Canada (Oakville, ON, Canada). *T. guaymasensis* DSM 11113™ was obtained from DSMZ—Deutsche Sammlung von Mikroorganismen und Zellkulturen, Braunschweig, Germany. KOD Hot Start DNA polymerase and T4 DNA ligase were purchased from Invitrogen and Stratagene (La Jolla, Calif., USA), respectively. DNA ladder and restriction enzymes were purchased from Fermentas Canada Inc. (Burlington, ON, Canada). The pGEM-T easy vector (Promega, Madison, Wis., USA) was used for the cloning of PCR products. *E. coli* DH5α was used as a host for cloning and grown under standard conditions following the instructions of the manufacturers.

Growth Conditions.

*T. guaymasensis* was cultured in the medium as described previously (Canganella et al. 1998) with modifications. The medium at pH 7.0 contained chemicals, g/L: KCl, 0.33; $MgCl_2·2H_2O$, 2.7; $MgSO_4·7H_2O$, 3.4; $NH_4Cl$, 0.25; $CaCl_2·2H_2O$, 0.14; $K_2HPO_4$, 0.14; $Na_2SeO_3$, 0.01 mg; $NiCl_2·6H_2O$, 0.01 mg; $NaHCO_3$, 1.0; NaCl, 18; resazurin, 0.001; cysteine·HCl·$H_2O$, 0.5; $Na_2S·9H_2O$, 0.5; bacto-yeast extract, 10; trypticase soy broth, 10; elemental sulfur, 10; dextrose, 5; HEPES, 5.2; trace mineral solution, 10 ml; vitamin solution, 10 ml. The preparation of trace mineral and vitamin solutions was described as previously (Balch et al. 1979). In a large scale of cultivation, it was routinely cultured in a 20-l glass carboy at 88° C. in which elemental sulfur and HEPES were omitted. The resulting cell pellet after centrifugation was frozen in liquid nitrogen immediately and stored at −80° C. until use.

Preparation of Cell-Free Extract.

The frozen cells (50 g) of *T. guaymasensis* were resuspended in 450 ml of 10 mM Tris-HCl anaerobic buffer (pH 7.8) containing 2 mM dithiothreitol (DTT), 2 mM sodium dithionite (SDT) and 5% (v/v) glycerol. The suspension was incubated at 37° C. for 2 h under stirring. The supernatant was collected as the cell-free extract after 30 min centrifugation at 10,000×g.

Purification of *T. guaymasensis* ADH.

All the purification steps were carried out anaerobically at room temperature. The cell-free extract of *T. guaymasensis* was loaded onto a DEAE-Sepharose column (5×10 cm) that was equilibrated with buffer A [50 mM Tris/HCl (pH 7.8) containing 5% (v/v) glycerol, 2 mM DTT, 2 mM SDT]. *T. guaymasensis* ADH that bound weakly to the column was eluted out while buffer A was applied at a flow rate of 3 ml $min^{-1}$. A linear gradient (0-0.5 M NaCl) was further applied onto the column. Fractions containing ADH activity were then pooled and loaded onto a Hydroxyapatite column (2.6× 15 cm) at a flow rate of 2 ml $min^{-1}$. The column was applied with a gradient (0-0.5 M potassium phosphate in buffer A) and ADH started to elute from the column at a concentration of 0.25 M potassium phosphate. Fractions containing enzyme activity were pooled and applied to a Phenyl-Sepharose column (2.6×10 cm) equilibrated with 0.8 M ammonia sulfate in buffer A. A linear gradient (0.82-0 M ammonia sulfate in buffer A) was applied at a flow rate of 2 ml $min^{-1}$ and the ADH started to elute at a concentration of 0.4 M ammonia sulfate. Fractions containing ADH activity were desalted and concentrated by ultrafiltration using 44.5 mm YM-10 membranes (Millipore Corporation, Bedford, Mass., USA). The concentrated samples were applied to a Superdex-200 gel filtration column (2.6×60 cm) equilibrated with buffer A containing 100 mM KCl at a flow rate of 2.5 ml $min^{-1}$. The purity of the fractions containing ADH activity was verified using sodium dodecyl sulfate-polyacrylamide gel electrophoresis (SDS-PAGE) as described previously (Laemmli 1970).

Enzyme Assay and Protein Determination.

The catalytic activity of *T. guaymasensis* ADH was measured at 80° C. by using Genesys 10UV-Vis spectrophotometer (Thermo Fisher Scientific, Waltham, Mass., USA) and monitoring the substrate-dependent absorbance change of NADP(H) at 340 nm ($\epsilon_{340}$=6.3 $mM^{-1}cm^{-1}$, Ziegenhorn et al. 1976). Unless otherwise specified, the enzyme assay was carried out in duplicate using the assay mixture (2 ml) for alcohol oxidation contained 50 mM 2-butanol and 0.4 mM $NADP^+$ in 100 mM CAPS buffer (pH 10.5). The assay mixture (2 ml) for the reduction of ketone/aldehyde contained 6 mM 2-butanone and 0.2 mM NADPH in 100 mM HEPES (pH 7.5). The purified enzyme (0.25 µg) initiated the enzyme assay. One unit of the activity is defined as 1 µmol NADPH formation or oxidation per min. The protein concentrations of all samples were determined using the Bradford method and bovine serum albumin served as the standard protein (Bradford 1976).

Determination of Catalytic Properties.

The effect of pH on the enzyme activities was determined over a range of 5.5-11.4. The buffers (100 mM) used were phosphate (pH 5.5-8.0), EPPS (8.0-9.0), glycylglycine (9.0-9.7), and CAPS (9.7-11.4). The effect of the temperature on the enzyme activity was examined at temperatures from 30 to 95° C. Enzyme thermostability was determined by incubating the enzyme in sealed serum bottles at 80° C. and 95° C., respectively. Residual activity was assayed at various time intervals under the standard assay conditions. Substrate specificity was determined using primary and secondary alcohols (50 mM), diols and polyols (50 mM), or aldehydes and ketones (6 mM) under standard assay conditions. The effect of cations, ethylenediaminetetraacetic acid (EDTA) or DTT on enzyme activities was carried out by measuring the reduction of 2-butanone in 100 mM HEPES buffer (pH 7.0) considering low solubility of cations at alkaline pHs.

Enzyme Kinetic parameters were determined using different substrates and coenzymes (NADP$^+$ or NADPH). Concentrations of substrates were $\geq$10× apparent $K_m$ unless specified for NADPH, sec-butanol, NADP and 2-butanone, while concentrations of the corresponding co-substrates were kept constant and higher than 10× apparent $K_m$. Apparent values of $K_m$ and $V_{max}$ were calculated using the curve fittings of SigmaPlot (Systat Software Inc., San Jose, Calif., USA).

Metal Analyses.

The metal contents of *T. guaymasensis* ADH were determined by using inductively coupled plasma mass spectrometry (VG Elemental PlasmQuad 3 ICP-MS at the Chemical Analysis Laboratory, University of Georgia, USA). The purified enzyme was pretreated to wash off non-binding metals in the anaerobic chamber where the oxygen level was kept below 1 ppm. The washing buffer used was 10 mM Tris/HCl containing 2 mM DTT (pH 7.8). The washing procedure was carried out using YM-10 Amicon centrifuge tubes, including 7 repeats of centrifugation (concentration and refilling of buffers). The passthrough solution was collected as its control.

Ketone Reduction Coupled with the NADPH Regeneration.

The reaction mixture (2 ml) contained 100 mM HEPES buffer (anaerobic, pH 7.5), 50 mM 2-butanone or 2-pentanone, 25 µg *T. guaymasensis* ADH, 500 mM isopropanol and 1 mM NADPH. The reaction was carried out at 30° C. for 24 hours unless specified. The reactants (butanone/2-butanol and 2-pentanone/2-pentanol) were determined in a Shimadzu GC-14A gas chromatography (GC) equipped with a flame ionization detector (FID, 250° C.) and an integrator Shimadzu CR601 (Shimadzu Corporation, Kyoto, Japan). The GC analyses were performed under the following conditions: column, MXT-624 (0.53 mm ID×30 m length, Restek, Bellefonte, Pa., USA); FID sensitivity range, $10^2$; Carrier gas, helium at a linear velocity of 80 cm s$^{-1}$. For the 2-pentenone/2-pentanol determination, the following temperature program was used: isotherm at 60° C. for 3 min, 30° C./min ramp to 110° C., and isotherm at 110° C. for 2 min. For the 2-butanone/2-butanol determination, the following temperature program was used: isotherm at 40° C. for 3 min, 30° C./min ramp to 100° C., and isotherm at 100° C. for 2 min. The reaction mixture (1 µl) was directly applied onto the injector (200° C.) for GC analyses. The peak areas were quantitated using specific external standards.

Analyses of Fermentation Products.

The possible fermentation products such as ethanol, acetoin and 2,3-butanediol, were measured by using the above-mentioned GC systems with modifications. The temperature program was modified at the FID sensitivity range of 10: isotherm at 80° C. for 3 min, 10° C./min ramp to 150° C., and isotherm at 150° C. The peak areas were quantitated using specific external standards. Prior to the analyses, the culture medium was centrifuged at 10,000×g for 5 min and the supernatant was filtered to remove the residual cells by using nylon syringe filters (National Scientific Company, Rockwood, Tenn., USA).

Stereoselective Conversion Between Acetoin and 2,3-Butanediol.

The reaction mixture (2 ml) of 2,3-butanediol oxidation contained 100 mM CAPS buffer (anaerobic, pH 10.5), 50 mM (2R,3R)-(−)-2,3-butanediol or meso-2,3-butanediol, 25 µg *T. guaymasensis* ADH, 500 mM acetone and 1 mM NADP$^+$. The reaction mixture (2 ml) of acetoin reduction contained 100 mM HEPES buffer (anaerobic, pH 7.5), 50 mM racemic R/S-acetoin, 25 µg *T. guaymasensis* ADH, 500 mM isopropanol and 1 mM NADPH. All the reactions were carried out at 30° C. for 24 hours unless specified. After that, the reaction mixture (1 ml) was extracted with 1 ml ethyl acetate or dichloride methane with shaking on a Gyrotory water bath shaker model G76 (New Brunswick Scientific Co., INC., NJ, USA) at 350 rpm for 30 min (room temperature). The stereoselectivity of the purified enzyme was determined using the Shimadzu GC-14A gas chromatography equipped with a CP-Chirasil-Dex CB column (0.25 mm ID×25 m length, Varian Inc., Palo Alto, Calif., USA). The following GC operating conditions included the FID detector (250° C.) at a sensitivity range of 10 and helium as the carrier gas at a linear velocity of 40 cm s$^{-1}$. The temperature program for R/S-acetoin, (2R, 3R)-(−)-2,3-butanediol, (2S,3S)-(+)-2,3-butanediol and meso-2,3-butanediol was listed as the following: isotherm at 60° C. for 5 min, 30° C./min ramp to 90° C., isotherm at 90° C. for 6 min. The reaction mixture after extraction (0.5 µl) was directly applied onto the injector (200° C.) for each assay. The peak areas were quantitated using specific external standards. In order to identify if *T. guaymasensis* ADH catalyzed asymmetric reduction of 2-butanone to chiral 2-butanols, R-2-butanol or S-2-butanol formation was verified by using GC operating conditions described in this section except that the temperature program was set isothermally at 45° C. for 10 min.

Mass Spectrometry for Internal Sequences of *T. guaymasensis* ADH.

The purified enzyme was run on 12.5% SDS-PAGE and subjected to in-gel trypsin digestion. The resulting peptides were extracted and cleaned with the procedures described previously (Shevchenko et al. 1996). The resulting samples were applied for mass spectrometry analyses on a Waters Micromass Q-TOF Ultima using nano-spray injection as the sample delivery method (Mass Spectrometry Facility, University of Waterloo, Waterloo, ON, Canada). The PEAKS software (BSI, Waterloo, ON, Canada) was used for MS/MS profiling.

Results

Growth and Alcohol Formation of *T. guaymasensis*.

*T. guaymasensis* is a heterotrophic archaeon and could grow in the absence of sulfur during glucose fermentation. Ethanol was found to be one of the end products in the tested culture, and its production appeared to be correlated with growth. Whether *T. guaymasensis* was cultured in the presence of 20 mM HEPES buffer and 0.5% sulfur or not, the final pH of the media after 48 hours growth was around 6.0. Acetoin was detected as a metabolite in the spent medium (2-3 mM). The acetoin formation of *T. guaymasensis* was detectable after 2 hours in incubation and accumulated as the cell density increased under all tested conditions, implying that its production might not be as a response to the pH change. 2,3-butanediol could not be detected in the fermentation culture.

ADH Activities in the Cell-Free Extract of *T. guaymasensis*.

The production of both ethanol and acetoin indicated that *T. guaymasensis* may harbor multiple ADHs or a dominant ADH with multifunctions. The cell-free extract was prepared to investigate the presence of ADH activities. Alcohols such as glycerol, 1-butanol, 2-butanol, 2,3-butanediol and 1,4-butanediol, were used as assay substrates to differentiate the possible types of ADHs such as polyol, primary-alcohol, secondary-alcohol, diol dehydrogenase activities. The results showed that all ADH activities in the cell-free extract of *T. guaymasensis* were NADP$^+$-dependent. Other suitable oxidizers could be used. Diverse ADH activities were seen and activity was detectable using each of the alcohol substrates mentioned above. The highest ADH activity (18.9 U mg$^{-1}$) was seen when 2-butanol was used as the assay substrate.

Purification of *T. guaymasensis* ADH.

Considering the possibility of multiple ADHs in the cell-free extract, the ADH activities were traced using 2-butanol, 1-butanol and glycerol as assay substrates during the purification procedure. ADH activities appeared in a single peak from all liquid chromatography columns used and the ratio of ADH activities among 2-butanol, 1-butanol and glycerol (200:10:0.5-1) was almost constant until the enzyme was purified to homogeneity by a four-step procedure using fast protein liquid chromatography (FPLC). The ADH in *T. guaymasensis* was partially eluted during the loading of the sample onto the DEAE-Sepharose column, suggesting the enzyme might have higher isoelectric point (pI) value, which was confirmed later by theoretical pI calculated from the deduced amino acid sequence. The enzyme could be completely eluted by using buffer A, and such property significantly facilitated the separation of the ADH from other proteins in the cell-free extract. Subsequently, the ADH activity was eluted out as a predominant single peak in the following chromatography. The purified ADH after the gel-filtration chromatography had a specific activity of 1149 U mg$^{-1}$ with the yield of 17% (Table 3). The native molecular mass was determined using gel filtration to be 135±5 kDa. The SDS-PAGE analyses of the purified enzyme yielded a single band with a molecular weight of 40±1 kDa Thus, the purified ADH appeared to be a homotetramer. \\

Catalytical and Physical Properties of the Purified *T. guaymasensis* ADH.

*T. guaymasensis* ADH was NADP$^+$-dependent. The optimal pH of the enzyme was found to be 10.5 for the 2-butanol oxidation and 7.5 for the 2-butanone reduction, respectively, although other pHs could be used. The purified enzyme from *T. guaymasensis* was thermophilic and its activity increased along with the elevated temperatures up to 95° C., as tested. The oxygen sensitivity of the enzyme was monitored by the residual activity after exposure to the air at room temperature. The enzyme was oxygen sensitive although it was more resistant to oxidation than that of iron-containing ADHs. The time ($t_{1/2}$) required to decrease 50% of the full activity upon exposure to the air was about 4 hours, and such inactivation was slightly decreased in the presence of 2 mM dithiothreitol. The thermostability of the purified enzyme was investigated by determining its residual activities when the enzyme samples were incubated at 80 and 95° C., respectively. The $t_{1/2}$ values at 95 and 80° C. were determined to be 24 and 70 hours, respectively, revealing its hyperthermostable feature.

The substrate specificity of the purified enzyme was determined using a set of alcohols, aldehydes and ketones (Table 4). In the oxidation reactions, *T. guaymasensis* ADH was able to transform a broad range of primary alcohols but not oxidize methanol. Moreover, the purified enzyme showed higher activities using secondary alcohols such as 2-butanol and 2-pentanol as substrates, suggesting that the enzyme is preferentially a primary-secondary ADH, although substrate specificity is not limited to primary and secondary alcohols. The enzyme showed no activity on $_L$-serine and $_L$-threonine. In the reduction reactions, the enzyme exhibited the ability of reducing various aldehydes and ketones. In particular, the purified enzyme from *T. guaymasensis* could not oxidize acetoin to diacetyl, indicating the reduction of diacetyl to acetoin may be irreversible.

TABLE 4

Substrate specificity of *T. guaymasensis* ADH

| Alcohols (50 mM) | Relative activity (%) | Aldehydes or ketones (6 mM) | Relative activity (%) |
|---|---|---|---|
| Methanol | 0 | Acetone | 149.4 ± 2.8 |
| Ethanol | 5.7 ± 0.3 | 2-Butanone | 100 ± 3.4[b] |
| 1-Propanol | 15.1 ± 0.3 | 2-Pentanone | 86.2 ± 3.1 |
| 1-Butanol | 5.1 ± 0.2 | Acetoin | 93 ± 3.2 |
| 1-Pentanol | 0.8 ± 0.2 | Diacetyl | 134.8 ± 5.9 |
| Glycerol | 0.2 ± 0.1 | Acetaldehyde | 36 ± 4.2 |
| 2-Propanol | 88 ± 1.1 | Butyraldehyde | 112.4 ± 11.9 |
| 2-Butanol | 100 ± 2.2[a] | | |
| 2-Pentanol | 66.3± | | |
| 1,2-Butanediol | 25.6 ± 2.3 | | |

TABLE 3

Purification of ADH from *T. guaymasensis*

| Purification Steps | Total protein (mg) | Total activity (U) | Specific activity (U mg$^{-1}$) | Purification fold | Yield (%) |
|---|---|---|---|---|---|
| Cell-free extract | 3718.5 | 1.2 × 10$^5$ | 33.7 | 1 | 100 |
| DEAE-Sepharose | 446.8 | 6.3 × 10$^4$ | 142 | 4.2 | 52 |
| Hydroxyapatite | 58.7 | 5.7 × 10$^4$ | 970 | 28.8 | 47 |
| Phenyl-Sepharose | 30.7 | 3.4 × 10$^4$ | 1099 | 32.6 | 28 |
| Gel filtration | 17.4 | 2.0 × 10$^4$ | 1149 | 34.1 | 17 |

TABLE 4-continued

Substrate specificity of *T. guaymasensis* ADH

| Alcohols (50 mM) | Relative activity (%) | Aldehydes or ketones (6 mM) | Relative activity (%) |
|---|---|---|---|
| 1,3-Butanediol | 35.4 ± 1.1 | | |
| 2,3-Butanediol | 78.7 ± 3.4 | | |
| 1,2-Pentanediol | 4.7 ± 0.3 | | |
| 2,4-Pentanediol | 9.2 ± 0.1 | | |

[a]The relative activity of 100% in alcohol oxidation means 1144 ± 24 U mg$^{-1}$.
[b]The relative activity of 100% in aldehyde/ketone reduction means 223 ± 7.6 U mg$^{-1}$.

The apparent $K_m$ value for the coenzyme NADPH was over forty times lower than that for the coenzyme NADP$^+$ (Table 5). The specificity constant $k_{cat}/K_m$ for NADPH as electron donor in the ketone reduction (14,363,000 s$^{-1}$M$^{-1}$) was about 4.3 times higher than that of NADP electron acceptor in the oxidation of corresponding alcohol (3,333,000 s$^{-1}$M$^{-1}$). These catalytic properties suggest that the enzyme could play an important role in the oxidation of NADPH rather than the reduction of NADP$^+$ in vivo. However, apparent $K_m$ value for 2-butanone (0.31 mM) was close to that of 2-butanol (0.38 mM) and the specificity constant $k_{cat}/K_m$ for 2-butanone (613,000 s$^{-1}$ M$^{-1}$) was about one third of that for 2-butanol (2,192,000 s$^{-1}$ M$^{-1}$). To catalyze the reduction of diacetyl to 2,3-butanediol via acetoin, the enzyme had higher catalytic efficiency for diacetyl and lower catalytic efficiency for 2,3-butanediol, suggesting its possible roles involving in the reduction of diacetyl to acetoin or 2,3-butanediol (Table 5).

TABLE 5

Kinetic parameters of *T. guaymasensis* ADH

| Substrate (mM) | Co-substrate (mM) | Apparent Km (mM) | Apparent Vmax (U mg$^{-1}$) | kcat (s$^{-1}$) | kcat/Km (s$^{-1}$M$^{-1}$) |
|---|---|---|---|---|---|
| 2-butanol | NADP$^+$ (0.4) | 0.38 | 1250 | 833 | 2,192,000 |
| (2R,3R)-(−)-2,3-butanediol$^a$ | NADP$^+$ (0.4) | 15.2 | 1111 | 740 | 49,000 |
| (2S,3S)-(+)-2,3-butanediol$^a$ | NADP$^+$ (0.4) | 246 | 769 | 512 | 2082 |
| meso-2,3-butanediol$^a$ | NADP$^+$ (0.4) | 19.3 | 1428 | 952 | 49,000 |
| NADP$^+$ | 2-butanol (11) | 0.4 | 2000 | 1333 | 3,333,000 |
| 2-butanone | NADPH (0.2) | 0.31 | 285 | 190 | 613,000 |
| R/S-acetoin | NADPH (0.2) | 0.32 | 213 | 142 | 444,000 |
| Diacetyl | NADPH (0.2) | 0.21 | 303 | 202 | 962,000 |
| NADPH | 2-butanone (3) | 0.011 | 237 | 158 | 14,363,000 |

$^a$Various concentrations for (2R,3R)-(−)-2,3-butanediol (0, 2.7, 5.4, 8.1, 10.7, 16, 21.2, 26.5 and 51.7 mM), (2S,3S)-(+)-2,3-butanediol (0, 11, 22, 27.5, 44, 55, 82.5 and 110 mM) and meso-2,3-butanediol (0, 2.7, 5.4, 8.1, 10.7, 16, 21.2, 26.5 and 51.7 mM) were used for the determination of kinetic parameters.

Reduction of 2-Butanone Coupled with NADPH Regeneration

Enzymes resistant to solvent inactivation are of great interest from scientific and practical points of view. The solvent tolerance of *T. guaymasensis* ADH was examined on the oxidation of 2-butanol and the reduction of 2-butanone by adding methanol into the assay mixtures. The purified enzyme did not oxidize methanol. The enzyme retained almost its full activity when the concentration of methanol was up to 5% (v/v). When the concentration of methanol was 30% (v/v) in the assay mixture, the enzyme activity remained about 40% of full activity on both oxidation and reduction, indicating that the enzyme had the outstanding solvent tolerance.

The solvent-tolerant feature of *T. guaymasensis* ADH made it feasible to regenerate the coenzyme NADPH using the co-substrate isopropanol in excess amounts (500 mM). A gas chromatography method was developed to determine the reactants which had the following retention times: 1.33 min for isopropanol, 2.26 min for 2-butanone, 2.51 min for 2-butanol. Driven by isopropanol (500 mM), the addition of 50 mM 2-butanone could result in the production of 45.6 mM 2-butanol, while the control without the addition of isopropanol produced 2-butanol in a low concentration similar to that of coenzyme added (1 mM). The transfer yield was about 91%. Similar results were also obtained when 2-pentanone was used to replace 2-butanone using the same reaction system.

TABLE 6

Exemplary substrates that can be used for the re-generation of co-enzyme for the enzymatic reaction(s)*

| Alcohol as co-substrate | Desired | Non-desired |
|---|---|---|
| Methanol | | |
| Ethanol | Inexpensive; Primary alcohol; Miscible with water; The oxidized product acetaldehyde is volatile | Acetaldehyde may inhibit the reaction |
| 1-propanol | | |
| 2-propanol | Inexpensive; secondary alcohol; Miscible with water; | Acetone may inhibit the reaction |

TABLE 6-continued

Exemplary substrates that can be used for the re-generation of co-enzyme for the enzymatic reaction(s)*

| Alcohol as co-substrate | Desired | Non-desired |
|---|---|---|
| 1-butanol | | |
| 2-butanol | | |
| 1-pentanol | | |
| 2-pentanol | | |
| 3-pentanol | Suitable for aqueous/organic two-phase system | |
| 2-hexanol | | |
| 2-heptanol | | |
| 1-octanol | | |
| Cyclooctanol | Suitable for aqueous/organic two-phase system | |
| 2-methyl-1-butanol | | |
| 5-amino-1-pentanol | | |
| 2-methyl-1-butanol | | |
| 3-methyl-1-butanol | | |
| 2-methyl-2-butanol | | |
| 2,2-dimethyl-1-propanol | | |

*Generally, all alcohols that the enzyme can oxidize could be used as co-substrate for coenzyme regeneration. However, as the skilled person will appreciate, the practical choice will depend on such factors as the substrate, products, reaction rate, yield, and cost.

Stereoselectivity of *T. guaymasensis* ADH.

To investigate the stereoselectivity of *T. guaymasensis* ADH, two methods based on GC equipped with a chiral column were developed to efficiently separate substrates and products of the reactions, transformations between acetoin and 2,3-butanediol or between 2-butanone and 2-butanol. In the interconversion between acetoin and 2,3-butanediol, the retention times of their isomers were 3.6 min for (3R)-acetoin, 4.2 min for (3S)-acetoin, 9.1 min for (2S,3S)-(+)-2,3-butanediol, 9.4 min for (2R,3R)-(−)-2,3-butanediol, and 10.2 min for meso-2,3-butanediol. The enzyme showed higher oxidation activities on the (2R,3R)-(−)-2,3-butanediol and meso-2,3-butanediol than on the (2S,3S)-(+)-2,3-butanediol, indicating the enzyme predominantly oxidized R-hydroxyl group of 2,3-butanediol and minorly functioned on S-hydroxyl group. When meso-2,3-butanediol was oxidized, (3S)-acetoin was the predominant product with the enantiomeric excess (ee) of 88%, while oxidation of (2R,3R)-2,3-butanediol resulted in the production of (3R)-acetoin with extremely high specificity (94% ee). With respect to the reduction reaction, the racemic R/S-acetoin was used since either R- or S-acetoin was not commercially available. Consistently, the reduction of racemic R/S-acetoin formed (2R,3R)-2,3-butanediol (presumely from R-acetoin) and meso-2,3-butanediol (presumely from S-acetoin) with extremely high specificity [>99% ee over (2S,3S)-(+)-2,3-butanediol]. In addition, the kinetic parameters also confirmed that the enzyme had higher $K_m$ value for (2S,3S)-(+)-2,3-butanediol than (2R,3R)-(−)-2,3-butanediol or meso-2,3-butanediol (Table 5).

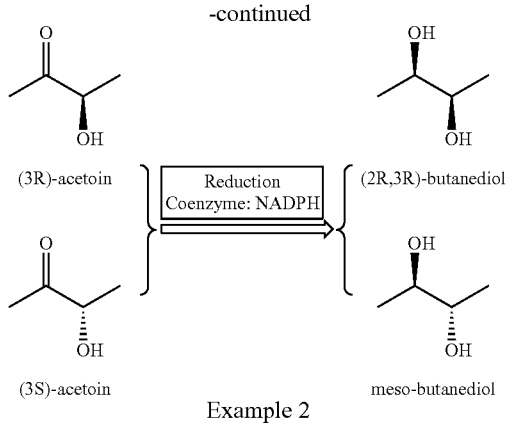

Example 2

Sequence Analysis of TgADH and Recombinant Production

Materials and Methods

All the chemicals in this research were purchased from commercially available sources (Table 7).

TABLE 7

Major chemicals used in this research

| Chemicals* | Corporation |
| --- | --- |
| Agarose | Fermentas Canada Inc. (ON, Canada) |
| Acrylamide-Bisacrylamide-Solution | MP Biomedicals (OH, USA) |
| BIO-RAD Protein Assay | Bio-Rad Laboratories, Inc. (ON, Canada) |
| 5-bromo-4-chloro-3-indolyl-beta-D-galactopyranoside | Fermentas Canada Inc. (ON, Canada) |
| Dithiothreitol | Fisher scientific company (ON, Canada) |
| Isopropyl β-D-1-thiogalactopyranoside | Fermentas Canada Inc. (ON, Canada) |
| β-nicotinamide adenine dinucleotide (NADP) | Sigma-Aldrich Canada Ltd. (ON, Canada) |
| β-nicotinamide adenine dinucleotide; disodium salt (NADPH) | Sigma-Aldrich Canada Ltd. (ON, Canada) |

*all other chemicals not mentioned here were of high technical grade and obtained from Sigma-Aldrich Canada Ltd. (Oakville, Ontario) or Fisher scientific company (Ottawa, Canada).

Restriction enzymes and DNA ladders for molecular cloning and recombinant plasmid construction enzymes were commercially available (Table 8), and were used according to the manufacture's instructions. Major instruments used were listed in Table 2-3.

TABLE 8

Major chemicals for molecular biology work

| Restriction enzymes and reagents* | Corperation |
| --- | --- |
| GeneRuler 100 bp DNA Ladder | Fermentas Canada Inc. (Burlinton, ON, Canada) |
| KOD Hot Start DNA Polymerase | EMD Chemicals, Inc. (NJ, USA) |
| PCR Gel Extraction Kit | Qiagen (ON, Canada) |
| Perfect DNA 1 kb DNA Ladder | Novagen (WI, USA) |
| Restriction DNA restriction endonuclease | Fermentas Canada Inc. (ON, Canada) |
| Taq Polymerase | Fermentas Canada Inc. (ON, Canada) |
| T4 DNA Ligase | Fermentas Canada Inc. (ON, Canada) |

*All other chemicals not mentioned above were obtained from Sigma-Aldrich Canada Ltd. or Fisher scientific company (ON, Canada).

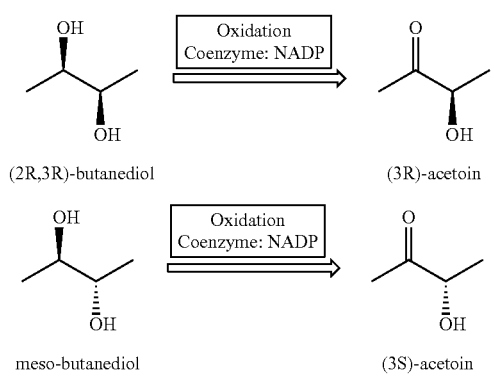

TABLE 9

Major instruments used in this research

| Instrument | Corporation |
| --- | --- |
| Agarose gel electrophoresis chamber | Bio-Rad Laboratories, Inc. (ON, Canada) |
| Acrylamide-Bisacrylamide-Solution | MP Biomedicals (OH, USA) |
| Centrifuge (Allegra 21R Centrifuges) | Beckman Coulter (ON, Canada) |
| Centrifuge (Sorvale ® RC6-Refrigerated Superspeed Centrifuges) | Mandel Scientific Company Inc. (ON, Canada) |
| FPLC | Amersham Biotech (QC, Canada). |
| FluorChem 8000 Chemiluminescence and Visible Imaging System | Alpha Innotech Corporation (CA, USA) |
| Incubation shaker | New Brunswick Science (NJ, USA) |
| Incubator | Fisher scientific company (ON, Canada) |
| Microscope | Fermentas Canada Inc. (ON, Canada) |
| Protein gel chamber | Bio-Rad Laboratories, Inc. (ON, Canada) |
| Spectrophotometer (GENESYS 10 UV) | VWR Canlab (ON, Canada) |
| Table centrifuge | Eppendorf (ON, Canada) |
| Thermal-PCR-cycler TC-312 | Techne incorporated (NJ, USA) |
| Vortex | Fisher scientific company (ON, Canada) |
| Waterbath | Fisher scientific company (ON, Canada) |

Microorganisms

Microorganisms used for this study are listed below:
*Thermococcus guaymasensis* DSM 11113™ was obtained from Deutsche Sammlung von Mikroorganismen und Zellkulturen, Braunschweig, Germany. *E. coli* DH5α [(supE44 ΔlacU169 φ80 lacZΔM15) hsdR17 recA1gyrA96 thi-1 relA1] (BRL, CA, USA). *E. coli* BL21(DE3) [B F-ompT hsdSB (rB-mB-) gal dcm (DE3)] (Novagen, Wis., USA). *E. coli* BL 21(DE3)-RIL [F-, ompT, hsdSB (rB-mB-) gal dcm lacY1, pRARE (CamR)] (Stratagene, Calif., USA).

Cultivation Media and Growth Conditions

For the growth of *E. coli*, 2YT-medium was used. All media were autoclaved for 30 minutes at 121° C.

2YT medium (per liter): Tryptone 16 g, NaCl 5 g, Yeast extract 10 g. Deionized water was added to 1 L. The solution was autoclaved for 30 minutes at 121° C.

SOB medium (per liter): Bacto-peptone 20 g, Bacto-yeast extracts 5 g, NaCl 5.8 g, KCl 0.19 g. Adjust the pH to 7.5 with KOH. After autoclave and cool down, 2.5 ml autoclaved 1M $MgCl_2$ and 2.5 ml autoclaved 1M $MgSO_4$ were added.

Medium for *T. cyuaymasensis* (Per Liter)

KCl 0.32 g; $MgCl_2 \cdot 2H_2O$ 2.7 g; $MgSO_4 \cdot 7H_2O$ 3.4 g; $NH_4Cl$ 0.25 g; $CaCl_2 \cdot 2H_2$ 0.14 g; $K_2HPO_4$ 0.14 g; $Na_2SeO_3$ 100 μl (100 mg/ml); $NiCl_2 \cdot 6H_2O$ 100 μl (100 mg/ml); NaCl 18 g; Bact-yeast extract 5 g; Tryptone-peptone 5 g; Trace mineral 10 ml; Resazurin 2 ml (500 mg/L); and Glucose 5 g. Adjust the pH to 7.0, dispensed 50 ml medium to a 160 ml serum bottle. After autoclave the medium turned to pink. When it cooled down, the medium was degassed and pressured with nitrogen gas. Then 0.14 ml 15% cystein and 0.17 ml 7% $Na_2S$ were added to each bottle. After incubating the medium at 88° C. for 5 min, the medium turned to light yellow and it was ready for use.

Stock Solutions of Antibiotics and Reagents

Ampicillin: 1 g/ml in deionized water. Filter sterilized through 0.2 μm filter membranes (Corning N.J., USA). Stored at −20° C. Used at 1 mg/ml.

Kanamycin: 500 mg/ml in deionized water. Filter sterilized through 0.2 μm filter membranes. Stored at −20° C. Used at 0.5 mg/ml.

IPTG (Isopropyl β-D-1-thiogalactopyranoside): 0.1M in deionized water. Filter sterilized through 0.2 μm filter membranes. Stored at −20° C.

X-gal (5-bromo-4-chloro-3-indolyl-beta-D-galactopyranoside): Dissolved in dimethylformamide at 20 mg/ml. Stored at −20° C. in dark.

Cell Cultivation

Cell cultivation was carried out either in shake-flasks with baffles or in solidified agar plates with the media composition as described in section 2.3.3.

*E. coli* Cultivation

*E. coli* strains were grown in 2YT medium at 37° C., 140-200 rpm, in a volume ranging from 500-1000 ml in shake flasks with baffles by inoculating one colony from agar plate or with previous culture in a ratio of 1:100 or 1:50 (1-2% v/v). The ratio between the volume of the media and the volume of the shake flask was 1:5 (e.g. 100 ml media was used for cultivation in a shake flask having a volume of 500 ml). For isolation of vector material or screening of clones, *E. coli* strains harboring plasmids were grown overnight at 37° C. in a shaker incubator at 140-160 rpm containing necessary antibiotic in the media composition.

*T. guyamsensis* Cultivation

*T. guyamsensis* was cultured at 88° C. in the medium as described previously (Canganella et al. 1998) with modifications that elemental sulfur and HEPES were omitted.

Conservation and Storage of Microbiological Strains

For long-term storage of *E. coli* cells, cryo-cultures were made with glycerol at −20° C. or −80° C. This method was used for preparation of competent cells as well as preparing stock cultures of *E. coli* cells harboring either pET30avectors or pET30arecombinants. For this, a single colony was picked up from 2YT-agar plate and inoculated into a 5 ml liquid 2YT medium containing appropriate antibiotic if required, incubated at 37° C. on a shaker with vigorous shaking until the $OD_{600}$ reached 0.6-0.8. Then 0.8 ml of the culture was removed and transferred to a sterilized cryo-vial, and 0.2 ml of 50% glycerol was added. The culture was mixed well and stored at −20° C. Or cells with glycerol (10%) were frozen in liquid nitrogen quickly and then stored for long-term at −80° C.

Preparation for Competent Cells

*E. coli* DH5α High Efficiency Competent Cells

For construction of the cloning vector pGEM-Teasy carrying the TGADH coding gene, the *E. coli* DH5α high efficiency competent cells were prepared following the standard protocol. *E. coli* DH5α cells were amplified into 250 ml SOB medium and grew at 18° C. (room temperature) and were shaken with 100-110 rpm until a cell density of 0.6 $OD_{600nm}$ was reached.

After harvesting at 4,000 rpm for 10 minutes at 4° C., the pellet cells were re-suspended in 80 ml pre-cooled transformation buffer (10 mM PIPES, 10 mM CaCl$_2$, 250 mM KCl, 100 mM MnCl$_2$, pH 6.7) slightly, followed by incubation for another 10 minutes on ice. After centrifugation, the pellet was carefully re-suspended in 18.6 ml ice-cold transformation buffer and then 1.4 ml DMSO was slowly added with gentle stirring to obtain a final concentration of DMSO at 7% which is important for transformation efficiency and long term storage. Cells were incubated for another 10 minutes on ice and dispensed 100 ul each in 1.5 ml centrifuging tube. The tubes were frozen immediately in liquid nitrogen, and stored at −80° C. (the cells are viable for at least 4 months).

E. coli BL 21 (DE 3) and E. coli BL 21 (DE 3)-RIL Competent Cells

E. coli BL 21 (DE 3) or BL 21 (DE 3)-RIL single colonies (2-3 mm) from overnight growth on 2YT-agar-plate could be taken as inocula into 5 ml 2YT medium without antibiotics and incubated with shaking in a small scale at 37° C. for 3-4 hours. Then the bacteria could be amplified into 100 ml 2YT medium. The cells grew at 37° C. with shaking at 100-110 rpm until a cell density of OD$_{600nm}$ 0.6 was reached. Then the cells were centrifuged at 4,000×g for 10 minutes at 4° C. and the supernatant was then discarded. The cells were then re-suspended in 10 ml pre-cooled 0.1M CaCl$_2$ slightly, followed by incubation for another 10 minutes on ice. After washed using 0.1M CaCl$_2$ again, cells were incubated on ice for at least 30 minutes. Finally, the pellet was re-suspended carefully using 2 ml ice-cold 0.1M CaCl$_2$ solution and 200 μl 50% glycerol with gentle stirring. Cells were then dispensed in 1.5 ml centrifuging tubes at 100 μl/tube and were frozen immediately in liquid nitrogen, and finally stored at −80° C.

Gene Cloning for TgADH

Since the genome sequence of T. guaymasensis is unknown, the TgADH encoding gene was isolated and sequenced before over-expression of enzyme in mesophilic host. The PCR amplified fragments were obtained using genomic DNA as template.

Preparation of T. guaymasensis Genomic DNA

The total genomic DNA from T. guaymasensis was isolated by lysis of the cells. The cells harvested and resuspended in TE buffer (10 mM Tris-HCl, 1 mM EDTA, pH 8.0), which was followed by the addition 0.5 ml of 10% SDS and 5 mg of protease K and incubation at 60° C. for 30 minutes. To this, 0.5 ml of 3 M sodium acetate was added and stored on ice for 1 hour. This was centrifuged at 10,000×g for 10 min. The supernatant was transferred to a fresh tube and DNA was isolated from the mixture using the solution of phenol, chloroform and isoamyl alcohol (25:24:1). Participated by 100% isopropanol and washed by 75% ethnol, the DNA was finally resuspended in 0.2 ml TE buffer. DNA concentrations of samples were quantified using NanoDrop Spectrophotometer (NanoDrop Technologies, DE, USA), and purified DNA was stored at −20° C.

Cloning of the Entire Gene Encoding TgADH

The coding gene of TgADH was cloned from the T. guaymasensis genomic DNA isolated from the T. guaymasensis cells directly using Polymerase Chain Reaction (PCR) performed by a thermal cycler termed TC-312 (Techne incorporated, NJ, USA), each reaction had a volume of 25 μl and all the reagents were added following the standard conditions recommended by the suppliers. An error-free amplification was expected to protect occurrence of accidental mutations in the process of PCR, which could finally lead to an inactive recombinant protein. The Taq-polymerase possesses no "proof-reading activity" and therefore the appearance of mutations during the process of amplification cannot be avoided. So the amplification of the PCR-products for cloning in the expression vectors was carried out by the proof-reading polymerase.

Unless otherwise stated, PCR was performed using KOD Hot Start DNA Polymerase, and all the reaction parameters were set as conditions suggested by the suppliers. Two bioinformatic tools were used for primer designing; software DNASTAR was used to predict the potential locations of the primers and GENERUNNER (version 3.01 was used to optimize the parameters of oligonucleotides. After typing in the nucleic acids sequence in DNASTAR, major properties of the primers were set as the following: primer length between 18-30 bp, melting temperatures (Tm) between 45-65.degree. C. The software then calculated the locations of proper forward and reverse primers that were consequently optimized by GENERUNNER. The optimal primer pairs had similar melting temperatures (difference.ltoreq.3.degree. C.) and harbored no hairpin loops, dimmers, bulge loops or internal loops.

Analytical as well as preparative gel electrophoresis of double-stranded DNA fragments were performed in 0.5-1.5% agarose gels supplemented with ethidium bromide (final concentration 0.5 μg/ml). The agarose was dissolved in 1×TAE buffer (Diluted from the 50× stock solution: Tris base 1M, Glacial acetic acid 57.1 ml/L, EDTA 50 mM, pH 8.0). Before loading on the gel, the DNA samples were mixed with 6×DNA loading buffer. For determination of fragment size and concentration estimation, a defined amount of DNA size marker was included. DNA bands were visualized and graphed by FluorChem 8000 Chemiluminescence and Visible Imaging System (Alpha Innotech Corporation, San Leandro, Calif., USA). For preparative methods such as cloning of DNA fragments, all the PCR products were purified with the PCR Purification kit (Qiagen, ON, Canada).

The nucleic acids sequence encoding the N-terminal of the enzyme was obtained by PCR using both normal and degenerate primers (Table 9). The degenerated forward primer TGADHNF (SEQ ID NO: 11) was designed based on its N-terminal amino acid sequence considering the codon bias of Thermococcus kodakaraensis KOD1 while the reverse non-degenerated primer TGADHIR (SEQ ID NO: 12) was designed based on one of the internal sequences, GYHQH-SGGMLAGW (SEQ ID NO: 26) by mass spectrometry and the conserved nucleotide sequence in the gene encoding the ADH from Thermoanaerobacter brockii. Both sequence analysis using bioinformatics tool BLAST, as well as the matching of the amino acid sequence finally confirmed the nucleic acids sequence. For the further cloning of the downstream sequence till the coding sequence of C-terminal of T. guaymasensis ADH, a process termed Inverse PCR was applied. Firstly, the isolated genomic DNA was digested by the DNA restriction enzyme that was not included in the known DNA sequence, including EcoRI, HindIII and Bam HI, respectively. After incubation at 37° C. for 1-2 hours, the partially digested samples were incubated at 65° C. for half an hour to denature the enzymes. Then, the digested product was ligated to circle DNA by using T4 DNA ligase at 16° C. overnight, which was used as the template in inverse PCR. After amplification, the resulting product of inverse PCRs was sequenced by the dye-termination method using several primers designed on raw sequence information (Molecular Biology Core Facility, University of Waterloo, ON, Canada). The nucleotide sequences were analyzed with the program GENERUNNER and its deduced amino acid sequence was compared to the GenBank Data Base by BLASTP. Finally a 1.4 kb fragment amplified from the DNA template digested by Hind III was confirmed to be the one carrying the target TgADH encoding gene.

TABLE 10

Primers designed for cloning and sequencing the gene encoding T. guaymasensis ADH

| Name of primers* | Nucleotide sequence (5'-3') | | Restriction enzyme Sites (underlined) |
|---|---|---|---|
| TGADHNF | AARATGMGNGGTTTTGCAATG | (SEQ ID NO: 11) | |
| TGADHIR | GGAGTGCTGGTGATATCC | (SEQ ID NO: 12) | |
| TGMAYN01 | TCTCCTTCTCAATCCACTCG | (SEQ ID NO: 13) | |
| TGMAYC02 | GCAATAACTCCCGACTGG | (SEQ ID NO: 14) | |
| TGMAY28C01 | TGCCGAAGTAGTTGATGTTG | (SEQ ID NO: 15) | |
| TGMAY28C02 | GAGGTCAAGCAGGCGNTC | (SEQ ID NO: 16) | |
| TGJL1N1 | ATGTCNAAGGATGCGCGGT | (SEQ ID NO: 17) | |
| TGJL1N2 | ATGAGYAAGGATGCGCGGT | (SEQ ID NO: 18) | |
| TGECN | TAGAATTCATGAGCAAGATGCGCGGTTTTC (EcoRI) | (SEQ ID NO: 19) | |
| TGXHR | ACCTCGAGTCACTCCTCTATGATGACC (XhoI) | (SEQ ID NO: 20) | |

*, Primer properties such as melting temperature (Tm), GC content (GC %), primer loops and primer dimmers were evaluated by a DNA analysis tool Gene Runner (Hastings Research, Inc., Las Vegas, USA). The table indicates all the key primers used for both fragments cloning and specific amplification. The forward and the reverse primers with the restriction enzyme sites were the specific primer designed based on the confirmed sequence for the amplification of the entire TgADH encoding gene.

Data Mining

The homologues of the encoding gene sequence of TgADH and the deduced amino acid sequence were identified using the BLAST program with the default parameters. Additional sequences were retrieved from the Pfam database. Sequence alignments and phylogenetic trees were constructed by the neighbor-joining method of Clustal W with default parameters. Theoretical molecular weight was calculated using the ProtParam program at the ExPASy Proteomics Server with standard parameters. A 3-D structure of TgADH monomer was modeled using the Swiss Model server, and then the PDB file obtained was used in the PyMOL software to visualize and analyze the 3-D structure. Conserved domains (CDs) were analyzed with CD-search and Motif Search. Phylogenetic analyses were performed aligning T. guaymasensis ADH and close homologues of zinc-containing families using the program Clustal W. The primary structure analyses including the amino acid composition, theoretical molecular weight and isoelectric point (pI) was estimated using the program ProtParam™ on the ExPASy™ server. The secondary and tertiary structure prediction was performed using the SWISS-MODEL™ server. The software PyMOL™ was used to analyze and visualize the tertiary structure of T. guaymasensis ADH monomer.

Construction of the Recombinant Plasmid
Vectors Used
pGEM-Teasy, 3015 bp, $P_{T7}$, Amp® (Promega, Wis., USA)
pET-30a, 5360 bp, $P_{T7}$, Kan® (Novagen, Wis., USA)

Plasmid Isolation by the Alkaline Lysis Method

Alkaline lysis was done for plasmid isolation. The method involves 3 steps: washing with RNase solution, lysis of the cells with lysis buffer and precipitation of the plasmid DNA. A single colony was inoculated in 5 ml of 2YT medium with corresponding antibiotics and grew overnight at 37° C. The culture was harvested by centrifugation for 10 min at 5,000×g and the pellets were suspended by vortexing in 400 µl of ice-cold Solution A (Glucose 50 mM, EDTA 10 mM, Tris-HCl 25 mM, pH 8.0, RNase A 100 µg/ml. To the suspension, 800 µl of Solution B (NaOH 0.2 M, 1% SDS) was added and mixed by inverting the tube several times slightly. After incubation on ice for 5 min, 600 µl of ice-cold Solution C (Sodium acetate, 3 M) was added and mixed by inverting the tube. After the centrifugation at 4° C., the supernatant containing the plasmid DNA was taken and DNA participated by 100% ethanol and collected by centrifugation. The isolated plasmid DNA was then suspended in 50-100 µl TE buffer.

DNA Restriction Digestion

Digestion of the DNA with restriction endonucleases was performed in the buffer supplied with the restriction enzyme and in accordance with the suppliers' recommendations for temperatures and duration of digestion. Mostly digestion was done for 2-4 hours using 10-20 U of the enzyme for 0.5-1.5 µg DNA. The digestion reaction was incubated at 37° C. After completion of the restriction digestion the reaction mixture was analyzed by agarose gel electrophoresis. For preparative restriction digestion e.g., DNA fragments to be inserted into the vector, reaction mixture was purified with the PCR Purification kit (Qiagen, ON, Canada) and quantified by agarose gel electrophoresis.

Ligation of DNA Fragments

To keep a high efficiency of the ligation, all the restriction endonucleases selected in this research could provide the "sticky end", either 5' or 3' extension. For successive ligation reactions of the inserts to vectors, a 10 µl reaction volume was used with 3:1 molar ratio of insert to vector, 1 U of T4 DNA Ligase and 1 µl 10× Ligation buffer (Fermentas, ON, Canada). The ligation mixture was incubated at 16-20° C. overnight. After ligation reaction was completed, the mixture was used for transformation.

Transformation and Selection

As T. guaymasensis ADH coding gene preferred a very different codon usage compared to the mesophilic host E. coli, higher expressed gene tend to have a greater degree of codon bias. To overcome this, confirmed by sequencing, the isolated recombinant plasmids carrying TgADH coding gene were transformed into both *E. coli* BL21 (DE3) and the codon-plus *E. coli* BL 21-RIL expression strains. Transformation of the plasmid to *E. coli* host cells followed the standard heat shock method. When *E. coli* competent cells with the constructed plasmids were subjected to 42° C. heat, a set of heat shock genes would be expressed which aid the bacteria in surviving at such temperatures that was necessary for the uptake of foreign DNA. In heat shock method, 10 µl of the ligation mixture was added to 100 µl competent cells, after incubation on ice for 30 minutes, a heat shock was given at 42° C. for 90 seconds followed by a second incubation on ice for 5 minutes. To this, 300 µl of blank 2YT medium was added and regeneration was done at 37° C. for 0.5 to 1 hour. The transformation mixture was plated onto 2YT agar plates containing appropriate antibiotic for selection and incubated at 37° C. overnight.

Normally the vector molecule carries a gene whose product confers a selectable or identifiable characteristic on the host cell, or alternatively, one gene is disrupted when new DNA is inserted into a vector, and the host cell does not display the relevant characteristic. pGEM-Teasy and pET-30a plasmids contained gene giving resistance to ampicillin and kanamycine, respectively, which the intended recipient *E. coli* strain is sensitive to. For the construction of expression vector pET-30a-Tgadh, a final concentration of 50 mg/ml kanamycine was added to the medium as the resistance selection, while for the pGEM-Teasy cloning vector, a blue-white selection together with the ampicillin resistance was used. The blue-white selection is a method of differentiating transformants that carry the vector-insert construct to those that do not carry any insert by using X-Gal (5-bromo-4-chloro-3-indolyl-[beta]-D-galactopyranoside) and IPTG (Isopropyl [beta]-D-thiogalactopyranoside) as selection markers. After transformation, host cells were plated on 2YT agar containing X-Gal (80 µg/ml 2YT agar), IPTG (final concentration 0.05 mM) along with ampicillin (100 µg/ml 2YT agar). The plates were incubated at room temperature until the transformation mixture had absorbed into the agar. After that, the plates were inverted and incubated at 37° C. overnight followed by a second incubation at 4° C. for 5-6 hours. This cold incubation enhances blue color development and thereby facilitates differentiation between blue colonies and white colonies.

Biological Deposit

A sample of *E. coli* strain BL21 codon plus RIL cells transformed with the pET30a-TgADH expression construct (for expressing the wild-type TgADH) was deposited on Sep. 22, 2009 with the International Depositary Authority of Canada (International Depositary Authority of Canada, National Microbiology Laboratory, Public Health Agency of Canada, 1015 Arlington St., Winnipeg, Manitoba, Canada R3E 3R2) and assigned accession number 220909-01.

Optimization of Growth Condition for the Recombinant *E. coli*

For expression of recombinant ADH gene in *E. coli*, plasmid Tgadh-pET-30a was transformed into *E. coli* BL21 (DE3) and transformants were grown in 2YT medium at 37° C. before induction. The recombinant TgADH was expressed driven by the T7-lac promoter and the recombinant enzyme was obtained in the periplasmic space when IPTG was added. Both the concentration of the inducer as well as the growth phase of recombinant cells at which it was added affected the final yield of the protein. To optimize the yield, inducer IPTG was added in the exponential phase when $OD_{600}$ of the cell culture reached 0.4-1.0, whereas an ideal yield with high activity presented when the cell density reached $OD_{600}$ 0.8.

The optimum concentration of the inducer was detected by amount of recombinant protein on the SDS-PAGE. The culture was then induced with 0.2 mM IPTG and cultivated at 30° C. for 12-16 hours prior to harvesting the cells.

Determination of Protein Concentration

Bradford method was used to measure the protein concentration of solutions using a spectrophotometer or microplate reader. This is based on the coomassie blue dye-binding assay in which a differential color change of the dye occurs in response to various concentrations of protein. The maximum absorbance of the dye shifts from 465 nm to 595 nm when binding of protein occurs and the measurements were at 595 nm. 200 µl of Bio-Rad reagent was mixed with 800 µl of protein solution, and a control was set by mixing 200 µl of Bio-Rad reagent with 800 µl pure water. Since the absorption is proportional to the protein quantity, the concentration of the protein solution can be determined over a linear calibration curve. The calibration curve was obtained with known protein concentrations of standard protein bovine serum albumin (BSA, albumin fraction V) by reading the absorbance of the diluted BSA at 595 nm. The absorbance versus protein concentration curve was linear in the restricted protein concentration range (between 1 mg and 20 mg protein/ml sample solution).

Determination of Enzyme Activity

The activity of ADH was determined spectrophotometrically by measuring the rate of consumption of the cofactor NADPH. The in vitro enzyme assays were anaerobically at 80° C. by measuring the ethanol-dependent reduction of NADP or the acetaldehyde-dependent oxidation of NADPH at 340 nm. Unless specifically stated, the enzyme assay was carried out in duplicate using the standard reaction mixture (2 ml) for ethanol oxidation, which contained 100 mM 3-(cyclohexylamino)-1-propanesulfonic acid (CAPS) buffer (pH 10.5), 90 mM butanol, and 0.4 mM NADP. For determination of reducing activity of the enzyme, the reaction mixture for acetaldehyde reduction was composed of 100 mM 4-(2-hydroxyethyl)-1-piperazineethanesulfonic acid (HEPES) buffer (pH 7.0), 0.4 mM NADPH and 90 mM acetaldehyde. The reaction was initiated by adding enzymes. One unit (U) is defined as the production of 1 µmol of NADPH per minute.

Protein Purification

Preparation for the Cell-Free Extract

All procedures for the preparation of cell-free extracts were carried out anaerobically. Frozen *E. coli* cells (5 grams, wet weight) carrying the recombinant expression vector TgADH-pET-30a were resuspended in 25 ml buffer A [50 mM Tris buffer containing 5% (v/v) glycerol, 2 mM dithiothreitol (DTT), 2 mM sodium dithionite (SDT) and 0.01 mg/ml DNase I, pH 7.8]. The cell suspension was incubated with stirring for 2 hours at 37° C. After centrifugation at 10,000×g for 30 minutes, the supernatant was collected as cell-free extract for further use.

Purification of the Recombinant TgADH

Purification of the recombinant enzyme from *E. coli* was carried out anaerobically using the FPLC system. Since the enzyme was thermostable, a step of heat precipitation was applied prior to the column. To optimize the heat treatment time, the cell free extracts were incubated at 60° C. for 0.5 hour, 1 hour and 2 hours respectively. After incubated at 60° C. for 0.5 to 1 hour, the solution turned gel-like. The denatured proteins and cell debris in the cell-crude extract were removed by centrifugation at 10,000×g for 30 min at room temperature. The supernatant containing enzyme activity were collected and pooled to a Phenyl-Sepharose column (2.6×10 cm) equilibrated with 0.8 M ammonia sulfate in buffer A. A linear gradient (0.82-0 M ammonia sulfate in buffer A) was applied at a flow rate of 2 ml/min and the ADH started to elute at a concentration of 0.4 M ammonia sulfate.

Size Exclusion Chromatography

The recombinant TgADH was purified after Phenyl-Sepharose column, while a part of sample was loaded onto the Superdex 200 gel filtration column (2.6×60 cm; Amersham Biosciences) in order to determine the molecular mass of its native form. Size exclusion chromatography on a Superdex 200 (Amersham Biosciences, USA) equilibrated in 50 mM Tris-HCl (pH 7.8) containing 100 mM KCl. Size of the native form of enzymes was calculated based on the elution volume of standard proteins (Pharmacia, NJ, USA) that contained blue dextran (molecular mass, Da, 2,000,000), thyroglobulin (669,000), ferritin (440,000), catalase (232,000), aldolase (158,000), bovine serum albumin (67,000), ovalbumin (43,000), chymotrysinogen A (25,000) and ribonuclease A (13,700).

Protein Gel Electrophoresis

The fraction containing the dominated activity was loaded to sodium dodecyl sulfate-polyacrylamide gel electrophoresis (SDS-PAGE) as described by Laemmli (Laemmli, 1970) to examine the purity and analyzed protein composition. Protein samples for SDS-PAGE were prepared by heating for 10 min at 100° C. in the presence of sample buffer (0.1M sodium phosphate buffer, 4% SDS, 10% 2-mercaptoethanol, 20% glycerol, pH 6.8). A low range molecular weight protein marker (Bio-Rad Laboratories Inc., ON, Canada; containing the bands 97 kDa, 66 kDa, 45 kDa, 31 kDa, 20 kDa, 14 kDa) was used to estimate the molecular mass of the proteins.

Characterization of Catalytic Properties

Determining Optimum pH

All the catalytic properties of native and recombinant TgADH were determined using the in vitro enzyme assay described above. The optimal pH of ethanol-dependent oxidation of native and recombinant TgADHs was determined by testing and comparing the enzyme activity at a series of pHs. Standard enzyme assay at 80° C. were applied using a set of 100 mM buffers: HEPES (pH 6.5, 7.0, 7.5 and 8.0), EPPS (pH 8.0, 8.5, 8.8, 9.0), glycine (pH 9.0, 9.5, 10.0) and CAPS (pH 10.0, 10.5, 11.0). The optimal pH of acetaldehyde-dependent reduction of native and recombinant TgADH was measured between pH 5.5 and 9.5 using the following buffers (100 mM): citrate (pH 5.5 and 6.0), PIPES (pH 6.0, 6.5 and 7.0), HEPES (pH 7.0, 7.5 and 8.0), EPPS (pH 8.0, 8.5, and 9.0), and glycine (pH 9.0 and 9.5).

Temperature Dependence and Thermostability

The effect of the temperature on the enzyme activity was examined at temperatures from 30 to 95° C. The activities were measured using standard assay conditions. Enzyme thermostability was evaluated by incubating the enzyme in sealed serum bottle at 80° C. and 95° C. respectively, and measuring the residual activities at different time intervals under the standard assay conditions.

Oxygen Sensitivity

The effect of oxygen on enzyme activity was investigated by exposing the enzyme samples in the air at room temperature and determining the residual activity after oxygen exposure. The exposure was performed in the presence or absence of DDT and SDT. The residual activities of each sample at different time intervals were tested parallelly under the standard assay conditions.

Effect of Metal Ions

Considering the low solubility of cations at alkaline environment, the effect of cations on enzyme activities was carried out only by measuring the reduction of 2-butanone optimal at a moderate pH and alcohol oxidation activity optimal at a pH higher than 10 was not measured. Metal ions were added in the enzyme assay mixture at a final concentration of 100 µM.

Results

Cloning of T. guaymasensis ADH Encoding Gene

N-terminal Sequencing of TgADH Encoding Gene

Based on the method as described above, the genomic DNA (gDNA) from T. guaymasensis strain was isolated with a high purity. The isolated gDNA had a concentration of 400 ng/µl. The isolated genomic DNA was used as the template for the amplification of ADH encoding gene directly by PCR. In previous research, native TgADH was purified and the N-terminal sequence of mature enzyme was detected to be SKMRGFAMVDF (SEQ ID NO: 27), which started from serine, indicating the presence of N-terminal methionine excision after translation. The PCR directed by primer pair TGADHNF (SEQ ID NO: 11) and TGADHIR (SEQ ID NO: 12) produced a single band on 1% agarose gel with the size of approximately 300 bp. The nucleotide sequence were confirmed by DNA sequencing and the deduced amino acid sequence of the 321 bp PCR product was applied in the BLAST tool and they aligned the N-terminal sequence of ADH from thermopiles.

The Entire Coding Gene of TgADH Obtained by Inverse PCR

The initial SDS-PAGE indicated that native enzyme purified from T. guaymasensis has a molecular weight of 40 kDa, so the complete nucleic acid sequence of TgADH gene should involved in a complete open reading frame with an approximate length of 1.1 kb, encoding a polypeptide of about 360 amino acid residues.

TABLE 11

N-terminal and internal sequences of TgADH
To amplify the upstream and downstream sequences

| Location | Sequences | |
|---|---|---|
| N-terminal[a] | SKMRGFAMVDF | (SEQ ID NO: 27) |
| Internal 1[b] | DFKPGDR | (SEQ ID NO: 28) |
| Internal 2[b] | VVVPAITPDWR | (SEQ ID NO: 29) |
| Internal 3[b] | GYHQHSGGMLAGW | (SEQ ID NO: 30) |

[a]amino-terminal sequence was determined by using Edman-degradation
[b]internal sequences were determined by using mass spectrometry To amplify the upstream and downstream sequences of the known fragment and finally get the sequence of the entire gene, an inverse PCR-based method was used. Inverse PCR uses the polymerase chain reaction, but the template for the reverse primers is a restriction fragment that has been ligated upon itself to form a circle and it has the primers oriented in the reverse direction of the usual orientation. Templates for inverse PCR were obtained from the total genomic DNA of T. guaymasensis by partial digestion of the gDNA with EcoRI, BamHI and HindIII respectively, which were not involved in the known sequence. After ligation by T4 DNA ligase, DNA samples were subjected to inverse PCR with the gene-specific primers designed from the known 300 bp sequence encoding N-terminal of TgADH. For inverse PCR using EcoRI or BamHI digested DNA as templates, non-specific bands were found in each lane after agarose gel electrophoresis; while there was one 1.4 kb specific band produced by PCR using the Hind III digested genomic DNA as template and driven by the specific primer pair TGMAYN01 and TGMAYC02. The 1.4 kb PCR product was fully sequenced by primer walking, and the alignment revealed that entire coding gene was located in the 1.4 kb fragment.

Sequence Analysis

The entire structural gene encoding TgADH was detected to be 1098 base pairs including the start codon ATG and stop codon TGA (SEQ ID NO: 1) with a deduced 365 amino acids sequence (SEQ ID NO: 2). The molecular weight was calculated to be 39527 Da. Interestingly, the nucleic acid sequence ended at two consecutive stop codons TGA and TAA, and the putative archaeal terminator sequence, TTTTTCT, found 24 bases downstream of the stop codon TGA. The downstream sequence of TgADH encoded a putative gene encoding archaeal hydrogenase. Analyzed by the on-line BLAST tool, deduced amino acid sequence of T. guaymasensis ADH showed relatively high overall identities to threonine dehydrogenase or zinc-containing ADHs from thermophilic bacteria, e.g., ADHs from Thermoanaerobacter tengcongensis MB4 (77% identity, AAM23957), Thermoanaerobacter brockii (77% identity, CAA46053), Thermoanaerobacter pseudethanolicus ATCC 33223 (77% identity, EAO63648), Thermoanaerobacter ethanolicus X514 (76% identity, EAU57308), Thermosinus carboxydivorans Nor1 (72% identity, EAX46383), and it also showed high similarity to ADH from mesophile Clostridium beijerinckii (67% identity, EAX46383). The deduced TgADH sequence was classified as zinc-related. The N-terminal region showed homology to ADH_N, the alcohol dehydrogenase GroES-like domain; while the C-terminal region belonged to NADB_Rossmann superfamily indicating the dependence of NAD(P) as coenzyme; the central domain was aligned to Tdh, $_L$-threonine dehydrogenase. The central region spanning the majority of peptides showed homology to the domain of TDH, so all three domains were classified as zinc-related. From the conserved motif comparision with its thermophilic and mesophilc counterparts, TgADH was found to be belong to the family of zinc-containing ADHs with catalytic zinc only, which was verified by motif searches that the enzyme had binding motifs of catalytic zinc only ($GHEX_2GX_5GX_2V$, residues 63-77) and coenzyme NADP ($GXGX_2G$, residues 184-189).

To better understand the catalytic mechanism of the enzyme, predicted 3-D structure of TgADH was made by PyMOL software (FIG. 11). The tertiary structural modeling of monomer of TgADH showed two typical domains. Both domains were separated by the cleft where the active site of the enzyme might be situated, which was responsible for specifically binding a substrate and catalyzing a particular enzymatic reaction. TgADH and its homologues harbored the highly conserved amino acid residues (FIGS. 14 and 15). One putative catalytic domain $G_{63}H_{64}E_{65}X_2G_{68}X_5G_{74}X_2V_{77}$ located close to N-terminal, and one coenzyme NADP-binding domain $G_{184}XG_{186}XXG_{189}$ was close to C-terminal end. In an examination of the three dimensional structure, the active site of TgADH centered around the catalytic zinc ion was close to the pocket containing the cofactor NADP indicating the cofactor binding is essential for catalysis, as observed for NAD(P)-dependent ADHs.

The amino acids sequences of TgADH and its thermophilic and mesophilic homologous were compared. The primary structural analyses revealed that the enzyme and its thermophilic homologue T. brockii alcohol dehydrogenase had higher ratio (molar fraction, >0.8% increase or decrease) for Ala, Arg, Glu, Lys and Pro but lower ratio for Asn, Gln, Leu, Ser and Met as compared to the ADH from the mesophile C. beijerinckii. In particular, the amino acid composition of TgADH had higher ratio for Arg, Pro and Tyr but lower ratio for Ala, Asn and Val than that of the ADH from the T. brockii.

The 14 most frequently used codons (greater than 2.7%) accounted for 58% of the amino acid residues in T. guaymasensis, reflecting its abundant tRNA types (Peretz et al., 1997). Additionally, the codon usage pattern for the TgADH coding gene was analyzed. Of the 61 sense codons, thirteen were not used in the Tgadh gene, and the comparison between codon usage of T. guaymasensis and the mesophilic bacterium E. coli indicated an obviously different codon bias between the two species, particularly, AGG (arginine), CUC (leucine), AUA (isoleucine) were rarely used in E. coli.

Construction of the Cloning and Expression Vectors

The TgADH gene is difficult to be specifically amplified from the genomic DNA due to the high GC-content, which is a common feature of archaeal genes. Before its cloning to the over-expression vector, the entire encoding gene was inserted to pGEM®-T Easy cloning vector. The PCR amplified T. guaymasensis ADH coding gene was inserted to the hanging thymidine (T) with the overhanged restriction sites of EcoRI and XhoI at the N-terminal and C-terminal respectively. The re-constructed pGEM vector was selected using the ampicillin resistance and blue-white screening. The E. coli DH 5α cells containing transformed recombinant plasmid produced colorless colonies on the agar plate.

After confirmation by sequencing, the insert from T-easy cloning vector was released by EcoRI digestion. The entire TgADH encoding gene with overhanged primer including EcoRI and XhoI restriction sites was then inserted to the EcoRI and XhoI double digested pET-30a-TgADH expression vector. The recombinant plasmid was selected from the colonies grew on 2YT agar with 50 mg/ml kanamycine, and confirmed by both colony PCR and restriction enzymes digestion. Completely digested by EcoRI, recombinant plasmids gave a 6.5 kb band on the agarose gel, 1.1 kb larger than 5.4 kb blank pET-30a vector, indicating the insertion of TgADH encoding gene.

Over-Expression of the T. guaymasensis ADH in E. coli

Driven by T7-lac promoter of pET-30a vector, over-expression of TgADH encoding gene in the mesophilic host E. coli was induced by IPTG. From 10% SDS-PAGE, a high yield of recombinant enzymes (subunits) around 50 kDa were produced in the presence of IPTG as inducer. The yield of the enzymes was better in the E. coli codon plus strain E. coli BL 21-RIL expression strains, containing the extra plasmid for rarely used tRNAs including AGG/AGA/AUA to rescue the poor expression by codon bias, however, no expression was observed in blank host strains or recombinant strains without IPTG as inducer.

Optimization of Cultivation Conditions

Recombinant E. coli cells were incubated in 2YT medium with 50 mg/ml kanamycine to an $OD_{600nm}$ 0.8 before induction, which took 3.5 to 4 hours. From small scale testing, the E. coli carrying the recombinant vector Tgadh-pET30a provided optimum yield of the recombinant enzyme when the concentration of inducer IPTG reached 0.2 mM. So, the large-scale (1-2 liters) incubation was at 37° C. to $OD_{600nm}$ 0.8, the final concentration of IPTG for induction was set at 0.2 mM.

Purification of the Recombinant T. guaymasensis ADH from E. coli

The recombinant ADH was purified from E. coli using a modified procedure. Prior to liquid chromatography, heat treatment was applied to the cell extract. Heating at 60° C. for half an hour caused no loss of enzyme activity but significantly reduced the protein concentration to 30%. The TgADH activities were dominant in the cell-free extract after heat treatment, subsequently; the recombinant TgADH was purified to homogeneity after Phenyl-Sepharose column. The purified recombinant TgADH had a specific activity of 1079

U/mg almost the same as the native protein but presented a higher yield of 81%. For size exclusion chromatography, ADH activity was assembled in a peak at 170 ml, and molecular mass of the recombinant enzyme was calculated to be 146±6 kDa. The SDS-PAGE analyses showed that both native and recombinant TgADHs had almost identical subunit size of 40±2 kDa, suggesting that enzyme was homotetramer in the native form.

Catalytic Properties of the Recombinant TgADH from *E. coli*

Figure 12:
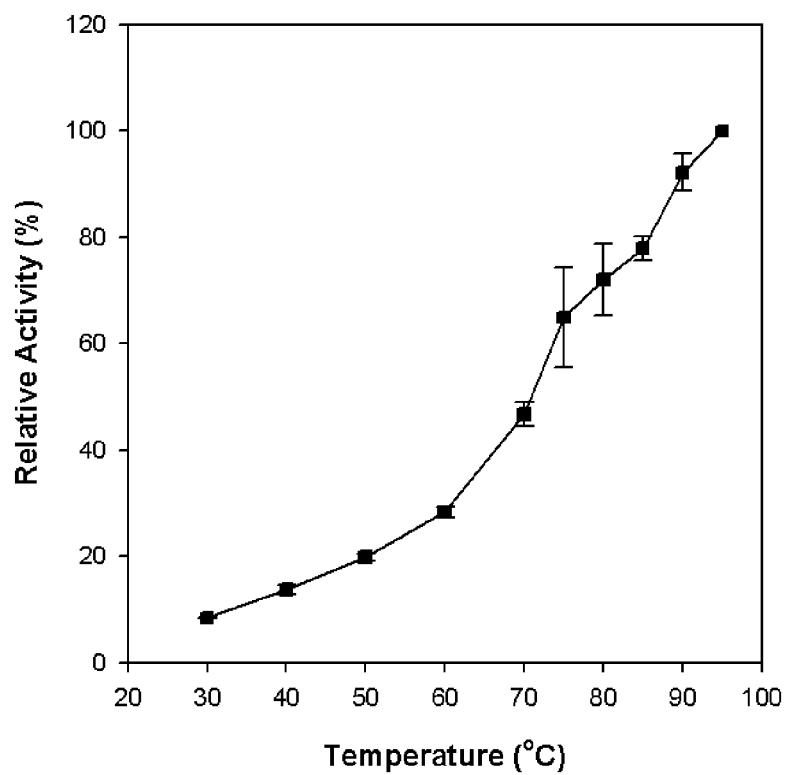
FIG. 12. Temperature dependence of the purified recombinant TgADH. Activities were measured in the standard assay conditions except varying assay temperatures from 30 to 95° C. The relative activity 100% was defined as the highest activity value achieved in this test (1533 U/mg at 95° C.). Standard deviations of the measurements are indicated using error bars.
Figure 13:
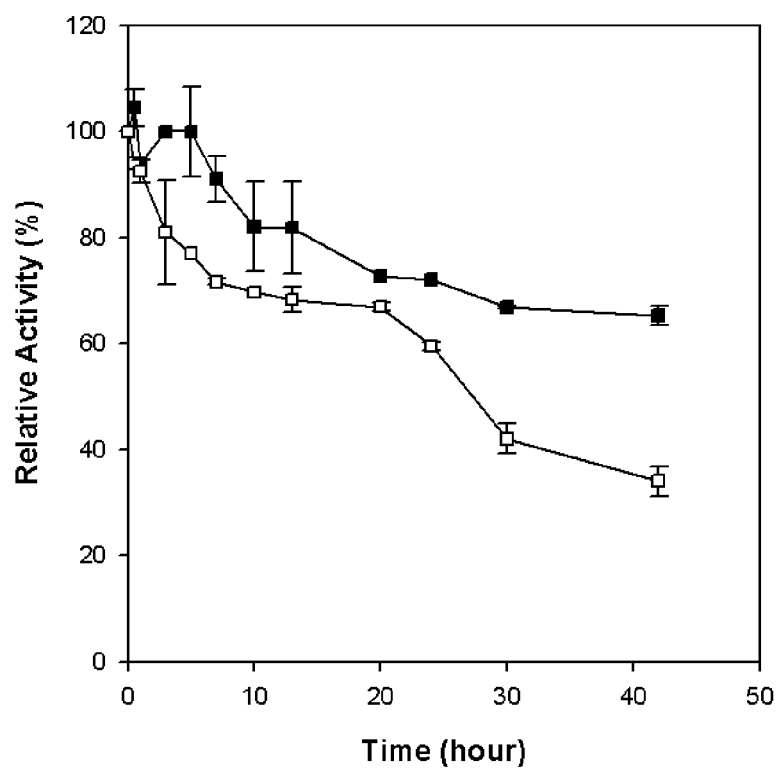
FIG. 13. Thermostability of the purified recombinant TgADH. Open squares, incubation at 80° C.; filled squares, incubation at 95° C. The relative activity of 100% equals to the initial ADH activity without heat treatment (1073 U/mg). Standard deviations of the measurements are indicated using error bars.

The recombinant TgADH had similar catalytic properties to the native enzyme purified from *T. guaymansensis* cells, including temperature dependence, optimum pH, thermostability and oxygen sensitivity. Both the native and recombinant TgADH was thermostable and its activity increased along with the temperature elevated up to 95° C. The activity values at temperatures higher than 95° C. were not measured because of the instability of the co-enzyme NADP at those high temperatures. The optimal pHs of the enzyme were tested for the oxidation and formation of 2-butanol using various 100 mM buffers to form a pH gradient from 5.5 to 11.5. The optimal pH value for the 2-butanol oxidation was 10.5 and for the 2-butanone reduction was 7.5. When the buffer pH values were higher than 10.5, the activity of butanol oxidation had a remarkable decrease, similarly, the activity of 2-butanol formation sharply decreased when the buffer pH value higher than 7.5. Recombinant TgADH presented outstanding stability at high temperatures, which had the same half-life ($t_{1/2}$) of about 26 hours at 95° C. and the residual activity remained more than 60% of the full activity after 42 hours incubation at 80° C. (FIGS. 12 and 13), revealing the resistance of enzymes to heat. However, both the native and recombinant form of TgADH presented sensitivity to oxygen. Some of the activity lost after exposure to the air, although they were more resistant to oxidation than that of iron-containing ADHs and the enzyme activity kept consistent in anaerobic conditions. The half-life ($t_{1/2}$) against the oxygen inactivation was about 4 hours, and loss of activity was slightly protected by the presence of 2 mM dithioreitol. Metal ions also affected the enzyme activity. The purified enzyme from *T. guaymasensis* was experimentally determined to be zinc-containing; however, the activity of butanol formation was blocked by zinc. When the zinc concentration increased from 20 to 100 μM in the assay mixtures, the corresponding activity obviously decreased.

Example 3

Sequence Alignment Studies

An alignment study was performed to compare sequences from 31 species with the sequence obtained for TgADH from *Thermococcus guayamasensis*. The results for sequence identity (%) and similarity (%) to TgAHD using Clustal W. are reported in Table 12.

TABLE 12

| | Alignment Data Comparing Sequences to TgADH | | | |
|---|---|---|---|---|
| ID number | Description | GenBank Number | Identity to TgADH (%) | Similarity to TgADH (%) |
| #1 | *Thermoanaerobacter tengcongensis* MB Threonine dehydrogenase and related Zn-dependent dehydrogenases | AAM23957 | 76 | 85 |
| #2 | *Thermoanaerobacter pseudethanolicus* ATCC 33223 Alcohol dehydrogenase, zinc-binding domain protein | ABY93890 | 76 | 85 |
| #3 | *Thermoanaerobacter brockii* alcohol dehydrogenase | CAA460531YKFA | 76 | 85 |
| #4 | *Thermoanaerobacter* sp. X514 Alcohol dehydrogenase, zinc-binding domain protein | ABY91961 | 76 | 84 |
| #5 | *Thermoanaerobacter ethanolicus* secondary-alcohol dehydrogenase | ABC50090 | 76 | 85 |
| #6 | *Clostridium botulinum* B1 str. Okra NADP-dependent alcohol dehydrogenase | ACA43794 | 69 | 81 |
| #7 | *Clostridium sporogenes* ATCC 15579 hypothetical protein CLOSPO_02108 | EDU35940 | 69 | 81 |
| #8 | *Thermosinus carboxydivorans* Nor1 Alcohol | EAX46383 | 70 | 81 |

TABLE 12-continued

Alignment Data Comparing Sequences to TgADH

| ID number | Description | GenBank Number | Identity to TgADH (%) | Similarity to TgADH (%) |
|---|---|---|---|---|
| | dehydrogenase, zinc-binding domain protein | | | |
| #9 | *Clostridium Beijerinckii* Alcohol Dehydrogenase | 1JQBA | 68 | 79 |
| #10 | *Clostridium botulinum* B str. Eklund 17B NADP-dependent alcohol dehydrogenase | ACD24409 | 66 | 78 |
| #11 | *Candidatus Kuenenia stuttgartiensis* alcohol dehydrogenase | CAJ74389 | 65 | 77 |
| #12 | *Methanosarcina acetivorans* C2A alcohol dehydrogenase (NADP | AAM05306 | 64 | 77 |
| #13 | *Methanosarcina barkeri* str. Fusaro alcohol dehydrogenase (NADP+) | AAZ71266 | 65 | 78 |
| #14 | *Arcobacter butzleri* RM4018 NADP-dependent alcohol dehydrogenase | ABV67302 | 64 | 76 |
| #15 | *Methanocorpusculum labreanum* Z Alcohol dehydrogenase, zinc-binding domain protein | ABN06935 | 61 | 74 |
| #16 | *Brachyspira pilosicoli* Adh | ABS12711 | 60 | 74 |
| #17 | *Brachyspira hyodysenteriae* Adh | ABS12704 | 60 | 74 |
| #18 | *Trichomonas vaginalis* G3 alcohol dehydrogenase 1, putative | EAY19615 | 59 | 74 |
| #19 | *Ruminococcus gnavus* ATCC 29149 hypothetical protein RUMGNA_01085 | EDN78675 | 59 | 73 |
| #20 | *Entamoeba histolytica* HM-1: IMSS NADP-dependent alcohol dehydrogenase | EAL48121 | 60 | 74 |
| #21 | *Malassezia globosa* CBS 7966 hypothetical protein MGL_3563 | EDP45012 | 58 | 72 |
| #22 | *Entamoeba dispar* SAW760 NADP-dependent alcohol dehydrogenase | EDR21674 | 60 | 73 |
| #23 | *Methanosphaera stadtmanae* DSM 3091|putative NADP-dependent alcohol dehydrogenase | ABC57355 | 59 | 71 |
| #24 | *Mycoplasma pneumoniae* M129 NADP-dependent alcohol dehydrogenase-like protein | AAB95926 | 56 | 71 |
| #25 | *Lactobacillus fermentum* IFO 3956 | BAG27708 | 58 | 70 |

TABLE 12-continued

Alignment Data Comparing Sequences to TgADH

| ID number | Description | GenBank Number | Identity to TgADH (%) | Similarity to TgADH (%) |
|---|---|---|---|---|
| #26 | alcohol dehydrogenase *Nitrosococcus oceani* ATCC 19707 Zinc-containing alcohol dehydrogenase superfamily | ABA56959 | 50 | 65 |
| #27 | *Geobacter uraniireducens* Rf4 Alcohol dehydrogenase, zinc-binding domain protein | ABQ28495 | 49 | 64 |
| #28 | *Gordonia* sp. TY-5 putative alcohol dehydrogenase | BAF43793 | 45 | 61 |
| #29 | *Frankia* sp. CcI3 Alcohol dehydrogenase, zinc-binding | ABD11608 | 45 | 60 |
| #30 | *Xylella fastidiosa* 9a5c NADP-alcohol dehydrogenase | AAF84536 | 42 | 59 |
| #31 | *Alkalilimnicola ehrlichei* MLHE-1 Alcohol dehydrogenase, zinc-binding domain protein | ABI57479 | 38 | 56 |

The results of alignment revealved a conserved catalytic zinc-binding motif, GHEX$_2$GX$_5$GX$_2$V (SEQ ID NO: 21) at residues 63-77: G$_{63}$H$_{64}$E$_{65}$AVG$_{68}$EVVEVG$_{74}$SHV$_{77}$ (SEQ ID NO: 23). Also revealed was a conserved binding motif of cofactor NADH: GXGX$_2$G (SEQ ID NO: 22) at residues 184-189: G$_{184}$IG$_{186}$PVG$_{189}$ (SEQ ID NO: 24). A fragment to TgADH was identified at residues 119 to 124: P$_{119}$L$_{120}$K$_{121}$E$_{122}$G$_{123}$G124 (SEQ ID NO: 25), which appears to be unique to TgADH.

Example 4

Preparation and Characterization of a C56S Mutant of TgADH

Methods and Results

The construct TgADH-pET 30a was obtained from codon plus *E. coli* BL21-RIL that contained TgADH-pET30a using QIAprep Miniprep Kit according to manufacturer's instructions. We then ran two PCR reactions using TgADH-pET30a as template and using two different sets of primers:

(1) TGECN, (SEQ ID NO: 33)
5'-TAGAATTCATGAGCAAGATGCGCGGTTTTGC-3'
and

TGMR, (SEQ ID NO: 34)
5'-CAGTATGCGCGGGAACTCGCTCATCTCCCTGGGAAACGCTGCCTC-3';
and (2) TGXHR, (SEQ ID NO: 35)
5'-ACCTCGAGTCACTCCTCTATGATGACC-3'
and

TGMF, (SEQ ID NO: 36)
5'-CGTTTCCCAGGGAGATGAGCGAGTTCCCGCGCATACTGGGTCACG-3' to obtain two different fragments with a overlap region, which were extracted separatedly. The two fragments were used for elongation using the same PCR condition to obtain the full length gene with the mutation C56S. Then 5' and 3' primers:

(SEQ ID NO: 37)
TGECN, 5'-TAGAATTCATGAGCAAGATGCGCGGTTTTGC-3'
and (SEQ ID NO: 38)
TGXHR, 5'-ACCTCGAGTCACTCCTCTATGATGACC-3' were added to amplify to the full length of the gene with mutation of C56S. After purification using the QIAquick PCR purification Kit, the PCR product was digested using EcoR1 and XhoI and then treated with alkaline phosphatase. The empty pET30a vector was also digested with EcoR1 and XhoI. Then, to make the The pET30a-TgADH-m1 expression construct for expressing TgADH-(C56S) mutant protein, the digested PCR product and the vector pET30a were ligated using T4 ligase overnight at 16 degree C. Heat shock method at 42° C. water bath for 45 sec was used to transform the construct into the competent cells *E. coli* DH5a. After the positive selection of the colonies, those contained the construct were picked for plasmid preparation and then for sequencing for checking the correct mutant made (see below).

TgADH wild type (SEQ ID NO: 39)
GTCTTTGAGGCAGCGTTTCCCAGGGAGATGTGTGAGTTCCCGCGCATACT and TgADH mutant (SEQ ID NO: 40)
GTCTTTGAGGCAGCGTTTCCCAGGGAGATGAGCGAGTTCCCGCGCATACT The pET30a-TgADH(C56S) plasmid was transformed into E. coli strain Rosetta-2 with vector, and TgADH(C56S) mutant protein was expressed via overnight induction with IPTG (0.2 mM and 0.4 mM). Induction was followed by running samples on a gel at 4.0 hour and overnight time points, and looking for an increase in 51 kD protein band as compared to a control incubation (no IPTG added).

The TgADH(C56S) mutant was assayed as described above for the wild-type TgADH. The result showed there was virtually no difference in the enzyme activity between the mutant TgADH(C56S) and wild type TgADH. When the both were exposed to air for a week, both lost activity. This result suggests that C56 is not responsible for the $O_2$-sensitivity of the wild type TgADH enzyme. Therefore, we plan to design new primers and make new mutants to investigate the effect of the other cysteine sites.

The pET30a-TgADH-m1 expression construct (for expressing TgADH(C56S) mutant protein) was transformed into host E. coli strain rosetta-2, and a sample of the transformed cells thereby obtained was deposited on Sep. 22, 2009 with the International Depositary Authority of Canada (International Depositary Authority of Canada, National Microbiology Laboratory, Public Health Agency of Canada, 1015 Arlington St., Winnipeg, Manitoba, Canada R3E 3R2) and assigned the accession number 220909-02.

Discussion

ADHs using NAD or NADP as coenzyme can be divided into three different groups, the zinc-dependent ADHs, the iron-containing ADHs, and the short-chain ADHs that are lack of metal. In hyperthermophilic archaea, a few zinc-containing ADHs have been recently purified and characterized. They are either ADHs from aerobic hyperthermophilic archaea S. solfataricus and A. pernix or TDHs from anaerobic hyperthermophiles P. furiosus and Pyrococcus horikoshii (Table 5). Similar to other zinc-containing ADHs or TDHs, ADH purified from the anaerobic hyperthermophile T. guaymasensis contained 364 amino acid residues and thereby was a member of medium-chain zinc-containing ADHs. The native T. guaymasensis ADH was in the quaternary structure of homotetramer, which is a usual structural characteristic of zinc-containing ADHs in archaea and bacteria. The hyperthermophilic ADHs including T. guaymasensis ADH showed that the optimum pH for the oxidation reaction was more alkaline than that for the reduction reaction. In contrast, those hyperthermophilic TDHs tended to optimally oxidize $_L$-threonine at pHs close to the neutral pH. T. guaymasensis ADH was specific for NADP$^+$ as coenzyme, whereas other known hyperthermophilic zinc-containing ADHs or TDHs preferred to NAD$^+$ coenzyme. The monomer of zinc-containing ADHs from hyperthermophiles contained catalytic and structural zinc atoms except that T. guaymasensis ADH contained 1 g atom zinc per subunit. Its amino acid sequence possessed no binding motif of structural zinc but catalytic zinc, thus indicating that its zinc atom was highly likely to play a catalytic role. Its sequence alignment also showed that the enzyme had high similarities to those NADP$^+$-dependent ADHs containing catalytic zinc atom only, e.g., ADHs from T. brockii and T. ethanolicus.

The enzyme from T. guaymasensis possesses several outstanding features to be a competitive biocatalyst. The enzyme was active within a broad temperature range from 30 to 95° C. as tested while the optimal temperature was over 95° C., which feature is common for ADHs originated from hyperthermophiles. The thermo-activity with 1149 U mg$^{-1}$ at 80° C. was remarkably higher than other zinc-containing ADHs characterized except the TDH from P. horikoshii. The activity of the butanediol dehydrogenase from S. cerevisiae was reported to be 968 U mg$^{-1}$ (Gonzalez et al. 2000) and obviously not as thermostable as T. guaymasensis ADH. The enzyme was hyperthermostable and its $t_{1/2}$ at 95° C. was about 24 hours, which is the most thermostable one among the family of known zinc-containing ADHs. The enzyme had broad substrate specificity. In the oxidation direction, the enzyme transformed various alcohols including primary and secondary, poly and di-ols while it reduced various aldehydes and ketones in the reduction direction. When the methanol was used to test the solvent tolerance, the methanol concentration at which half of full activity remained was about 24% (v/v) in the assay mixture. Therefore, high activity, outstanding thermostability and solvent tolerance make it a good candidate for chemical synthesis.

Aiming at the practical synthesis in industry, the coenzyme regeneration is necessary due to its high cost. To date, the coenzyme regeneration in the synthesis catalyzed by hyperthermophilic ADHs follows the enzyme-coupled or substrate-coupled strategy. The solvent tolerance of T. guaymasensis ADH is of great interest by offering an option to regenerate NADPH with the cheaper co-substrate isopropanol instead of enzymes such as formate dehydrogenase or glucose dehydrogenase. The isopropanol concentration usually was in excess amount, which was not only crucial to shift the equilibrium in the reduction direction, but also possible to enhance the solubility of hydrophobic substrates in the aqueous reaction medium. The NADPH regeneration system led to produce 45.6 mM butanol from 50 mM butanone by using only 1 mM NADPH with a transfer yield up to 92%, indicating it is a successful example on the NADPH regeneration system.

Coupled to the NADPH regeneration using isopropanol (and other alcohols, see above), the enzyme showed the asymmetric reduction of racemic acetoin, in which only (2R, 3R)-2,3-butanediol and meso-butanediol were produced. The enzyme also showed the asymmetric oxidation of 2,3-butanediol isomers, in which it had much lower specificity constant on (2S,3S)-(+)-2,3-butanediol than (2R,3R)-2,3-butanediol and meso-2,3-butanediol. Regarding the stereoselectivity of T. guaymasensis ADH, the highly similar example was the butanediol dehydrogenase from S. cerevisiae (González et al. 2000). Obeying anti-prelog's rule, T. guaymasensis ADH might undergo transferring a hydride ion from an R-configured alcohol to the pro-R face of NADP$^+$ or transferring a hydride ion from the pro-R face of NADPH to the si face of a carbonyl group of a ketone (Prelog 1964). The anti-Prelog ADHs were of greater interest since they are not as abundant as Prelog ADHs like those in horse liver, T. brockii, P. furiosus and S. solfataricus. Since T. guaymasensis ADH shared high similarity to the ADHs from T. brockii and T. ethanolicus, it was not expected that the enzyme had no stereoselectivity on the reduction of 2-butanone, which property has been well characterized in ADHs from T. brockii and T. ethanolicus (Keinan et al. 1986; Zheng et al. 1992). In addition, the enzyme did not catalyze the $_L$-threonine and $_L$-serine. It was recently noted that the ADH from P. furiosus showed higher enantioselectivity on phenyl-substituted ketoesters than the substrates lacking phenyl groups (Zhu et al. 2006). The stereoselectivity of T. guaymasensis ADH might be also affected by side groups of carbonyl group, in particular, the larger side group.

Most zinc-containing ADHs are resistant to oxygen; however, it was unexpected that TgADH was oxygen sensitive in both native and recombinant form. The reports of ADH oxygen inactivation were usually associated with iron-containing ADHs. However, the oxygen inactivation of zinc-containing ADHs has been scarcely reported. The well-known example is the zinc-containing ADH from mesophilic S. cerevisiae whose inactivation was due to the oxidation of SH group (Bühner and Sund 1969). Since zinc ion cannot be oxidized further, the inactivation of the enzyme may also be a consequence of the damage of amino acid residues such as cysteine. The enzyme of T. guaymasensis ADH had 4 cysteine residues per subunit (Cys39, Cys56, Cys213 and Cys306). Except Cys56, all the other three were conserved to T. brockii ADH. Cys39 was highly conserved in zinc-containing ADHs and a putative active site residue, which has been proved to coordinate the binding of catalytic zinc in T. brockii ADH. The residue $Cys_{56}$ was unique in TgADH and did not exist in the same location of any other zinc containing ADHs sharing high similarities, so site direct mutagenasis at $Cys_{56}$ residue would shed light to the role of $Cys_{56}$ in the oxygen sensitivity. However, the TgADH(C56S) mutant showed similar properties to the native TgADH including the sensitivity to oxygen, indicating $C_{56}$ is not responsible for the oxygen sensitivity of the enzyme.

The N-terminal amino acid sequence determined by Edman degradation indicated that serine was the initial amino acid of mature T. guaymasensis ADH. N-terminal methionine was excised in the mature enzyme of T. guaymasensis ADH, which is governed by the side-chain length of the penultimate amino acid (Hirel et al. 1989). As observed in bacteria and yeasts, N-terminal methionine excision of an enzyme could be critical for its function and stability (Eichler and Adams 2005) but its role for archaeal enzymes is not clear yet. Amino acid composition and its substitution patterns between mesophilic and hyperthermophilic proteins shed light on the understanding of common features of thermostability (Robb and Clark 1999; Sælensminde et al. 2007; Sterner and Liebl 2001). T. guaymasensis ADH showed 77% identity to T. brockii ADH and 65% identity to C. beijerinckii ADH (FIGS. 14 and 15), suggesting that gains in stabilization might be achieved in regions that are less conserved (Kumar et al. 2000). Molecular mechanisms of enzyme thermostability and thermophilicity are varied, differing from enzyme to enzyme, which could be a combination of intrinsic stabilizing forces (such as salt bridges, hydrogen bonds, hydrophobic interactions) and extrinsic stabilizing factors. The uncharged polar residues Gln, Asn, Ser decreased in T. guaymasensis ADH, in which the first two are prone to deamination and known to be the most temperature sensitive (Cambillau and Claverie 2000; Wright 1991). In contrast, hyperthermophilic and thermophilic proteins showed an increase of charged amino acid residues, especially Arg, Glu. The equal increase of oppositely charged residues (Arg and Glu) in hyperthermophiles most likely led to the increased amount of ion pairs observed already on their proteins (Cambillau and Claverie 2000). As the best helix-forming residue, alanine increased, similarly to previous observations (Vieille et al. 2001). On the other hand, proline composition increased significantly, which might be the structural base of rigidity of hyperthermophilic enzymes. The difference between hyperthmophilic and mesophilic proteins/enzymes would provide some clues to increase thermal stability of mesophilic enzymes. Sequence alignments, amino acid comparisons, and predicted 3-D structure comparisons indicate that TgADH is, indeed, very similar to mesophilic counterparties. A fragment of $P_{119}L_{120}K_{121}E_{122}G_{123}G_{124}$ was found to be unique in the TgADH and it was identified to be a putative fragment that may related to the thermostability. Interestingly, the length of the hyperthermophilic/thermophilic enzyme was not less than the mesophilic homologous. From the view of primary structure, the ratio of amino acid residues Ala, Arg, Glu, Lys and Pro was increased in TgADH, whereas that of Ala, Asn Gln, Ser and Val decreased. In contrast, the uncharged polar residues Gln, Asn, Ser decreased in T. guaymasensis ADH, in which the first two are prone to deamination and known to be the most temperature sensitive. However, it is likely that other determinants are also critical for thermostability, and detailed structural comparisons between the two types of enzyme are needed.

The optimal pHs of both native and recombinant TgADH on the oxidation of alcohols are more alkaline than those on the reduction of aldehydes or ketones. Generally, dependence of enzyme activity on pH value is related to protonation at the active site. In a hyperthermophilic L-threonine dehydrogenase from Pyrococcus horikoshii, the proton dissociation model with two catalytic forms among three ionizable groups was derived to explain the experimental the examined pH dependence. It was also reported in Drosophila lebanonensis short-chain alcohol dehydrogenase, the protonation/deprotonation transition was related to the coupled ionization of $Tyr_{151}$ and $Lys_{155}$ in the active site and the pH dependence of the proton abstraction was correlated with a reorganization of the hydrogen bond network in the active site. Likewise, the oxidoreductase activity of TgADH probably relies on a proton relay mechanism. The conformation of the residues at the catalytic site accomplishes with the deprotonation process, which would be an explanation for dissociation of substrates or cofactor from the enzyme when pH changes.

The physiological role of T. guaymasensis ADH seems not clearly to ascertain although the conserved domain search indicated homology to threonine dehydrogenase. T. guaymasensis ADH did not catalyze the oxidation of threonine as tested at different pHs (pH 7.5, 8.8 and 10.5). However, the possible physiological role for T. guaymasensis ADH might arise from its ability of interconversion between alcohols and corresponding ketone or aldehydes. T. guaymasensis ADH reversibly catalyzed the oxidation of 2,3-butanediol to acetoin, which cannot be oxidized to diacetyl. Regarding this feature, properties of T. guaymasensis ADH including its stereoselectivity were similar to those observed on the (2R, 3R)-(−)-butanediol dehydrogenase (BDH) from S. cerevisiae (González et al. 2000). S. cerevisiae can grow on 2,3-butanediol as the sole carbon and energy source, in which BDH content had over 3 fold increases. The role of BDH in S. cerevisiae was suggested to be required for oxidation and formation of 2,3-butanediol. However, no production of 2,3-butanediol was observed in the spent culture media of T. guaymasensis, implying that T. guaymasensis ADH might be more likely to be involved in the formation of acetoin from diacetyl. In addition, T. guaymasensis produced ethanol at mM-level and the enzyme had higher catalytic efficiency on NADPH over NADP as coenzymes, which leads to a proposal that the enzyme could be concurrently responsible for ethanol and acetoin formation during fermentation.

Both the native and recombinant TgADH were in the ternary structure of homotetramer, which is the usual structural characteristic of the previously characterized zinc-containing ADHs in archaea. Interestingly, the amino acid sequence of TgADH has high overall identities to NADP dependent zinc-containing ADHs from thermophilic bacteria, e.g., ADHs from *T. brockii* and *T. tengcongensis*. The sequence alignment indicated TgADH shared conserved co-enzyme NADP binding sites (G184XG186XXG189) and active site (G63H64E65X2G68X5G74X2V77) predicted harboring catalytic zinc ion, which matched the biochemical characterizations. From the 3-D structure modeling, the monomer of TgADH folded into two domains, the catalytic domain closing to N-terminal end and one NADP-binding domain closing to C-terminal end. The phylogenetic analysis between TgADH and the thermophilic and hyperthermophilic zinc-containing ADH indicated TgADH to be closer to the ADHs containing catalytic zinc atom only in evolution but further from the ADHs containing both catalytic and structure zinc ions.

Cloning and sequencing of the entire encoding gene of TgADH provided fundamental information for over-expression of the hyperthermophilic enzymes in heterologous hosts. The production of recombinant extremophilic proteins in mesophilic hosts such as *E. coli* is highly desirable due to simpler culture conditions and typically higher yields. Compared to a series of chromatography for the native enzyme purification, only two steps including heat treatment and liquid chromatography were needed for purification. Because of its stability at high temperatures, one heat treatment step could significantly simplify the purification of the recombinant TgADH from *E. coli*. The over-expression of archaeal genes in bacterium is often challenged by poor yield or loss of activity due to different codon bias. However, the recombinant TgADH seems soluble, active and thermostable. Although native TgADH purified from *T. guaymensensis* directly presented a high concentration in the cells (Ying et al., unpublished), *E. coli* provided a much higher yield of recombinant TgADH at about 4~5 mg per gram cells. The recombinant TgADH carried almost same activity and other catalytic properties with the native enzyme purified from *T. guaymensensis* directly. When cloned and expressed in mesophilic hosts, the enzymes usually retain its thermal properties, suggesting that these properties would be genetically encoded.

Produced in relatively high amounts by heterologous expression in *E. coli* and easily purified together with the outstanding stabilities, TgADH carries an obvious industrial perspective. It is highly R-enantioselective, which makes this enzyme a potential catalyst for industry, especially for the production of chiral compounds. Oxygen sensitivity should be kept in mind when working with this enzyme although most organic synthesis reactions occur in the absence of oxygen.

The above-described embodiments of the invention are intended to be examples only. Alterations, modifications and variations can be effected to the particular embodiments by those of skill in the art without departing from the scope of the invention, which is defined solely by the claims appended hereto.

REFERENCES

1. Altschul, S. F., T. L. Madden, A. A. Schäffer, J. Zhang, Z. Zhang, W. Miller, and D. J. Lipman. 1997. Gapped BLAST and PSI-BLAST: a new generation of protein database search programs. Nucl. Acids Res. 25:3389-3402.
2. Ammendola, S., C. A. Raia, C. Caruso, L. Camardella, S. D'Auria, M. De Rosa, and M. Rossi. 1992. Thermostable NAD+-dependent alcohol dehydrogenase from *Sulfolobus solfataricus*: gene and protein sequence determination and relationship to other alcohol dehydrogenases. Biochemistry 31:12514-12523.
3. Antoine, E., J. L. Rolland, J. P. Raffin, and J. Dietrich. 1999. Cloning and over-expression in *Escherichia coli* of the gene encoding NADPH group III alcohol dehydrogenase from *Thermococcus hydrothermalis*. Eur. J. Biochem. 264: 880-889.
4. Balch, W. E., G. E. Fox, L. J. Magrum, C. R. Woese, and W. S. Wolfe. 1979. Methanogens: re-evaluation of a unique biological group. Microbiol. Rev. 43:260-296.
5. Bertoldo, C., and G. Antranikian. 2006. The order *Thermococcales*. Prokaryotes 3:69-81.
6. Bogin, O., I. Levin, Y. Hacham, S. Tel-Or, M. Peretz, F. Frolow, and Y. Burstein. 2002. Structural basis for the enhanced thermal stability of alcohol dehydrogenase mutants from the mesophilic bacterium Clostridium beijerinckii: contribution of salt bridging. Protein Sci. 11:2561-2574.
7. Bogin, O., M. Peretz, Y. Hacham, Y. Korkhin, F. Frolow, A. J. Kalb, and Y. Burstein. 1998. Enhanced thermal stability of *Clostridium beijerinckii* alcohol dehydrogenase after strategic substitution of amino acid residue with prolines from the homologous thermophilic *Thermoanaerobacter brockii* alcohol dehydrogenase. Protein Sci. 7:1156-1163.
8. Bogin, O., M. Peretz, and Y. Burstein. 1997. *Thermoanaerobacter brockii* alcohol dehydrogenase: characterization of the active site metal and its ligand amino acids. Protein Sci. 6:450-458.
9. Bradford, M. M. 1976. A rapid and sensitive method for the quantitation of microgram quantities of protein utilizing the principle of protein-dye binding. Anal. Biochem. 72:248-254.
10. Bühner, M., and H. Sund. 1969 Yeast alcohol dehydrogenase: —SH groups, disulfide groups, quaternary structure, and reactivation by reductive cleavage of disulfide groups. Eur. J. Biochem. 11:73-79.
11. Cambillau, C., and J. M. Claverie. 2000. Structural and genomic correlates of hyperthermostability. J. Biol. Chem. 275:32383-32386.
12. Canganella, F., W. J. Jones, A. Gambacorta, and G. Antranikian. 1998. *Thermococcus guaymasensis* sp. nov. and *Thermococcus aggregans* sp. nov., two novel thermophilic archaea isolated from the Guaymas Basin hydrothermal vent site. Int. J. Syst. Bacteriol. 48:1181-1185.
13. Chong, P. K., A. M. Burja, H. Radianingtyas, A. Fazeli, and P. C. Wright. 2007. Translational and transcriptional analysis of *Sulfolobus solfataricus* P2 to provide insights into alcohol and ketone utilization. Proteomics 7:424-435.
14. Delano, W. L. 2002. The PyMOL molecular graphics system. Delano Scientific, Palo Alto, Calif.
15. Eichler, J., and M. W. W. Adams. 2005. Posttranslational protein modification in *Archaea*. Microbiol. Mol. Biol. Rev. 69:393-425.
16. Esposito, L., I. Bruno, F. Sica, C. A. Raia, A. Giordano, M. Rossi, L. Mazzarella, and A. Zagari. 2003. Sructural study of a single-point mutant of *Sulfolobus solfataricus* alcohol dehydrogenase with enhanced activity. FEBS Lett. 539:14-18.
17. Esposito, L., F. Sica, C. A. Raia, A. Giordano, M. Rossi, L. Mazzarella, and A. Zagari. 2002. Crystal structure of the alcohol dehydrogenase from the hyperthermophilic archaeon *Sulfolobus solfataricus* at 1.85 Å resolution. J. Mol. Biol. 318:463-477.
18. Gasteiger, E., C. Hoogland, A. Gattiker, S. Duvaud, M. R. Wilkins, R. D. Appel, and A. Bairoch. 2005. Protein identification and analysis tools on the ExPASy Server, p. 571-607. In Walker J M (ed.), The proteomics protocols handbook. Humana Press, Totowa, N.J.

19. Giordano, A., R. Cannio, F. La Cara, S. Bartolucci, M. Rossi, and C. A. Raia. 1999. Asn249Tyr substitution at the coenzyme binding domain activates *Sulfolobus solfataricus* alcohol dehydrogenase and increases its thermal stability. Biochemistry 38:3043-3054.

20. Giordano, A., F. Febbraio, C. Russo, M. Rossi, and C. A. Raia. 2005. Evidence for co-operativity in coenzyme binding to tetrameric *Sulfolobus solfataricus* alcohol dehydrogenase and its structural basis: fluorescence, kinetic and structural studies of the wild-type enzyme and non-co-operative N249Y mutant. Biochem. J. 388:657-667.

21. Goihberg, E., O. Dym, S. Tel-Or, I. Levin, M. Peretz, and Y. Burstein. 2007. A single proline substitution is critical for the thermostabilization of *Clostridium beijerinckii* alcohol dehydrogenase. Proteins: Structure, Function and Bioinformatics 66:196-204.

22. González, E., M. R. Fernández, C. Larroy, L. Solà, M. A. Pericàs, X. Parés, and J. A. Biosca. 2000. Characterization of a (2R,3R)-2,3-butanediol dehydrogenase as the *Saccharomyces cerevisiae* YAL060W gene product. J. Biol. Chem. 275: 35876-35885.

23. Guex, N., and M. C. Peitsch. 1997. SWISS-MODEL and the Swiss-PdbViewer: An environment for comparative protein modelling. Electrophoresis 18:2714-2723.

24. Guy, J. E., M. N. Isupov, and J. A. Littlechild. 2003. The structure of an alcohol dehydrogenase from the hyperthermophilic archaeon *Aeropyrum pernix*. J. Mol. Biol. 331: 1041-1051.

25. Heiss, C., M. Laivenieks, J. G. Zeikus, and R. S. Phillips. 2001. The stereospecificity of secondary alcohol dehydrogenase from *Thermoanaerobacter ethanolicus* is partially determined by active site water. J. Am. Chem. Soc. 123: 345-346.

26. Higashi, N., H. Fukada, and K. Ishikawa. 2005 Kinetic study of thermostable $_L$-threonine dehydrogenase from an archaeon *Pyrococcus horikoshii*. J. Biosci. Bioeng. 99:175-180.

27. Hirakawa, H., N. Kamiya, Y. Kawarabayashi, and T. Nagamune. 2004. Properties of an alcohol dehydrogenase from the hyperthermophilic archaeon *Aeropyrum pernix* K1. J. Biosci. Bioeng. 97:202-206.

28. Hirel, P. H., J. M. Schmitter, P. Dessen, G. Fayat, and S. Blanquet. 1989. Extent of N-terminal methionine excision from Escherichia coli proteins is governed by the side-chain length of the penultimate amino acid. Proc. Natl. Acad. Sci. 86:8247-8251.

29. Ishikawa, K., N. Higashi, T. Nakamura, T. Matsuura, A. Nakagawa. 2007. The first crystal structure of $_L$-threonine dehydrogenase. J. Mol. Biol. 366:857-867.

30. Johnson, A. R., and E. E. Dekker. 1998. Site-directed mutagenesis of histidine-90 in *Escherichia coli* $_L$-threonine dehydrogenase alters its substrate specificity. Arch. Biochem. Biophy. 351:8-16.

31. Karakashev, D., A. B. Thomsen, and I. Angelidaki. 2007. Anaerobic biotechnological approaches for production of liquid energy carriers from biomass. Biotech. Lett. 29:1005-1012.

32. Keinan, E., K. K. Seth, and R. Lamed. 1986. Organic synthesis with enzymes. 3. TBADH-catalyzed reduction of chloro ketones. Total synthesis of (+)-(S,S)-(cis-6-methyltetrahydropyran-2-yl)-acetic acid: a civet constituent. J. Am. Chem. Soc. 108:3473-3480.

33. Kopp, J., and T. Schwede. 2004. The SWISS-MODEL repository of annotated three-dimensional protein structure homology models. Nucl. Acids Res. 32:D230-D234.

34. Korkhin, Y., A. J. Kalb (Gilboa), M. Peretz, O. Bogin, Y. Burstein, and F. Frolow. 1998. NADP-dependent bacterial alcohol dehydrogenases: crystal structure, cofactor-binding and cofactor specificity of the ADHs of *Clostridium beijerinckii* and *Thermoanaerobacter brockii*. J. Mol. Biol. 278:967-981.

35. Kumar, S., C. J. Tsai, and P. Nussinov. 2000. Factors enhancing protein thermostability. Protein Eng. 13:179-191.

36. Laemmli, U. K. 1970. Cleavage of structural proteins during assembly of the head of bacteriophage T4. Nature 227:680-685.

37. Larroy, C., M. R. Fernández, E. González, X. Parés, and J. A. Biosca J A. 2002. Characterization of the *Saccharomyces cerevisiae* YMR318C (ADH6) gene product as a broad specificity NADPH-dependent alcohol dehydrogenase: relevance in aldehyde reduction. Biochem. J. 361:163-172.

38. Li, D., and K. J. Stevenson. 1997. Purification and sequence analysis of a novel NADP(H)-dependent type III alcohol dehydrogenase from *Thermococcus* strain AN1. J. Bacteriol. 179:4433-4437.

39. Ma, K., A. Hutchins, S. J. S. Sung, and M. W. W. Adams. 1997. Pyruvate ferrodoxin oxidoreductase from the hyperthermophilic archaeon, *Pyrococcus furiosus*, functions as a CoA-dependent pyruvate decarboxylase. Proc. Natl. Acad. Sci. 94:9608-9613.

40. Ma, K., H. Loessner, J. Heider, M. K. Johnson, and M. W. W. Adams. 1995. Effects of elemental sulfur on the metabolism of the deep-sea hyperthermophilic archaeon *Thermococcus* strain ES-1: characterization of a sulfur-regulated, non-heme iron alcohol dehydrogenase. J. Bacteriol. 177:4748-4756.

41. Ma, K., F. T. Robb, and M. W. W. Adams. 1994. Purification and characterization of NADP$^+$-specific alcohol dehydrogenase and glutamate dehydrogenase from hyperthermophilic archaeon *Thermococcus litoralis*. Appl. Environ. Microbiol. 60:562-568.

42. Machielsen, R., A. R. Uria, S. W. M. Kengen, and J. van der Oost. 2006. Production and characterization of a thermostable alcohol dehydrogenase that belongs to the aldo-keto reductase superfamily. Appl. Environ. Microbiol. 72:233-238.

43. Machielsen, R., and J. van der Oost. 2006. Production and characterization of a thermostable $_L$-threonine dehydrogenase from the hyperthermophilic archaeon *Pyrococcus furiosus*. FEBS 273:2722-2729.

44. Musa, M. M., K. I. Ziegelmann-Fjeld, C. Vieille, J. G. Zeikus, and R. S. Phillips. 2007. Asymmetric reduction and oxidation of aromatic ketones and alcohols using W110A secondary alcohol dehydrogenase from *Thermoanaerobacter ethanolicus*. J. Org. Chem. 72:30-34.

45. Olofsson, L., N. A. Nicholls, and S. Wikman. 2005. TBADH activity in water-miscible organic solvents: correlations between enzyme performance, enantioselectivity and protein structure through spectroscopic studies. Org. Biomol. Chem. 3:750-755.

46. Peitsch, M. C. 1995. Protein modeling by E-mail. Bio/Technology 13:658-660.

47. Phillips, R. S. 2002. Tailoring the substrate specificity of secondary alcohol dehydrogenase. Can. J. Chem. 80:680-685.

48. Pikuta, E. V., D. Marsic, T. Itoh, A. K. Bej, J. Tang, W. B. Whitman, J. D. Ng, O. K. Garriott, and R. B. Hoover. 2007. *Thermococcus thioreducens* sp. nov., a novel hyperthermophilic, obligately sulfur-reducing archaeon from a deep-sea hydrothermal vent. Int. J. Syst. Evol. Microbiol. 57:1612-1618.

49. Prelog, V. 1964. Specification of the stereospecificity of some oxido-reductases by diamond lattice sections. Pure Appl. Chem. 9:119-130.
50. Raia, C. A., A. Giordano, and M. Rossi. 2001. Alcohol dehydrogenase from *Sulfolobus solfataricus*. Methods Enzymol. 331:176-195.
51. Reid, M. F., and C. A. Fewson. 1994. Molecular characterization of microbial alcohol dehydrogenases. Crit. Rev. Microbiol. 20:13-56
52. Reiter, W. D., P. Palm, and W. Zillig. 1988. Transcription termination in the archaebacterium *Sulfolobus*: signal structures and linkage to transcription initiation. Nucl. Acids Res. 16:2445-2459.
53. Rella, R., C. A. Raia, M. Pensa, F. M. Pisani, A. Gambacorta, M. De Rosa, and M. Rossi. 1987. A novel archaebacterial $NAD^+$-dependent alcohol dehydrogenase: purification and properties. Eur. J. Biochem. 167:475-479.
54. Sænsminde, G., Ø. Halskau, R. Helland, N. P. Willassen, and I. Jonassen. 2007. Structure-dependent relationships between growth temperature of prokaryotes and the amino acid frequency in their proteins. Extremophiles 11:585-596.
55. Sambrook, J., E. F. Fritsch, and T. Maniatis. 1989. Molecular Cloning: A Laboratory Manual (second edition). Cold Spring Harbor Laboratory Press, Cold Spring Harbor, New York, N.Y.
56. Schwede, T., J. Kopp, N. Guex, and M. C. Peitsch. 2003. SWISS-MODEL: an automated protein homology-modeling server. Nucl. Acids Res. 31:3381-3385.
57. Selig, M., K. B. Xavier, H. Santos, and P. Schönheit. 1997. Comparative analysis of Embden-Meyerhof and Entner-Doudoroff glycolytic pathways in hyperthermophilic archaea and the bacterium *Thermotoga*. Arch. Microbiol. 167:217-232.
58. Sterner, R., and W. Liebl. 2001. Thermophilic adaptation of proteins. Crit. Rev. Biochem. Mol. Biol. 36:39-106.
59. Thompson, J. D., D. G. Higgins, and T. J. Gibson. 1994. CLUSTAL W: improving the sensitivity of progressive multiple sequence alignment through sequence weighting, position-specific gap penalties and weight matrix choice. Nucl. Acids Res. 22:4673-4680.
60. Triglia, T., M. Peterson, and D. Kemp. 1988. A procedure for in vitro amplification of DNA segments that lie outside the boundaries of known sequences. Nucl. Acids Res. 16:8186.
61. Tripp, A. E., D. S. Burdette, J. G. Zeikus, and R. S. Phillips. 1997. Mutation of serine-39 to threonine in thermostable secondary alcohol dehydrogenase from *Thermoanaerobacter ethanolicus* changes enantiosepecificity. J. Am. Chem. Soc. 120:5137-5141.
62. Vieille, C., and G. J. Zeikus. 2001. Hyperthermophilic enzymes: sources, uses, and molecular mechanisms for thermostability. Microbiol. Mol. Biol. Rev. 65:1-43.
63. Wright, H. T. 1991. Nonenzymatic deamidation of asparaginyl and glutaminyl residues in proteins. Crit. Rev. Biochem. Mol. Biol. 26:1-52.
64. Zheng, C. S., V. T. Pham, R. S. Phillips. 1992. Asymmetric reduction of ketoesters with alcohol dehydrogenase from *Thermoanaerobacter ethanolicus*. Bio. Med. Chem. Letts. 2:619-622.
65. Zhu, D., H. T. Malik, and L. Hua. 2006. Asymmetric ketone reduction by a hyperthermophilic alcohol dehydrogenase: the substrate specificity, enantioselectivity and tolerance of organic solvents. Tetrahedron Asymmetry 17:3010-3014.
66. Ziegelmann-Fjeld, K. I., M. M. Musa, R. S. Phillips, J. G. Zeikus, and C. Vieille. 2007. A *Thermoanaerobacter ethanolicus* secondary alcohol dehydrogenase mutant derivative highly active and stereoselective on phenylacetone and benzylacetone. Protein Engineering, Design and Selection 20:47-55.
67. Ziegenhorn, J., M. Senn, and T. Bücher. 1976. Molar absorptivities of β-NADH and β-NADPH. Clin. Chem. 22:151-160.

---

The invention claimed is:

1. An isolated polypeptide selected from the group consisting of:
   (a) a polypeptide comprising an amino acid sequence as set forth in SEQ ID NO: 2, 4, 6, 8 or 10 and having alcohol dehydrogenase activity; and
   (b) a polypeptide comprising an amino acid sequence at least 90% identical to SEQ ID NO: 2, 4, 6, 8 or 10, wherein said polypeptide comprises the amino acid sequences set forth in SEQ ID NO: 23, SEQ ID NO: 24 and SEQ ID NO: 25, and has alcohol dehydrogenase activity.

2. The isolated polypeptide of claim 1, wherein the polypeptide is a polypeptide comprising an amino acid sequence selected from the group consisting of SEQ ID NOs: 2, 4, 6, 8 and 10 and having alcohol dehydrogenase activity.

3. An isolated polypeptide comprising an amino acid sequence at least 95% identical to SEQ ID NO: 2, 4, 6, 8 or 10, and having alcohol dehydrogenase activity.

4. The isolated polypeptide of claim 1, which is recombinantly produced.

5. An isolated polypeptide comprising an amino acid sequence at least 95% identical to SEQ ID NO: 2, 4, 6, 8 or 10, wherein said polypeptide comprises the amino acid sequences set forth in SEQ ID NO: 23, SEQ ID NO: 24 and SEQ ID NO: 25, and has alcohol dehydrogenase activity.

6. The isolated polypeptide of claim 1, 2, 3, or 5 having a preference for primary or secondary alcohols and/or corresponding ketones or aldehydes.

7. The isolated polypeptide of claim 1, 2, 3, or 5 exhibiting a preference for R-stereochemistry.

8. The isolated polypeptide of claim 1, 2, 3 or 5, which exhibits alcohol dehydrogenase activity at temperatures selected from the group consisting of higher than 50° C., higher than 60° C., higher than 70° C., higher than 80° C., higher than 90° C., and higher than 100° C.

* * * * *

SEQUENCE LISTING

```
<160> NUMBER OF SEQ ID NOS: 40

<210> SEQ ID NO 1
<211> LENGTH: 1098
<212> TYPE: DNA
<213> ORGANISM: Thermococcus guaymasensis

<400> SEQUENCE: 1
atgagcaaga tgcgcggttt tgcaatggtg gacttcggca aggccgagtg gattgagaag      60
gagaggccga agcccgggcc gtacgatgca atcgtcaagc ccattgcagt cgccccatgc     120
acctcggaca tccacacggt ctttgaggca gcgtttccca gggagatgtg tgagttcccg     180
cgcatactgg gtcacgaagc agtcggagag gtagtcgagg tcggaagcca cgtcaaggac     240
ttcaagcccg gggacagggt tgttgtcccg gcaataactc ccgactggag gacccttgac     300
gttcagaggg gctaccacca gcactccggt ggaatgctcg ccggatggaa gttcagcaac     360
cccctcaagg agggcggtaa ggacggtgtg tttgcagaat acttccacgt caacgacgct     420
gacatgaacc tggcacacct tccggacgaa atcaagccgg aagtcgctgt catggccacc     480
gacatgatga ccacgggatt ccacggcgcc gagctcgccg acattccgct cggaggaaca     540
gtcgccgtca ttggaattgg accggtcggc ctgatgcgcg ttgccggggc aagactgctc     600 ggtgccgaa ggatcatcgc ggtcggcagc aggccggtgt gcgttgaggc cgctaagtac     660
```

```
tacggagcca ccgacatagt caaccgcagg gagcacccgg acatcgccgg aaggatcctg      720
gagctgaccg gtggagaggg tgttgattcg gtgataatcg ccggcggaaa cgttgacgta      780
atgaagaccg cggtgaagat agtcaagccc ggaggaacgg tggccaacat caactacttc      840
ggcagcggtg actacctccc gatcccgagg attgagtggg gccagggaat ggcccacaag      900
accatcaagg gagggctctg cccaggcgga cgcctgagga tggagcgcct gcttgacctc      960
atcaagtacg cagggttga cccgtcaagg ctcataaccc acaagttcaa gggattcgat     1020
aagataccag aagccctcta cctgatgaag gacaagccca agacctgat aaagcccgtg      1080 gtcatcatag aggagtga                                                  1098

<210> SEQ ID NO 2
<211> LENGTH: 365
<212> TYPE: PRT
<213> ORGANISM: Thermococcus guaymasensis

<400> SEQUENCE: 2
```

Met Ser Lys Met Arg Gly Phe Ala Met Val Asp Phe Gly Lys Ala Glu
1               5                   10                  15

Trp Ile Glu Lys Glu Arg Pro Lys Gly Pro Tyr Asp Ala Ile Val
            20                  25                  30

Lys Pro Ile Ala Val Ala Pro Cys Thr Ser Asp Ile His Thr Val Phe
        35                  40                  45

Glu Ala Ala Phe Pro Arg Glu Met Cys Glu Phe Pro Arg Ile Leu Gly
    50                  55                  60

His Glu Ala Val Gly Glu Val Val Glu Val Gly Ser His Val Lys Asp
65                  70                  75                  80

Phe Lys Pro Gly Asp Arg Val Val Val Pro Ala Ile Thr Pro Asp Trp
                85                  90                  95

Arg Thr Leu Asp Val Gln Arg Gly Tyr His Gln His Ser Gly Gly Met
            100                 105                 110

Leu Ala Gly Trp Lys Phe Ser Asn Pro Leu Lys Glu Gly Gly Lys Asp
        115                 120                 125

Gly Val Phe Ala Glu Tyr Phe His Val Asn Asp Ala Asp Met Asn Leu
    130                 135                 140

Ala His Leu Pro Asp Glu Ile Lys Pro Glu Val Ala Val Met Ala Thr
145                 150                 155                 160

Asp Met Met Thr Thr Gly Phe His Gly Ala Glu Leu Ala Asp Ile Pro
                165                 170                 175

Leu Gly Gly Thr Val Ala Val Ile Gly Ile Gly Pro Val Gly Leu Met
            180                 185                 190

Ala Val Ala Gly Ala Arg Leu Leu Gly Ala Gly Arg Ile Ile Ala Val
        195                 200                 205

Gly Ser Arg Pro Val Cys Val Glu Ala Ala Lys Tyr Tyr Gly Ala Thr
    210                 215                 220

Asp Ile Val Asn Arg Arg Glu His Pro Asp Ile Ala Gly Arg Ile Leu
225                 230                 235                 240

Glu Leu Thr Gly Gly Glu Gly Val Asp Ser Val Ile Ala Gly Gly
                245                 250                 255

Asn Val Asp Val Met Lys Thr Ala Val Lys Ile Val Lys Pro Gly Gly
            260                 265                 270

Thr Val Ala Asn Ile Asn Tyr Phe Gly Ser Gly Asp Tyr Leu Pro Ile
        275                 280                 285

Pro Arg Ile Glu Trp Gly Gln Gly Met Ala His Lys Thr Ile Lys Gly

```
                  290                 295                 300
Gly Leu Cys Pro Gly Gly Arg Leu Arg Met Glu Arg Leu Leu Asp Leu
305                 310                 315                 320

Ile Lys Tyr Gly Arg Val Asp Pro Ser Arg Leu Ile Thr His Lys Phe
                325                 330                 335

Lys Gly Phe Asp Lys Ile Pro Glu Ala Leu Tyr Leu Met Lys Asp Lys
                340                 345                 350

Pro Lys Asp Leu Ile Lys Pro Val Val Ile Ile Glu Glu
                355                 360                 365

<210> SEQ ID NO 3
<211> LENGTH: 1095
<212> TYPE: DNA
<213> ORGANISM: Thermococcus guaymasensis

<400> SEQUENCE: 3
agcaagatgc gcggttttgc aatggtggac ttcggcaagg ccgagtggat tgagaaggag      60
aggccgaagc ccgggccgta cgatgcaatc gtcaagccca ttgcagtcgc ccatgcacc     120 tcggacatcc acacggtctt tgaggcagcg tttcccaggg agatgtgtga gttcccgcgc    180
atactgggtc acgaagcagt cggagaggta gtcgaggtcg aagccacgt caaggacttc     240 aagcccgggg acaggttgt tgtcccggca ataactcccg actggaggac ccttgacgtt     300 cagagggct accaccagca ctccggtgga atgctcgccg atggaagtt cagcaacccc     360 ctcaaggagg cggtaagga cggtgtgttt gcagaatact tccacgtcaa cgacgctgac    420
atgaacctgg cacaccttcc ggacgaaatc aagccggaag tcgctgtcat ggccaccgac    480
atgatgacca cgggattcca cggcgccgag ctcgccgaca ttccgctcgg aggaacagtc    540
gccgtcattg aattggacc ggtcggcctg atggcggttg ccggggcaag actgctcggt     600
gccggaagga tcatcgcggt cggcagcagg ccggtgtgcg ttgaggccgc taagtactac    660
ggagccaccg acatagtcaa ccgcaggag cacccggaca tcgccggaag gatcctggag     720
ctgaccggtg agagggtgt tgattcggtg ataatcgccg gcggaaacgt tgacgtaatg    780
aagaccgcgg tgaagatagt caagcccgga ggaacggtgg ccaacatcaa ctacttcggc    840
agcggtgact acctcccgat cccgaggatt gagtggggcc agggaatggc ccacaagacc    900
atcaagggag ggctctgccc aggcggacgc ctgaggatgg agcgcctgct tgacctcatc    960
aagtacggca gggttgaccc gtcaaggctc ataacccaca gttcaaggg attcgataag    1020 ataccagaag ccctctacct gatgaaggac aagcccaaag acctgataaa gcccgtggtc   1080
atcatagagg agtga                                                   1095

<210> SEQ ID NO 4
<211> LENGTH: 364
<212> TYPE: PRT
<213> ORGANISM: Thermococcus guaymasensis

<400> SEQUENCE: 4

Ser Lys Met Arg Gly Phe Ala Met Val Asp Phe Gly Lys Ala Glu Trp
1               5                   10                  15

Ile Glu Lys Glu Arg Pro Lys Pro Gly Pro Tyr Asp Ala Ile Val Lys
                20                  25                  30

Pro Ile Ala Val Ala Pro Cys Thr Ser Asp Ile His Thr Val Phe Glu
                35                  40                  45

Ala Ala Phe Pro Arg Glu Met Cys Glu Phe Pro Arg Ile Leu Gly His
                50                  55                  60
```

```
Glu Ala Val Gly Glu Val Glu Val Gly Ser His Val Lys Asp Phe
 65                  70                  75                  80

Lys Pro Gly Asp Arg Val Val Pro Ala Ile Thr Pro Asp Trp Arg
                 85                  90                  95

Thr Leu Asp Val Gln Arg Gly Tyr His Gln His Ser Gly Met Leu
            100                 105                 110

Ala Gly Trp Lys Phe Ser Asn Pro Leu Lys Glu Gly Lys Asp Gly
        115                 120                 125

Val Phe Ala Glu Tyr Phe His Val Asn Asp Ala Asp Met Asn Leu Ala
130                 135                 140

His Leu Pro Asp Glu Ile Lys Pro Glu Val Ala Val Met Ala Thr Asp
145                 150                 155                 160

Met Met Thr Thr Gly Phe His Gly Ala Glu Leu Ala Asp Ile Pro Leu
                165                 170                 175

Gly Gly Thr Val Ala Val Ile Gly Ile Gly Pro Val Gly Leu Met Ala
                180                 185                 190

Val Ala Gly Ala Arg Leu Leu Gly Ala Gly Arg Ile Ile Ala Val Gly
            195                 200                 205

Ser Arg Pro Val Cys Val Glu Ala Ala Lys Tyr Tyr Gly Ala Thr Asp
    210                 215                 220

Ile Val Asn Arg Arg Glu His Pro Asp Ile Ala Gly Arg Ile Leu Glu
225                 230                 235                 240

Leu Thr Gly Gly Glu Gly Val Asp Ser Val Ile Ala Gly Gly Asn
                245                 250                 255

Val Asp Val Met Lys Thr Ala Val Lys Ile Val Lys Pro Gly Gly Thr
                260                 265                 270

Val Ala Asn Ile Asn Tyr Phe Gly Ser Gly Asp Tyr Leu Pro Ile Pro
            275                 280                 285

Arg Ile Glu Trp Gly Gln Gly Met Ala His Lys Thr Ile Lys Gly Gly
    290                 295                 300

Leu Cys Pro Gly Gly Arg Leu Arg Met Glu Arg Leu Leu Asp Leu Ile
305                 310                 315                 320

Lys Tyr Gly Arg Val Asp Pro Ser Arg Leu Ile Thr His Lys Phe Lys
                325                 330                 335

Gly Phe Asp Lys Ile Pro Glu Ala Leu Tyr Leu Met Lys Asp Lys Pro
            340                 345                 350

Lys Asp Leu Ile Lys Pro Val Val Ile Ile Glu Glu
        355                 360

<210> SEQ ID NO 5
<211> LENGTH: 1098
<212> TYPE: DNA
<213> ORGANISM: Artificial Sequence
<220> FEATURE:
<223> OTHER INFORMATION: TgADH gene mutant

<400> SEQUENCE: 5
atgagcaaga tgcgcggttt tgcaatggtg gacttcggca aggccgagtg gattgagaag      60
gagaggccga agcccgggcc gtacgatgca atcgtcaagc ccattgcagt cgccccatgc     120
acctcggaca tccacacggt cttttgaggca gcgtttccca gggagatgag cgagttcccg    180
cgcatactgg gtcacgaagc agtcggagag gtagtcgagg tcggaagcca cgtcaaggac    240
ttcaagcccg ggacagggt tgttgtcccg gcaataactc ccgactggag gacccttgac     300
gttcagaggg gctaccacca gcactccggt ggaatgctcg ccggatgaa gttcagcaac     360 cccctcaagg agggcggtaa ggacggtgtg tttgcagaat acttccacgt caacgacgct    420
```

-continued

```
gacatgaacc tggcacacct tccggacgaa atcaagccgg aagtcgctgt catggccacc      480
gacatgatga ccacgggatt ccacggcgcc gagctcgccg acattccgct cggaggaaca      540
gtcgccgtca ttggaattgg accggtcggc ctgatggcgg ttgccggggc aagactgctc      600
ggtgccggaa ggatcatcgc ggtcggcagc aggccggtgt gcgttgaggc cgctaagtac      660
tacggagcca ccgacatagt caaccgcagg gagcacccgg acatcgccgg aaggatcctg      720
gagctgaccg gtggagaggg tgttgattcg gtgataatcg ccggcggaaa cgttgacgta      780
atgaagaccg cggtgaagat agtcaagccc ggaggaacgg tggccaacat caactacttc      840
ggcagcggtg actacctccc gatcccgagg attgagtggg ccagggaat ggcccacaag       900 accatcaagg gagggctctg cccaggcgga cgcctgagga tggagcgcct gcttgacctc      960
atcaagtacg cagggttga cccgtcaagg ctcataaccc acaagttcaa gggattcgat      1020
aagataccag aagccctcta cctgatgaag gacaagccca agacctgat aaagcccgtg      1080 gtcatcatag aggagtga                                                   1098
```

<210> SEQ ID NO 6
<211> LENGTH: 365
<212> TYPE: PRT
<213> ORGANISM: Artificial Sequence
<220> FEATURE:
<223> OTHER INFORMATION: From TgADH gene mutant

<400> SEQUENCE: 6

```
Met Ser Lys Met Arg Gly Phe Ala Met Val Asp Phe Gly Lys Ala Glu
1               5                   10                  15

Trp Ile Glu Lys Glu Arg Pro Lys Pro Gly Pro Tyr Asp Ala Ile Val
            20                  25                  30

Lys Pro Ile Ala Val Ala Pro Cys Thr Ser Asp Ile His Thr Val Phe
        35                  40                  45

Glu Ala Ala Phe Pro Arg Glu Met Ser Glu Phe Pro Arg Ile Leu Gly
    50                  55                  60

His Glu Ala Val Gly Glu Val Val Glu Val Gly Ser His Val Lys Asp
65                  70                  75                  80

Phe Lys Pro Gly Asp Arg Val Val Val Pro Ala Ile Thr Pro Asp Trp
                85                  90                  95

Arg Thr Leu Asp Val Gln Arg Gly Tyr His Gln His Ser Gly Gly Met
            100                 105                 110

Leu Ala Gly Trp Lys Phe Ser Asn Pro Leu Lys Glu Gly Gly Lys Asp
        115                 120                 125

Gly Val Phe Ala Glu Tyr Phe His Val Asn Asp Ala Asp Met Asn Leu
    130                 135                 140

Ala His Leu Pro Asp Glu Ile Lys Pro Glu Val Ala Val Met Ala Thr
145                 150                 155                 160

Asp Met Met Thr Thr Gly Phe His Gly Ala Glu Leu Ala Asp Ile Pro
                165                 170                 175

Leu Gly Gly Thr Val Ala Val Ile Gly Ile Gly Pro Val Gly Leu Met
            180                 185                 190

Ala Val Ala Gly Ala Arg Leu Leu Gly Ala Gly Arg Ile Ile Ala Val
        195                 200                 205

Gly Ser Arg Pro Val Cys Val Glu Ala Ala Lys Tyr Tyr Gly Ala Thr
    210                 215                 220

Asp Ile Val Asn Arg Arg Glu His Pro Asp Ile Ala Gly Arg Ile Leu
225                 230                 235                 240
```

-continued

```
Glu Leu Thr Gly Gly Glu Val Asp Ser Val Ile Ile Ala Gly Gly
                245                 250                 255
Asn Val Asp Val Met Lys Thr Ala Val Lys Ile Val Lys Pro Gly Gly
            260                 265                 270
Thr Val Ala Asn Ile Asn Tyr Phe Gly Ser Gly Asp Tyr Leu Pro Ile
        275                 280                 285
Pro Arg Ile Glu Trp Gly Gln Gly Met Ala His Lys Thr Ile Lys Gly
    290                 295                 300
Gly Leu Cys Pro Gly Gly Arg Leu Arg Met Glu Arg Leu Leu Asp Leu
305                 310                 315                 320
Ile Lys Tyr Gly Arg Val Asp Pro Ser Arg Leu Ile Thr His Lys Phe
                325                 330                 335
Lys Gly Phe Asp Lys Ile Pro Glu Ala Leu Tyr Leu Met Lys Asp Lys
            340                 345                 350
Pro Lys Asp Leu Ile Lys Pro Val Val Ile Ile Glu Glu
        355                 360                 365

<210> SEQ ID NO 7
<211> LENGTH: 1254
<212> TYPE: DNA
<213> ORGANISM: Artificial Sequence
<220> FEATURE:
<223> OTHER INFORMATION: TgADH gene including N-terminal residue M and
      part of vector pET30a

<400> SEQUENCE: 7
atgcaccatc atcatcatca ttcttctggt ctggtgccac gcggttctgg tatgaaagaa      60
accgctgctg ctaaattcga acgccagcac atggacagcc agatctggg taccgacgac     120 gacgacaagg ccatggctga tatcggatcc gaattcatga gcaagatgcg cggttttgca     180
atggtggact tcggcaaggc cgagtggatt gagaaggaga ggccgaagcc cgggccgtac     240
gatgcaatcg tcaagcccat tgcagtcgcc catgcacct cggacatcca cacggtcttt     300
gaggcagcgt ttcccaggga gatgtgtgag ttcccgcgca tactgggtca cgaagcagtc     360
ggagaggtag tcgaggtcgg aagccacgtc aaggacttca gccccgggga cagggttgtt     420
gtcccggcaa taactcccga ctggaggacc cttgacgttc agagggcta ccaccagcac     480 tccggtggaa tgctcgccgg atggaagttc agcaaccccc tcaaggaggg cggtaaggac     540
ggtgtgtttg cagaatactt ccacgtcaac gacgctgaca tgaacctggc acaccttccg     600
gacgaaatca gccggaagt cgctgtcatg gccaccgaca tgatgaccac gggattccac     660
ggcgccgagc tcgccgacat tccgctcgga ggaacagtcg ccgtcattgg aattggaccg     720
gtcggcctga tggcggttgc cggggcaaga ctgctcggtg ccggaaggat catcgcggtc     780
ggcagcaggc cggtgtgcgt tgaggccgct aagtactacg gagccaccga catagtcaac     840
cgcagggagc acccggacat cgccggaagg atcctggagc tgaccggtgg agagggtgtt     900
gattcggtga taatcgccgg cggaaacgtt gacgtaatga gaccgcggt gaagatagtc     960 aagcccggag gaacggtggc caacatcaac tacttcggca gcggtgacta cctccccgatc    1020 ccgaggattg agtggggcca gggaatggcc cacaagacca tcaagggagg ctctgcccca    1080
ggcggacgcc tgaggatgga gcgcctgctt gacctcatca gtacggcag ggttgacccg     1140 tcaaggctca taacccacaa gttcaaggga ttcgataaga taccagaagc cctctacctg    1200
atgaaggaca agcccaaaga cctgataaag cccgtggtca tcatagagga gtga          1254

<210> SEQ ID NO 8
<211> LENGTH: 417
```

<212> TYPE: PRT
<213> ORGANISM: Artificial Sequence
<220> FEATURE:
<223> OTHER INFORMATION: Wild-type with vector coding region

<400> SEQUENCE: 8

```
Met His His His His His Ser Ser Gly Leu Val Pro Arg Gly Ser
1               5                   10                  15

Gly Met Lys Glu Thr Ala Ala Lys Phe Glu Arg Gln His Met Asp
                20                  25                  30

Ser Pro Asp Leu Gly Thr Asp Asp Asp Lys Ala Met Ala Asp Ile
                35                  40                  45

Gly Ser Glu Phe Met Ser Lys Met Arg Gly Phe Ala Met Val Asp Phe
    50                  55                  60

Gly Lys Ala Glu Trp Ile Glu Lys Glu Arg Pro Lys Pro Gly Pro Tyr
65                  70                  75                  80

Asp Ala Ile Val Lys Pro Ile Ala Val Ala Pro Cys Thr Ser Asp Ile
                85                  90                  95

His Thr Val Phe Glu Ala Ala Phe Pro Arg Glu Met Cys Glu Phe Pro
                100                 105                 110

Arg Ile Leu Gly His Glu Ala Val Gly Glu Val Val Glu Val Gly Ser
                115                 120                 125

His Val Lys Asp Phe Lys Pro Gly Asp Arg Val Val Val Pro Ala Ile
                130                 135                 140

Thr Pro Asp Trp Arg Thr Leu Asp Val Gln Arg Gly Tyr His Gln His
145                 150                 155                 160

Ser Gly Gly Met Leu Ala Gly Trp Lys Phe Ser Asn Pro Leu Lys Glu
                165                 170                 175

Gly Gly Lys Asp Gly Val Phe Ala Glu Tyr Phe His Val Asn Asp Ala
                180                 185                 190

Asp Met Asn Leu Ala His Leu Pro Asp Glu Ile Lys Pro Glu Val Ala
                195                 200                 205

Val Met Ala Thr Asp Met Met Thr Thr Gly Phe His Gly Ala Glu Leu
                210                 215                 220

Ala Asp Ile Pro Leu Gly Gly Thr Val Ala Val Ile Gly Ile Gly Pro
225                 230                 235                 240

Val Gly Leu Met Ala Val Ala Gly Ala Arg Leu Leu Gly Ala Gly Arg
                245                 250                 255

Ile Ile Ala Val Gly Ser Arg Pro Val Cys Val Glu Ala Ala Lys Tyr
                260                 265                 270

Tyr Gly Ala Thr Asp Ile Val Asn Arg Arg Glu His Pro Asp Ile Ala
                275                 280                 285

Gly Arg Ile Leu Glu Leu Thr Gly Gly Glu Gly Val Asp Ser Val Ile
                290                 295                 300

Ile Ala Gly Gly Asn Val Asp Val Met Lys Thr Ala Val Lys Ile Val
305                 310                 315                 320

Lys Pro Gly Gly Thr Val Ala Asn Ile Asn Tyr Phe Gly Ser Gly Asp
                325                 330                 335

Tyr Leu Pro Ile Pro Arg Ile Glu Trp Gly Gln Gly Met Ala His Lys
                340                 345                 350

Thr Ile Lys Gly Gly Leu Cys Pro Gly Gly Arg Leu Arg Met Glu Arg
                355                 360                 365

Leu Leu Asp Leu Ile Lys Tyr Gly Arg Val Asp Pro Ser Arg Leu Ile
                370                 375                 380

Thr His Lys Phe Lys Gly Phe Asp Lys Ile Pro Glu Ala Leu Tyr Leu
```

```
385                 390                 395                 400
Met Lys Asp Lys Pro Lys Asp Leu Ile Lys Pro Val Val Ile Ile Glu
                405                 410                 415

Glu
```

<210> SEQ ID NO 9
<211> LENGTH: 1254
<212> TYPE: DNA
<213> ORGANISM: Artificial Sequence
<220> FEATURE:
<223> OTHER INFORMATION: TgADH-C56S gene including N-terminal residue M
      and part of vector pET30a

<400> SEQUENCE: 9

```
atgcaccatc atcatcatca ttcttctggt ctggtgccac gcggttctgg tatgaaagaa      60
accgctgctg ctaaattcga acgccagcac atggacagcc agatctgggt accgacgac     120
gacgacaagg ccatggctga tatcggatcc gaattcatga gcaagatgcg cggttttgca    180
atggtggact tcggcaaggc cgagtggatt gagaaggaga ggccgaagcc cgggccgtac    240
gatgcaatcg tcaagcccat tgcagtcgcc ccatgcacct cggacatcca cacggtcttt    300
gaggcagcgt ttcccaggga gatgagcgag ttcccgcgca tactgggtca cgaagcagtc    360
ggagaggtag tcgaggtcgg aagccacgtc aaggacttca gcccggggga cagggttgtt    420
gtcccggcaa taactcccga ctggaggacc cttgacgttc agaggggcta ccaccagcac    480
tccggtggaa tgctcgccgg atggaagttc agcaaccccc tcaaggaggg cggtaaggac    540
ggtgtgtttg cagaatactt ccacgtcaac gacgctgaca tgaacctggc acaccttccg    600
gacgaaatca gccggaagt cgctgtcatg gccaccgaca tgatgaccac gggattccac    660
ggcgccgagc tcgccgacat tccgctcgga ggaacagtcg ccgtcattgg aattggaccg    720
gtcggcctga tggcggttgc cggggcaaga ctgctcggtg ccggaaggat catcgcggtc    780
ggcagcaggc cggtgtgcgt tgaggccgct aagtactacg agccaccga catagtcaac    840
cgcagggagc accccgacat cgccggaagg atcctggagc tgaccggtgg agagggtgtt    900
gattcggtga taatcgccgg cggaaacgtt gacgtaatga agaccgcggt gaagatagtc    960
aagcccggag gaacggtggc caacatcaac tacttcggca gcggtgacta cctcccgatc   1020
ccgaggattg agtggggcca gggaatggcc cacaagacca tcaagggagg ctctgcccca   1080
ggcggacgcc tgaggatgga gcgcctgctt gacctcatca gtacggcag ggttgacccg    1140
tcaaggctca taacccacaa gttcaaggga ttcgataaga taccagaagc cctctacctg   1200
atgaaggaca agcccaaaga cctgataaag cccgtggtca tcatagagga gtga         1254
```

<210> SEQ ID NO 10
<211> LENGTH: 417
<212> TYPE: PRT
<213> ORGANISM: Artificial Sequence
<220> FEATURE:
<223> OTHER INFORMATION: C56S with vector coding region

<400> SEQUENCE: 10

```
Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
                20                  25                  30

Ser Pro Asp Leu Gly Thr Asp Asp Asp Lys Ala Met Ala Asp Ile
            35                  40                  45

Gly Ser Glu Phe Met Ser Lys Met Arg Gly Phe Ala Met Val Asp Phe
```

```
                50                  55                  60
Gly Lys Ala Glu Trp Ile Glu Lys Glu Arg Pro Lys Pro Gly Pro Tyr
 65                  70                  75                  80

Asp Ala Ile Val Lys Pro Ile Ala Val Ala Pro Cys Thr Ser Asp Ile
                 85                  90                  95

His Thr Val Phe Glu Ala Ala Phe Pro Arg Glu Met Ser Glu Phe Pro
                100                 105                 110

Arg Ile Leu Gly His Glu Ala Val Gly Glu Val Val Glu Val Gly Ser
            115                 120                 125

His Val Lys Asp Phe Lys Pro Gly Asp Arg Val Val Pro Ala Ile
        130                 135                 140

Thr Pro Asp Trp Arg Thr Leu Asp Val Gln Arg Gly Tyr His Gln His
145                 150                 155                 160

Ser Gly Gly Met Leu Ala Gly Trp Lys Phe Ser Asn Pro Leu Lys Glu
                165                 170                 175

Gly Gly Lys Asp Gly Val Phe Ala Glu Tyr Phe His Val Asn Asp Ala
            180                 185                 190

Asp Met Asn Leu Ala His Leu Pro Asp Glu Ile Lys Pro Glu Val Ala
        195                 200                 205

Val Met Ala Thr Asp Met Met Thr Thr Gly Phe His Gly Ala Glu Leu
210                 215                 220

Ala Asp Ile Pro Leu Gly Gly Thr Val Ala Val Ile Gly Ile Gly Pro
225                 230                 235                 240

Val Gly Leu Met Ala Val Ala Gly Ala Arg Leu Leu Gly Ala Gly Arg
                245                 250                 255

Ile Ile Ala Val Gly Ser Arg Pro Val Cys Val Glu Ala Ala Lys Tyr
            260                 265                 270

Tyr Gly Ala Thr Asp Ile Val Asn Arg Arg Glu His Pro Asp Ile Ala
        275                 280                 285

Gly Arg Ile Leu Glu Leu Thr Gly Gly Glu Gly Val Asp Ser Val Ile
290                 295                 300

Ile Ala Gly Gly Asn Val Asp Val Met Lys Thr Ala Val Lys Ile Val
305                 310                 315                 320

Lys Pro Gly Gly Thr Val Ala Asn Ile Asn Tyr Phe Gly Ser Gly Asp
                325                 330                 335

Tyr Leu Pro Ile Pro Arg Ile Glu Trp Gly Gln Gly Met Ala His Lys
            340                 345                 350

Thr Ile Lys Gly Gly Leu Cys Pro Gly Gly Arg Leu Arg Met Glu Arg
        355                 360                 365

Leu Leu Asp Leu Ile Lys Tyr Gly Arg Val Asp Pro Ser Arg Leu Ile
370                 375                 380

Thr His Lys Phe Lys Gly Phe Asp Lys Ile Pro Glu Ala Leu Tyr Leu
385                 390                 395                 400

Met Lys Asp Lys Pro Lys Asp Leu Ile Lys Pro Val Val Ile Ile Glu
                405                 410                 415

Glu

<210> SEQ ID NO 11
<211> LENGTH: 21
<212> TYPE: DNA
<213> ORGANISM: Artificial Sequence
<220> FEATURE:
<223> OTHER INFORMATION: Primer TGADHNF
<220> FEATURE:
<221> NAME/KEY: misc_feature
<222> LOCATION: (9)..(9)
```

-continued

<223> OTHER INFORMATION: n is a, c, g, or t

<400> SEQUENCE: 11
aaratgmgng gttttgcaat g                                              21

<210> SEQ ID NO 12
<211> LENGTH: 18
<212> TYPE: DNA
<213> ORGANISM: Artificial Sequence
<220> FEATURE:
<223> OTHER INFORMATION: Primer TGADHIR

<400> SEQUENCE: 12
ggagtgctgg tgatatcc                                                  18

<210> SEQ ID NO 13
<211> LENGTH: 20
<212> TYPE: DNA
<213> ORGANISM: Artificial Sequence
<220> FEATURE:
<223> OTHER INFORMATION: Primer TGMAYN01

<400> SEQUENCE: 13
tctccttctc aatccactcg                                                20

<210> SEQ ID NO 14
<211> LENGTH: 18
<212> TYPE: DNA
<213> ORGANISM: Artificial Sequence
<220> FEATURE:
<223> OTHER INFORMATION: Primer TGMAYC02

<400> SEQUENCE: 14
gcaataactc ccgactgg                                                  18

<210> SEQ ID NO 15
<211> LENGTH: 20
<212> TYPE: DNA
<213> ORGANISM: Artificial Sequence
<220> FEATURE:
<223> OTHER INFORMATION: Primer TGMAY28C01

<400> SEQUENCE: 15
tgccgaagta gttgatgttg                                                20

<210> SEQ ID NO 16
<211> LENGTH: 18
<212> TYPE: DNA
<213> ORGANISM: Artificial Sequence
<220> FEATURE:
<223> OTHER INFORMATION: Primer TGMAY28C02
<220> FEATURE:
<221> NAME/KEY: misc_feature
<222> LOCATION: (16)..(16)
<223> OTHER INFORMATION: n is a, c, g, or t

<400> SEQUENCE: 16
gaggtcaagc aggcgntc                                                  18

<210> SEQ ID NO 17
<211> LENGTH: 19
<212> TYPE: DNA
<213> ORGANISM: Artificial Sequence
<220> FEATURE:
<223> OTHER INFORMATION: Primer TGJL1N1
<220> FEATURE:
<221> NAME/KEY: misc_feature
<222> LOCATION: (6)..(6)

```
<223> OTHER INFORMATION: n is a, c, g, or t

<400> SEQUENCE: 17
atgtcnaagg atgcgcggt                                                 19

<210> SEQ ID NO 18
<211> LENGTH: 19
<212> TYPE: DNA
<213> ORGANISM: Artificial Sequence
<220> FEATURE:
<223> OTHER INFORMATION: Primer TGJL1N2
<220> FEATURE:
<221> NAME/KEY: misc_feature
<222> LOCATION: (6)..(6)
<223> OTHER INFORMATION: y is t or c

<400> SEQUENCE: 18
atgagyaagg atgcgcggt                                                 19

<210> SEQ ID NO 19
<211> LENGTH: 30
<212> TYPE: DNA
<213> ORGANISM: Artificial Sequence
<220> FEATURE:
<223> OTHER INFORMATION: Primer TGECN

<400> SEQUENCE: 19
tagaattcat gagcaagatg cgcggttttc                                     30

<210> SEQ ID NO 20
<211> LENGTH: 27
<212> TYPE: DNA
<213> ORGANISM: Artificial Sequence
<220> FEATURE:
<223> OTHER INFORMATION: Primer TGXHR

<400> SEQUENCE: 20
acctcgagtc actcctctat gatgacc                                        27

<210> SEQ ID NO 21
<211> LENGTH: 15
<212> TYPE: PRT
<213> ORGANISM: Artificial Sequence
<220> FEATURE:
<223> OTHER INFORMATION: Conserved catalytic zinc-binding motif
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(11)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid

<400> SEQUENCE: 21

Gly His Glu Xaa Xaa Gly Xaa Xaa Xaa Xaa Xaa Gly Xaa Xaa Val
1               5                   10                  15

<210> SEQ ID NO 22
<211> LENGTH: 6
<212> TYPE: PRT
<213> ORGANISM: Artificial Sequence
<220> FEATURE:
<223> OTHER INFORMATION: Conserved binding motif of cofactor NADH
<220> FEATURE:
<221> NAME/KEY: misc_feature
```

```
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 22

Gly Xaa Gly Xaa Xaa Gly
1               5

<210> SEQ ID NO 23
<211> LENGTH: 15
<212> TYPE: PRT
<213> ORGANISM: Artificial Sequence
<220> FEATURE:
<223> OTHER INFORMATION: TgADH binding motif of catalytic zinc residues
      63-77

<400> SEQUENCE: 23

Gly His Glu Ala Val Gly Glu Val Val Glu Val Gly Ser His Val
1               5                   10                  15

<210> SEQ ID NO 24
<211> LENGTH: 6
<212> TYPE: PRT
<213> ORGANISM: Artificial Sequence
<220> FEATURE:
<223> OTHER INFORMATION: TgADH binding motif of cofactor NADH residues
      184-189

<400> SEQUENCE: 24

Gly Ile Gly Pro Val Gly
1               5

<210> SEQ ID NO 25
<211> LENGTH: 6
<212> TYPE: PRT
<213> ORGANISM: Artificial Sequence
<220> FEATURE:
<223> OTHER INFORMATION: Unique TgAGD fragment residues 119 to 124

<400> SEQUENCE: 25

Pro Leu Lys Glu Gly Gly
1               5

<210> SEQ ID NO 26
<211> LENGTH: 13
<212> TYPE: PRT
<213> ORGANISM: Artificial Sequence
<220> FEATURE:
<223> OTHER INFORMATION: Internal TgADH  sequences

<400> SEQUENCE: 26

Gly Tyr His Gln His Ser Gly Gly Met Leu Ala Gly Trp
1               5                   10

<210> SEQ ID NO 27
<211> LENGTH: 11
<212> TYPE: PRT
<213> ORGANISM: Artificial Sequence
<220> FEATURE:
<223> OTHER INFORMATION: native TgADH N-terminal sequence of mature
      enzyme

<400> SEQUENCE: 27

Ser Lys Met Arg Gly Phe Ala Met Val Asp Phe
1               5                   10
```

<210> SEQ ID NO 28
<211> LENGTH: 7
<212> TYPE: PRT
<213> ORGANISM: Artificial Sequence
<220> FEATURE:
<223> OTHER INFORMATION: Internal sequence of TgADH

<400> SEQUENCE: 28

```
Asp Phe Lys Pro Gly Asp Arg
1               5
```

<210> SEQ ID NO 29
<211> LENGTH: 11
<212> TYPE: PRT
<213> ORGANISM: Artificial Sequence
<220> FEATURE:
<223> OTHER INFORMATION: Internal sequence of TgADH

<400> SEQUENCE: 29

```
Val Val Val Pro Ala Ile Thr Pro Asp Trp Arg
1               5                   10
```

<210> SEQ ID NO 30
<211> LENGTH: 13
<212> TYPE: PRT
<213> ORGANISM: Artificial Sequence
<220> FEATURE:
<223> OTHER INFORMATION: Internal sequence of TgADH

<400> SEQUENCE: 30

```
Gly Tyr His Gln His Ser Gly Gly Met Leu Ala Gly Trp
1               5                   10
```

<210> SEQ ID NO 31
<211> LENGTH: 352
<212> TYPE: PRT
<213> ORGANISM: Thermoanaerobacter brockii

<400> SEQUENCE: 31

```
Met Lys Gly Phe Ala Met Leu Ser Ile Gly Lys Val Gly Trp Ile Glu
1               5                   10                  15

Lys Glu Lys Pro Ala Pro Gly Pro Phe Asp Ala Ile Val Arg Pro Leu
                20                  25                  30

Ala Val Ala Pro Cys Thr Ser Asp Ile His Thr Val Phe Glu Gly Ala
            35                  40                  45

Ile Gly Glu Arg His Asn Met Ile Leu Gly His Glu Ala Val Gly Glu
        50                  55                  60

Val Val Glu Val Gly Ser Glu Val Lys Asp Phe Lys Pro Gly Asp Arg
65                  70                  75                  80

Val Val Val Pro Ala Ile Thr Pro Asp Trp Arg Thr Ser Glu Val Gln
                85                  90                  95

Arg Gly Tyr His Gln His Ser Gly Gly Met Leu Ala Gly Trp Lys Phe
            100                 105                 110

Ser Asn Val Lys Asp Gly Val Phe Gly Glu Phe Phe His Val Asn Asp
        115                 120                 125

Ala Asp Met Asn Leu Ala His Leu Pro Lys Glu Ile Pro Leu Glu Ala
    130                 135                 140

Ala Val Met Ile Pro Asp Met Met Thr Thr Gly Phe His Gly Ala Glu
145                 150                 155                 160

Leu Ala Asp Ile Glu Leu Gly Ala Thr Val Ala Val Leu Gly Ile Gly
                165                 170                 175
```

```
Pro Val Gly Leu Met Ala Val Ala Gly Ala Lys Leu Arg Gly Ala Gly
            180                 185                 190

Arg Ile Ile Ala Val Gly Ser Arg Pro Val Cys Val Asp Ala Ala Lys
            195                 200                 205

Tyr Tyr Gly Ala Thr Asp Ile Val Asn Tyr Lys Asp Gly Pro Ile Glu
            210                 215                 220

Ser Gln Ile Met Asn Leu Thr Glu Gly Lys Gly Val Asp Ala Ala Ile
225                 230                 235                 240

Ile Ala Gly Gly Asn Ala Asp Ile Met Ala Thr Ala Val Lys Ile Val
                245                 250                 255

Lys Pro Gly Gly Thr Ile Ala Asn Val Asn Tyr Phe Gly Glu Gly Glu
            260                 265                 270

Val Leu Pro Val Pro Arg Leu Glu Trp Gly Cys Gly Met Ala His Lys
            275                 280                 285

Thr Ile Lys Gly Gly Leu Cys Pro Gly Gly Arg Leu Arg Met Glu Arg
            290                 295                 300

Leu Ile Asp Leu Val Phe Tyr Lys Arg Val Asp Pro Ser Lys Leu Val
305                 310                 315                 320

Thr His Val Phe Arg Gly Phe Asp Asn Ile Glu Lys Ala Phe Met Leu
            325                 330                 335

Met Lys Asp Lys Pro Lys Asp Leu Ile Lys Pro Val Val Ile Leu Ala
            340                 345                 350

<210> SEQ ID NO 32
<211> LENGTH: 351
<212> TYPE: PRT
<213> ORGANISM: Clostridium beijerinckii

<400> SEQUENCE: 32

Met Lys Gly Phe Ala Met Leu Gly Ile Asn Lys Leu Gly Trp Ile Glu
1               5                   10                  15

Lys Glu Arg Pro Val Ala Gly Ser Tyr Asp Ala Ile Val Arg Pro Leu
            20                  25                  30

Ala Val Ser Pro Cys Thr Ser Asp Ile His Thr Val Phe Glu Gly Ala
            35                  40                  45

Leu Gly Asp Arg Lys Asn Met Ile Leu Gly His Glu Ala Val Gly Glu
        50                  55                  60

Val Val Glu Val Gly Ser Glu Val Lys Asp Phe Lys Pro Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Gly Glu Tyr Phe His Val Asn Asp
            115                 120                 125

Ala Asp Met Asn Leu Ala Ile Leu Pro Lys Asp Met Pro Leu Glu Asn
            130                 135                 140

Ala Val Met Ile Thr Asp Met Met Thr Thr Gly Phe His Gly Ala Glu
145                 150                 155                 160

Leu Ala Asp Ile Gln Met Gly Ser Ser Val Val Val Ile Gly Ile Gly
                165                 170                 175

Ala Val Gly Leu Met Gly Ile Ala Gly Ala Lys Leu Arg Gly Ala Gly
            180                 185                 190

Arg Ile Ile Gly Val Gly Ser Arg Pro Ile Cys Val Glu Ala Ala Lys
            195                 200                 205
```

-continued

```
Phe Tyr Gly Ala Thr Asp Ile Leu Asn Tyr Lys Asn Gly His Ile Val
            210                 215                 220
Asp Gln Val Met Lys Leu Thr Asn Gly Lys Gly Val Asp Arg Val Ile
225                 230                 235                 240
Met Ala Gly Gly Gly Ser Glu Thr Leu Ser Gln Ala Val Ser Met Val
                245                 250                 255
Lys Pro Gly Gly Ile Ile Ser Asn Ile Asn Tyr His Gly Ser Gly Asp
            260                 265                 270
Ala Leu Leu Ile Pro Arg Val Glu Trp Gly Cys Gly Met Ala His Lys
        275                 280                 285
Thr Ile Lys Gly Gly Leu Cys Pro Gly Gly Arg Leu Arg Ala Glu Met
    290                 295                 300
Leu Arg Asp Met Val Val Tyr Asn Arg Val Asp Leu Ser Lys Leu Val
305                 310                 315                 320
Thr His Val Tyr His Gly Phe Asp His Ile Glu Glu Ala Leu Leu Leu
                325                 330                 335
Met Lys Asp Lys Pro Lys Asp Leu Ile Lys Ala Val Val Ile Leu
            340                 345                 350

<210> SEQ ID NO 33
<211> LENGTH: 31
<212> TYPE: DNA
<213> ORGANISM: Artificial Sequence
<220> FEATURE:
<223> OTHER INFORMATION: Primer sequence TGECN

<400> SEQUENCE: 33
tagaattcat gagcaagatg cgcggttttg c                              31

<210> SEQ ID NO 34
<211> LENGTH: 45
<212> TYPE: DNA
<213> ORGANISM: Artificial Sequence
<220> FEATURE:
<223> OTHER INFORMATION: Primer TGMR

<400> SEQUENCE: 34
cagtatgcgc gggaactcgc tcatctccct gggaaacgct gcctc               45

<210> SEQ ID NO 35
<211> LENGTH: 27
<212> TYPE: DNA
<213> ORGANISM: Artificial Sequence
<220> FEATURE:
<223> OTHER INFORMATION: Primer TGXHR

<400> SEQUENCE: 35
acctcgagtc actcctctat gatgacc                                   27

<210> SEQ ID NO 36
<211> LENGTH: 45
<212> TYPE: DNA
<213> ORGANISM: Artificial Sequence
<220> FEATURE:
<223> OTHER INFORMATION: Primer TGMF

<400> SEQUENCE: 36
cgtttcccag ggagatgagc gagttcccgc gcatactggg tcacg               45

<210> SEQ ID NO 37
<211> LENGTH: 31
<212> TYPE: DNA
<213> ORGANISM: Artificial Sequence
```

```
-continued

<220> FEATURE:
<223> OTHER INFORMATION: Primer TGECN

<400> SEQUENCE: 37
tagaattcat gagcaagatg cgcggttttg c                              31

<210> SEQ ID NO 38
<211> LENGTH: 27
<212> TYPE: DNA
<213> ORGANISM: Artificial Sequence
<220> FEATURE:
<223> OTHER INFORMATION: Primer TGXHR

<400> SEQUENCE: 38
acctcgagtc actcctctat gatgacc                                    27

<210> SEQ ID NO 39
<211> LENGTH: 50
<212> TYPE: DNA
<213> ORGANISM: Artificial Sequence
<220> FEATURE:
<223> OTHER INFORMATION: TgADH wild type primer

<400> SEQUENCE: 39
gtctttgagg cagcgtttcc cagggagatg tgtgagttcc cgcgcatact           50

<210> SEQ ID NO 40
<211> LENGTH: 50
<212> TYPE: DNA
<213> ORGANISM: Artificial Sequence
<220> FEATURE:
<223> OTHER INFORMATION: TgADH mutant primer

<400> SEQUENCE: 40
gtctttgagg cagcgtttcc cagggagatg agcgagttcc cgcgcatact           50
```